US012640258B2

(12) United States Patent
Ohashi

(10) Patent No.: US 12,640,258 B2
(45) Date of Patent: May 26, 2026

(54) FAILED IMAGE MANAGEMENT APPARATUS, OPERATION METHOD OF FAILED IMAGE MANAGEMENT APPARATUS, AND FAILED IMAGE MANAGEMENT SYSTEM

(71) Applicant: FUJIFILM Corporation, Tokyo (JP)

(72) Inventor: Yosuke Ohashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/525,112

(22) Filed: Nov. 30, 2023

(65) Prior Publication Data

US 2024/0105323 A1     Mar. 28, 2024

Related U.S. Application Data

(63) Continuation of application No. 17/158,145, filed on Jan. 26, 2021, now Pat. No. 11,869,658, which is a
(Continued)

(30) Foreign Application Priority Data

Mar. 27, 2015 (JP) ................................ 2015-067015
Mar. 27, 2015 (JP) ................................ 2015-067016

(51) Int. Cl.
*G16H 40/20* (2018.01)
*G06T 7/00* (2017.01)
(Continued)

(52) U.S. Cl.
CPC ........... *G16H 40/20* (2018.01); *G06T 7/0014* (2013.01); *G16H 30/20* (2018.01); *G16H 30/40* (2018.01);
(Continued)

(58) Field of Classification Search
CPC ........ G16H 40/20; G16H 30/20; G16H 30/40; G16H 40/63; G06T 7/0014; G06T 2207/10116
(Continued)

(56) References Cited

U.S. PATENT DOCUMENTS 7,298,876 B1    11/2007   Marshall et al.
2005/0256743 A1    11/2005   Dale
(Continued)

FOREIGN PATENT DOCUMENTS

GB          2503114 A   * 12/2013   ......... G06K 9/00221
JP       2006-218139 A       8/2006
(Continued)

OTHER PUBLICATIONS

Communication dated Sep. 6, 2019 from the European Patent Office in application No. 16161617.2.
(Continued)

*Primary Examiner* — Jason B Dunham
*Assistant Examiner* — Kimberly A. Sass
(74) *Attorney, Agent, or Firm* — Sughrue Mion, PLLC

(57) ABSTRACT

A first calculator calculates a first index value quantitatively indicating an imaging failure state for each imaging menu using a first calculation formula having a variable based on the number of times of occurrence of imaging failure for each imaging menu and a variable based on the rate of occurrence of imaging failure for each imaging menu. A first extractor automatically extracts a target menu as an imaging menu to be considered to prevent occurrence of imaging failure based on the first index value. A second extractor extracts a consideration image as a failed image associated with the target menu. A screen output controller generates a conference screen for displaying the target menu and the consideration image. A client terminal displays the conference screen on a display panel.

14 Claims, 40 Drawing Sheets

Related U.S. Application Data continuation-in-part of application No. 15/080,744, filed on Mar. 25, 2016, now abandoned.

(51) Int. Cl.
 *G16H 30/20* (2018.01)
 *G16H 30/40* (2018.01)
 *G16H 40/63* (2018.01)

(52) U.S. Cl.
 CPC .... *G16H 40/63* (2018.01); *G06T 2207/10116* (2013.01)

(58) Field of Classification Search
 USPC .......................................................... 705/2
 See application file for complete search history.

(56) References Cited

U.S. PATENT DOCUMENTS

| | | | |
|---|---|---|---|
| 2008/0052112 A1 | 2/2008 | Zahlmann et al. | |
| 2011/0131528 A1* | 6/2011 | Nakamura | A61B 6/563 |
| | | | 715/810 |
| 2012/0188363 A1 | 7/2012 | Hamid et al. | |
| 2013/0184537 A1* | 7/2013 | Konuma | A61B 6/586 |
| | | | 600/300 |
| 2014/0064638 A1* | 3/2014 | Ohta | G06T 3/40 |
| | | | 382/299 |
| 2014/0072192 A1* | 3/2014 | Reiner | G16H 40/20 |
| | | | 382/128 |
| 2015/0149206 A1 | 5/2015 | Jester et al. | |
| 2015/0235365 A1 | 8/2015 | Mankovich et al. | |
| 2017/0164916 A1* | 6/2017 | Kosuge | A61B 6/465 |

FOREIGN PATENT DOCUMENTS

| | | | | |
|---|---|---|---|---|
| WO | WO-2013061321 A1 * | 5/2013 | | G16H 80/00 |
| WO | WO-2013109525 A1 * | 7/2013 | | A61B 1/00142 |

OTHER PUBLICATIONS

Communication dated Aug. 30, 2016 from the European Patent Office in counterpart Application No. 16161617.2.

Communication dated Jul. 7, 2017, from the European Patent Office in counterpart European Application No. 16161617.2.

* cited by examiner

FIG.2

| ORDER ID | DEPARTMENT AS REQUESTOR | STAFF ID (REQUESTOR) | PATIENT ID | BODY PART TO BE IMAGED/ IMAGING POSTURE/ IMAGING DIRECTION |
|---|---|---|---|---|
| OD0001 | I.M. DEP. | D0001 | P0500 | CHEST PART/ UPRIGHT IMAGING POSTURE/ FRONT |

IMAGING ORDER

18

CONSOLE                                                    25

| IMAGING MENU | IMAGING CONDITION |
|---|---|
| CHEST PART/ UPRIGHT IMAGING POSTURE/ FRONT | TUBE VOLTAGE:100kV TUBE CURRENT:200mA IRRADIATION TIME:20ms |
| CHEST PART/ UPRIGHT IMAGING POSTURE/ REAR | TUBE VOLTAGE:120kV TUBE CURRENT:220mA IRRADIATION TIME:25ms |
| ABDOMINAL PART/ UPRIGHT IMAGING POSTURE/ FRONT | TUBE VOLTAGE:150kV TUBE CURRENT:250mA IRRADIATION TIME:25ms |
| ABDOMINAL PART/ UPRIGHT IMAGING POSTURE/ REAR | TUBE VOLTAGE:155kV TUBE CURRENT:260mA IRRADIATION TIME:28ms |

RADIATION SOURCE CONTROLLER — 16

FIG.4

| | |
|---|---|
| FILE ID | F0001 |
| DATE AND TIME OF IMAGING | 2015.03.14 10:15 |
| PATIENT ID | P0500 |
| PATIENT NAME | FUJIO FUJITA |
| GENDER | MALE |
| DATE OF BIRTH | 1985.09.25 |
| AGE | 28 |
| BODY HEIGHT | 173 |
| BODY WEIGHT | 75 |
| IP/ OP CLASSIFICATION | OUTPATIENT |
| ORDER ID | OD0100 |
| IMAGING MENU | C.P./ U.I.P./ F |
| TUBE VOLTAGE | 100 |
| TUBE CURRENT | 200 |
| IRRADIATION TIME | 20 |
| STAFF ID (RADIOGRAPHER) | R0001 |
| IMAGING ROOM | FIRST IMAGING ROOM |
| IMAGING FAILURE FLAG | 1 |

| | DESIGNATION INFORMATION |
|---|---|
| STAFF ID (PARTICIPANT) | R0001, R0002, R0005, R0008 |
| NUMBER OF TARGET MENUS | 1 |
| NUMBER OF CONSIDERATION IMAGES | 50 |
| PERIOD | FROM 2015.01.05 TO 2015.03.13 |
| NARROWING-DOWN CONDITION | GENDER:MALE IP/ OP: OP |

STAFF ID:R0001

| IMAGING MENU | T.NUM.I | NUM.I.F. | R.I.F. | RANK OF NUM.I.F. | VARIABLE X3 BASED ON NUM.I.F. | RANK OF R.I.F. | VARIABLE X4 BASED ON R.I.F. |
|---|---|---|---|---|---|---|---|
| C.P./U.I.P./F | 20 | 5 | 25% | 1 | 10 | 2 | 9 |
| C.P./U.I.P./R | 10 | 4 | 40% | 2 | 9 | 1 | 10 |
| A.P./U.I.P./F | 2 | 0 | 0% | 15 | 0 | 15 | 0 |
| A.P./U.I.P./R | 5 | 0 | 0% | 15 | 0 | 15 | 0 |

STAFF ID:R0005

| VARIABLE X7 BASED ON NUM.I.F. |
|---|
| VARIABLE X8 BASED ON R.I.F. |

STAFF ID:R0002

| IMAGING MENU | T.NUM.I | NUM.I.F. | R.I.F. | RANK OF NUM.I.F. | VARIABLE X5 BASED ON NUM.I.F. | RANK OF R.I.F. | VARIABLE X6 BASED ON R.I.F. |
|---|---|---|---|---|---|---|---|
| C.P./U.I.P./F | 50 | 10 | 20% | 1 | 10 | 3 | 8 |
| C.P./U.I.P./R | 50 | 2 | 4% | 6 | 5 | 10 | 1 |
| A.P./U.I.P./F | 25 | 2 | 8% | 6 | 5 | 8 | 3 |
| A.P./U.I.P./R | 10 | 3 | 30% | 5 | 6 | 1 | 10 |

STAFF ID:R0008

| VARIABLE X9 BASED ON NUM.I.F. |
|---|
| VARIABLE X10 BASED ON R.I.F. |

| DATE OF CONFERENCE | PREVIOUS STAFF ID (PARTICIPANT) | PREVIOUS TARGET MENU |
|---|---|---|
| 2015.02.27 | R0001, R0004, R0007, R0008 | CHEST PART/ UPRIGHT IMAGING POSTURE/ FRONT, CHEST PART/ UPRIGHT IMAGING POSTURE/ REAR |

78B

| IMAGING MENU | PREVIOUS NUMBER OF TIMES OF OCCURRENCE OF IMAGING FAILURE |
|---|---|
| CHEST PART/ UPRIGHT IMAGING POSTURE/ FRONT | 15 |
| CHEST PART/ UPRIGHT IMAGING POSTURE/ REAR | 30 |
| ABDOMINAL PART/ UPRIGHT IMAGING POSTURE/ FRONT | 5 |
| ABDOMINAL PART/ UPRIGHT IMAGING POSTURE/ REAR | 36 |

| INCREASING RATE | VARIABLE |
|---|---|
| 100% OR MORE | 10 |
| 90% OR MORE TO LESS THAN 100% | 9 |
| 80% OR MORE TO LESS THAN 90% | 8 |
| 20% OR MORE TO LESS THAN 30% | 2 |
| 10% OR MORE TO LESS THAN 20% | 1 |
| LESS THAN 10% | 0 |

144

| IMAGING MENU | PREVIOUS NUM.I.F. | CURRENT NUM.I.F. | IN. OR DE. | INCREASING RATE | VARIABLE Z1 | VARIABLE Z2 | VARIABLE Z3 |
|---|---|---|---|---|---|---|---|
| C.P./U.I.P./F | 15 | 40 | 25 | 167% | 10 | 10 |  |
| C.P./U.I.P./R | 30 | 40 | 10 | 33% | 3 | 3 |  |
| A.P./U.I.P./F | 5 | 9 | 4 | 80% | 8 |  | 5 |
| A.P./U.I.P./R | 36 | 25 | -11 | -31% | 0 |  | 5 |

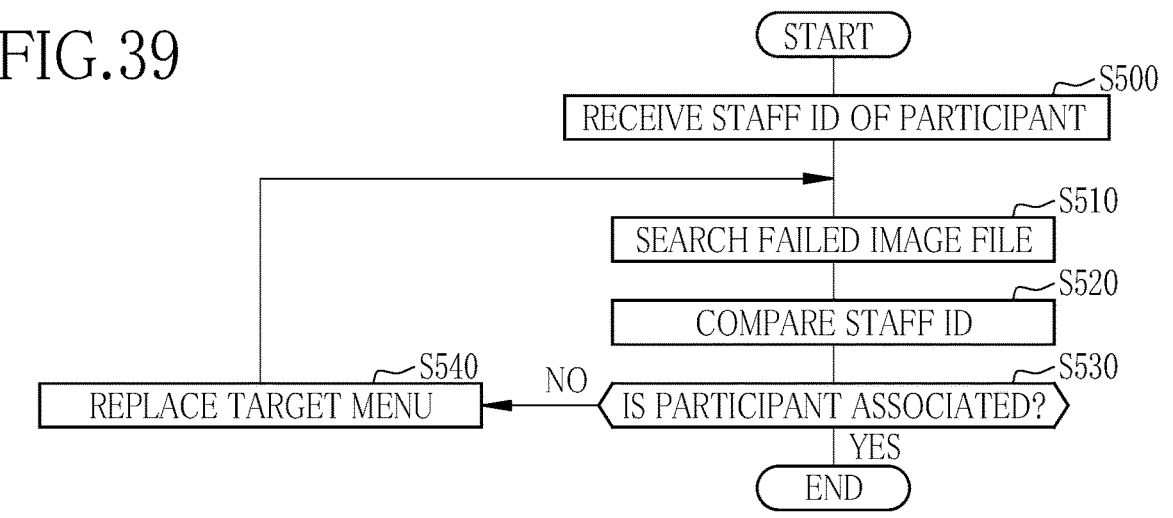

```
                              ( START )
                                  │
                    ┌─────────────────────────────────┐ ⌐S500
                    │ RECEIVE STAFF ID OF PARTICIPANT  │
                    └─────────────────────────────────┘
                                  │
                                  │             ⌐S510
                        ┌──────────────────────────┐
                        │ SEARCH FAILED IMAGE FILE  │
                        └──────────────────────────┘
                                  │             ⌐S520
                        ┌──────────────────────────┐
                        │    COMPARE STAFF ID       │
                        └──────────────────────────┘
         ⌐S540                   │       ⌐S530
┌──────────────────────┐  NO  ╱─────────────────────────╲
│ REPLACE TARGET MENU   │◄────┤ IS PARTICIPANT ASSOCIATED? ├
└──────────────────────┘      ╲─────────────────────────╱
                                      │ YES
                                  ( END )
```

FIG.40

|  | FIRST INDEX VALUE | ALLOCATION RATE | NUMBER OF CONSIDERATION IMAGES TO BE EXTRACTED |
|---|---|---|---|
| TARGET MENU 1 | 100 | 50% | 50 |
| TARGET MENU 2 | 70 | 35% | 35 |
| TARGET MENU 3 | 30 | 15% | 15 |

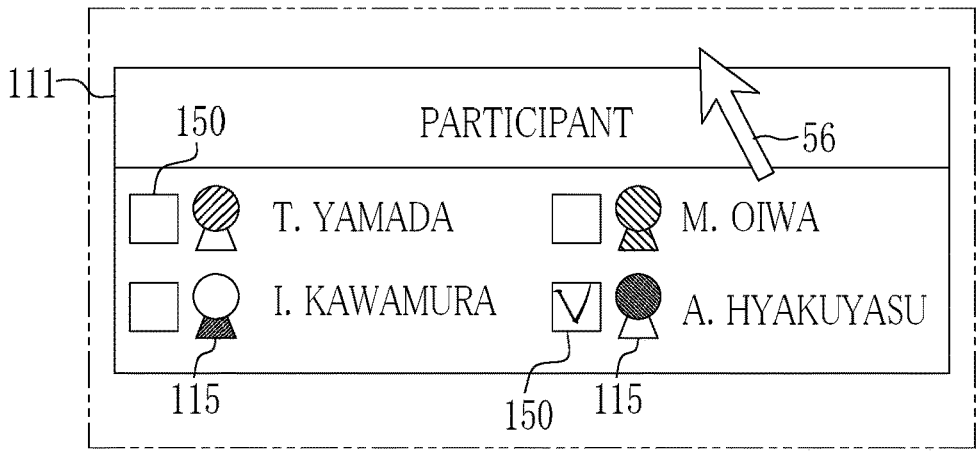

FAILED IMAGE MANAGEMENT APPARATUS, OPERATION METHOD OF FAILED IMAGE MANAGEMENT APPARATUS, AND FAILED IMAGE MANAGEMENT SYSTEM

CROSS-REFERENCE TO RELATED APPLICATIONS

The present application is a continuation of U.S. application Ser. No. 17/158,45, filed Jan. 26, 2021, which is a continuation of U.S. application Ser. No. 15/080,744 filed Mar. 25, 2016, which claims priority under 35 U.S.C. § 119 to Japanese Patent Application No. 2015-067015, filed Mar. 27, 2015 and Japanese Patent Application No. 2015-067016, filed Mar. 27, 2015. The above applications are hereby expressly incorporated by reference, in its entirety, into the present application.

BACKGROUND OF THE INVENTION

1. Field of the Invention

The present invention relates to a failed image management apparatus, an operation method of the failed image management apparatus, and a failed image management system.

2. Description Related to the Prior Art

In medical practice, medical images are captured with use of various types of imaging systems. For example, radiographic images are captured with use of a radiation imaging system, and MRI images are captured with use of a MRI (Magnetic Resonance Imaging) system. In the case of capturing such medical images, a medical staff member such as a doctor and a radiation technologist sets an imaging menu through a console of an imaging system. Imaging conditions are preliminarily associated with the imaging menu. The imaging conditions are adjusted finely in accordance with a body type or the like of a patient by a medical staff member, and set in an imaging system.

When a radiographic image is captured with use of the radiation imaging system, for example, one set including a body part to be imaged such as a cephalic part and a chest part, an imaging posture such as an upright imaging posture, a supine imaging posture, and sitting imaging posture, and an imaging direction such as a front direction and a rear direction is set as an imaging menu. Additionally, a tube voltage and a tube current to be applied to a radiation source for irradiating radiation toward a patient and an irradiation time of the radiation are set as the imaging conditions.

In the case of capturing a medical image, imaging failure occurs due to an error in positioning a patient, body motion of a patient, an error in setting imaging conditions, or the like, in some cases. The medical image captured in such a case is hereinafter referred to as a failed image, and the failed image is useful information in considering improvement on the image capturing for a medical staff member.

In Japanese Patent Laid-Open Publication No. 2006-218139, a failed image management apparatus for managing failed images is proposed. According to Japanese Patent Laid-Open Publication No. 2006-218139, the failed image management apparatus stores a failed image and an imaging menu associated with each other, and delivers a failed image corresponding to a designated imaging menu, which is designated by a medical staff member on a client terminal, to the client terminal. The client terminal displays a failed image delivered from the failed image management apparatus on a display panel. Thereby, the failed image is viewed by a medical staff member.

The purpose for viewing a failed image and considering improvement on the image capturing for a medical staff member is to improve his/her imaging skill and decrease a frequency of imaging failure or suppress increase in the frequency of imaging failure. Therefore, the failed image to be viewed by a medical staff member need to be associated with an imaging menu in which the frequency of imaging failure or an increasing rate of the frequency of imaging failure is relatively high. To that end, it is necessary for the medical staff member to extract and designate an imaging menu in which the frequency of imaging failure or the increasing rate of the frequency of imaging failure is relatively high.

In order to extract and designate an imaging menu in which the frequency of imaging failure or the increasing rate of the frequency of imaging failure is relatively high, the medical staff member need to know exactly an imaging failure state of each imaging menu. However, it imposes a heavy burden on a busy medical staff member to know exactly an imaging failure state of each imaging menu and extract and designate an imaging menu in which the frequency of imaging failure or the increasing rate of the frequency of imaging failure is relatively high.

The frequency of imaging failure is represented by any one of the number of times of occurrence of imaging failure and the rate of the number of times of occurrence of imaging failure with respect to the total number of times of imaging (hereinafter referred to as rate of occurrence of imaging failure). However, any one of the number of times of occurrence of imaging failure and the rate of occurrence of imaging failure is insufficient to know exactly the imaging failure state because of the following reason. For example, in both of an imaging menu in which the total number of times of imaging (abbreviated as T.NUM.I in the drawings) is 100 and the number of times of occurrence of imaging failure is 20 and an imaging menu in which the total number of times of imaging is 5 and the number of times of occurrence of imaging failure is 1, the rate of occurrence of imaging failure is 20%, namely, the same. Therefore, only the rate of occurrence of imaging failure is insufficient to judge whether or not the imaging failure state is proper. Although the imaging menu in which the total number of times of imaging is 100 and the number of times of occurrence of imaging failure is 20 has a statistical reliability higher than that of the imaging menu in which the total number of times of imaging is 5 and the number of times of occurrence of imaging failure is 1, the two imaging menus are treated the same due to the same rate of occurrence of imaging failure.

In the case where it is impossible to know exactly the imaging failure state of each imaging menu, there is a fear that an imaging menu in which the frequency of imaging failure or the increasing rate of the frequency of imaging failure is relatively low is extracted and designated. In such a case, the possibility of decreasing the frequency of imaging failure or the possibility of suppressing the increase in the frequency of imaging failure is low even by considering improvement on the image capturing. Therefore, the consideration is all in vain and results in waste of precious time of the medical staff members.

SUMMARY OF THE INVENTION

In view of the foregoing problems, an object of the present invention is to provide a failed image management apparatus which enables efficient consideration for improvement in image capturing, and further enables consideration for reliably decreasing frequency of imaging failure or consideration for reliably suppressing increase in the frequency of imaging failure, an operation method of the failed image management apparatus, and a failed image management system.

In order to achieve the above and other objects and advantages of the present invention, a failed image management apparatus of the present invention includes a first calculator and a first extractor. The first calculator calculates a first index value which quantitatively indicates an imaging failure state based on each imaging menu associated with a plurality of medical images containing failed images obtained as a result of failure in image capturing. The first calculator calculates the first index value using a first calculation formula having at least a variable based on the number of times of occurrence of imaging failure for each imaging menu and a variable based on a rate of occurrence of imaging failure for each imaging menu, or calculates the first index value using a first calculation formula having at least a variable based on an increasing rate of frequency of imaging failure for each imaging menu. The first extractor automatically extracts a target menu which is the imaging menu as a target to be subject to consideration for the purpose of preventing occurrence of imaging failure based on the first index value.

Preferably, the medical image is also associated with information regarding a medical staff member who performed the image capturing, and a participant as the medical staff member who attends the consideration is designated.

Preferably, the first calculation formula also has a variable based on the number of times of occurrence of imaging failure for each imaging menu for each participant and a variable based on the rate of occurrence of imaging failure for each imaging menu for each participant, in the case where the first index value is calculated using the first calculation formula having at least the variable based on the number of times of occurrence of imaging failure for each imaging menu and the variable based on the rate of occurrence of imaging failure for each imaging menu.

Preferably, the medical image is also associated with information regarding an imaging order for instructing a medical staff member to perform the image capturing. It is preferable that the first calculation formula also has a variable based on the number of times of occurrence of imaging failure for each imaging menu in the image capturing corresponding to the same imaging order, in the case where the first index value is calculated using the first calculation formula having at least the variable based on the number of times of occurrence of imaging failure for each imaging menu and the variable based on the rate of occurrence of imaging failure for each imaging menu.

Preferably, the medical image is also associated with information regarding a patient as a target for the image capturing. It is preferable that the first calculation formula also has a variable based on the number of times of occurrence of imaging failure for each imaging menu in the image capturing corresponding to the same patient, in the case where the first index value is calculated using the first calculation formula having at least the variable based on the number of times of occurrence of imaging failure for each imaging menu and the variable based on the rate of occurrence of imaging failure for each imaging menu.

It is preferable that the first calculation formula also has a variable based on the increasing rate of frequency of imaging failure of the target menu extracted at a previous consideration, in the case where the first index value is calculated using the first calculation formula having at least the variable based on the increasing rate of frequency of imaging failure for each imaging menu.

Preferably, the medical image is also associated with information regarding a medical staff member who performed the image capturing, and a participant as the medical staff member who attends the consideration is designated. It is preferable that the first calculation formula also has a variable based on whether or not a participant, who attended a previous consideration and was designated to attend a current consideration, failed in the image capturing corresponding the target menu extracted at the previous consideration, in the case where the first index value is calculated using the first calculation formula having at least the variable based on the increasing rate of frequency of imaging failure for each imaging menu.

Preferably, the medical image is also associated with information regarding date and time of the image capturing, and a calculation target period, as a period in which the medical image having the first index value to be calculated by the first extractor is captured, is designated.

Preferably, the failed image management apparatus further includes a second extractor for extracting a consideration image that is the failed image associated with the target menu among a plurality of the failed images.

Preferably, the failed image management apparatus further includes a second calculator for calculating a second index value which quantitatively indicates a degree of priority of the consideration image to be viewed. Preferably, the medical image is also associated with information regarding a medical staff member who performed the image capturing, and a participant as the medical staff member who attends the consideration is designated. The second calculator preferably calculates the second index value using a second calculation formula having at least a variable based on whether or not the failed image as the consideration image is associated with the participant. The second extractor preferably determines the failed image as the consideration image based on the second index value.

Preferably, the medical image is also associated with information regarding the medical staff member who performed the image capturing, and a participant as the medical staff member who attends the consideration is designated. Preferably, the second extractor replaces the target menu with another target menu and extracts the consideration image again, in the case where there is no consideration image associated with the participant among the consideration images extracted based on the target menu. Replacement of the target menus and re-extraction of the consideration images are preferably repeated until the consideration image associated with the participant is extracted.

It is preferable that the second extractor increases the number of failed images to be extracted as the consideration images, as the imaging failure state indicated by the first index value of the target menu with which the failed image is associated is poorer, in the case where there are a plurality of the target menus extracted by the first extractor.

The number of consideration images to be extracted by the second extractor is preferably designated.

It is preferable that the medical image is also associated with information regarding the date and time of the image capturing, and an extraction target period, as a period in which the failed image to be extracted as the consideration image by the second extractor is captured, is designated.

Preferably, the failed image management apparatus further includes screen output controller for controlling an output of a display screen for displaying the target menu and a second extractor for extracting a consideration image that is the failed image associated with the target menu among a plurality of the failed images, and the consideration image is also displayed on the display screen. Preferably, the failed image management apparatus further includes a second calculator for calculating a second index value which quantitatively indicates a degree of priority of the consideration image to be viewed. In the case where there are a plurality of the consideration images extracted by the second extractor, it is preferable that the consideration images arranged in accordance with the second index value are displayed on the display screen, or the consideration images each having a display size and a display position in accordance with the second index value are displayed on the display screen.

An operation method of a failed image management apparatus of the present invention includes a calculation step and an extraction step. The calculation step calculates an index value which quantitatively indicates an imaging failure state based on each imaging menu associated with a plurality of medical images containing failed images obtained as a result of failure in image capturing. The calculation step calculates the index value using a calculation formula having at least a variable based on the number of times of occurrence of imaging failure for each imaging menu and a variable based on a rate of occurrence of imaging failure for each imaging menu, or calculates the index value using a calculation formula having at least a variable based on an increasing rate of frequency of imaging failure for each imaging menu. The extraction step automatically extracts a target menu which is the imaging menu as a target to be subject to consideration for the purpose of preventing occurrence of imaging failure based on the index value.

A failed image management system including a failed image management apparatus of the present invention includes a calculator and an extractor. The calculator calculates an index value which quantitatively indicates an imaging failure state based on each imaging menu associated with a plurality of medical images containing failed images obtained as a result of failure in image capturing. The calculator calculates the index value using a calculation formula having at least a variable based on the number of times of occurrence of imaging failure for each imaging menu and a variable based on a rate of occurrence of imaging failure for each imaging menu, or calculates the index value using a calculation formula having at least a variable based on an increasing rate of frequency of imaging failure for each imaging menu. The extractor automatically extracts a target menu which is the imaging menu as a target to be subject to consideration for the purpose of preventing occurrence of imaging failure based on the index value.

According to the present invention, the index value is calculated using the calculation formula having at least the variable based on the number of times of occurrence of imaging failure for each imaging menu and the variable based on the rate of occurrence of imaging failure for each imaging menu. Alternatively, the index value is calculated using the calculation formula having at least the variable based on the increasing rate of frequency of imaging failure for each imaging menu. Based on the index value thus calculated, the target menu which is the imaging menu as the target to be subject to consideration for the purpose of preventing occurrence of imaging failure, is automatically extracted. Thereby, it is possible to provide the failed image management apparatus which enables efficient consideration for improvement in image capturing, and further enables consideration for reliably decreasing frequency of imaging failure or consideration for reliably suppressing increase in the frequency of imaging failure, the operation method of the failed image management apparatus, and the failed image management system.

BRIEF DESCRIPTION OF THE DRAWINGS

The above objects and advantages of the present invention will become more apparent from the following detailed description when read in connection with the accompanying drawings, in which:

FIG. 2 is an explanatory view illustrating a flow of radiography from a step at which an imaging order is acquired to a step at which an imaging menu and imaging conditions are set;

FIG. 4 illustrates contents of the image file;

FIG. 9 illustrates contents of designation information contained in a delivery request;

FIG. 14 illustrates derivation results of variables based on the number of times of occurrence of imaging failure (abbreviated as NUM.I.F. in the drawings) for each imaging menu for each participant and variables based on the rate of occurrence of imaging failure (abbreviated as R.I.F. in the drawings) for each imaging menu for each participant;

FIG. 32 illustrates contents of conference history information;

FIG. 39 illustrates a flow of processing performed by the second extractor according to a third embodiment;

FIG. 40 illustrates an allocation rate of the consideration images and the number of consideration images to be extracted for each target menu according to a forth embodiment;

FIG. 41 illustrates another example of the conference screen;

DETAILED DESCRIPTION OF THE REFERRAL EMBODIMENT(S) OF THE PRESENT INVENTION

First Embodiment

Figure 1:
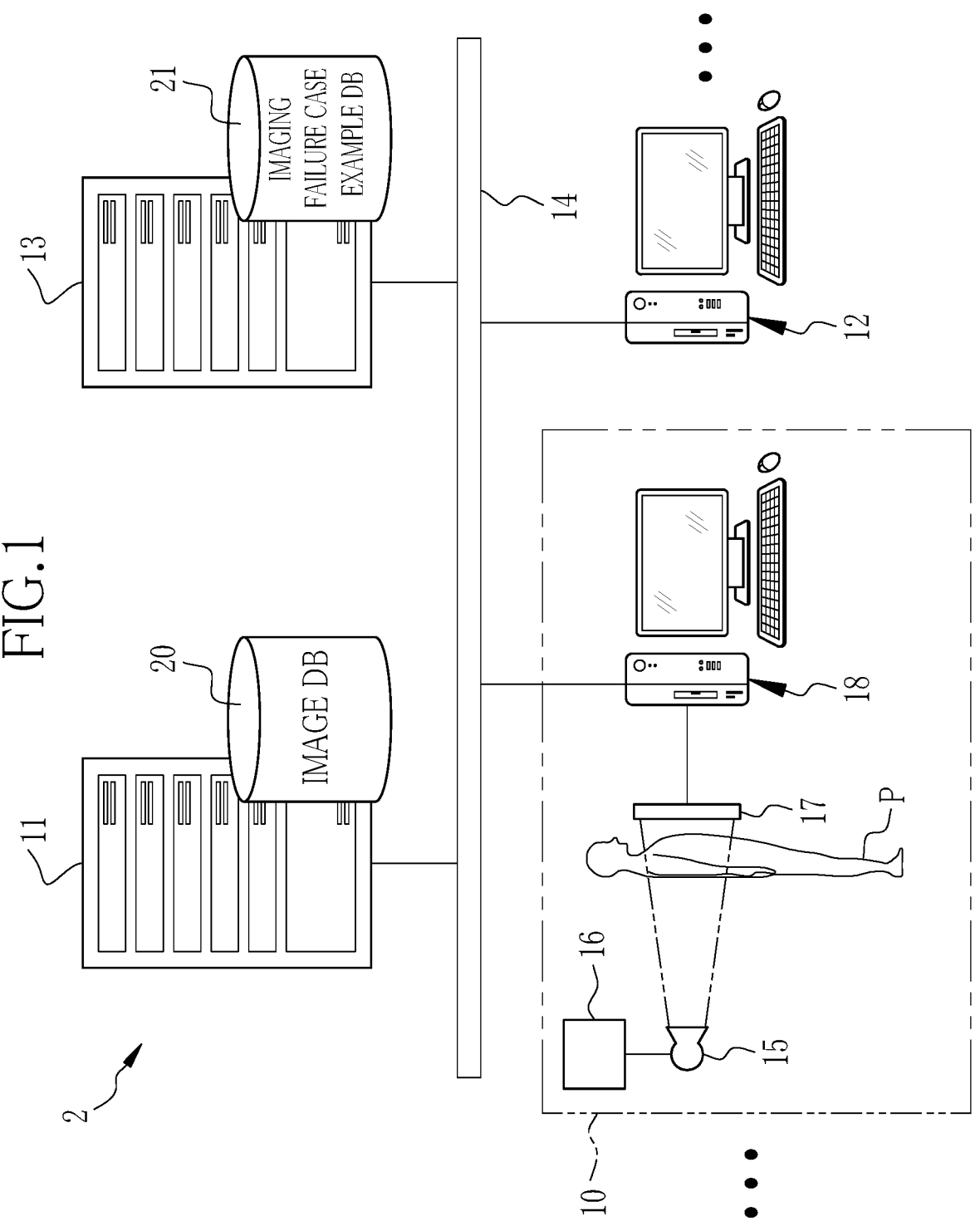
FIG. 1 illustrates a medical information system.

In FIG. 1, a medical information system 2 includes a radiation imaging system 10, a PACS (Picture Archiving and Communication System) 11, a client terminal 12, and a failed image management server 13 corresponding to a failed image management apparatus, which are connected to one another through a network 14 such as a LAN (Local Area Network) provided in a medical facility.

As well known, the radiation imaging system 10 includes a radiation source 15 for irradiating radiation such as X-rays toward a patient P as an imaging target, a radiation source controller 16 for controlling an operation of the radiation source in accordance with an imaging condition, a radiographic image detector 17, and a console 18 for controlling an operation of the radiographic image detector 17. The imaging condition consists of a tube voltage and a tube current to be applied to the radiation source 15 and an irradiation time of the radiation. The radiographic image detector 17 receives the radiation having been irradiated from the radiation source 15 and having passed through the Patient P, and detects a radiographic image 26 (see FIG. 3) corresponding to a medical image. Incidentally, although one radiation imaging system 10 is depicted in FIG. 1, in fact, a plurality of the radiation imaging systems 10 are provided in each of a plurality of imaging rooms.

Each of the PACS 11, the client terminal 12, and the failed image management server 13 is composed of a computer (e.g., personal computer, server computer, workstation, or the like) installed with a control program (e.g., operating system) and various types of application programs.

The PACS 11 includes an image database (hereinafter abbreviated as DB) 20, in which a diagnostic image file (see FIG. 3) is stored in a retrievable manner. The PACS 11 stores and manages the diagnostic image file.

The failed image management server 13 includes an imaging failure case example DB 21, in which the diagnostic image file and the failed image file (see FIG. 3) are stored in a retrievable manner. The failed image management server 13 stores and manages the diagnostic image file and the failed image file.

The diagnostic image file is an image file created based on a diagnostic image, which is usable for diagnosis, among radiographic images 26 captured by the radiation imaging system 10. The failed image file is an image file created based on a failed image, which is unsuccessfully captured, among the radiographic images 26 captured by the radiation imaging system 10. Note that, the cause of the failure in image capturing is an error in positioning the patient P, body motion of the patient P, an error in setting the imaging condition, or the like.

The client terminal 12 is operated by a medical staff member at a conference for considering improvement on the image capturing at which a plurality of medical staff members such as a radiation technologist in charge of the image capturing gather. The conference is periodically held, for example, every one month. Incidentally, although one client terminal 12 is depicted in FIG. 1, a plurality of the client terminals 12 may be provided for a plurality of medical staff members on one-to-one basis.

In FIG. 2, the console 18 receives an imaging order for instructing a medical staff member to perform image capturing. The imaging order is issued using an electronic medical chart by a doctor belonging to a diagnosis and treatment department such as an internal medicine department (abbreviated as "I.M. DEP." in the drawing) and a trauma department, and transmitted to the console 18 through a RIS (Radiology Information System, not shown in the drawing). The console 18 represents the contents of an imaging menu to the medical staff member. Incidentally, instead of using the system such as the RIS, the imaging order in a printed paper version is passed from the doctor belonging to the diagnosis and treatment department to the medical staff member in some cases. In this case, the imaging order is manually inputted to the console 18 by the medical staff member.

The imaging order contains items such as "order ID (Identification data)", "department as requestor", "staff ID", "patient ID", and "body part to be imaged/imaging posture/ imaging direction". The order ID consists of symbols and numbers, for identifying an individual imaging order, and is automatically assigned by the RIS. The name of the diagnosis and treatment department, which issued the imaging order, is inputted to the item "department as requestor". The staff ID of the doctor as the requestor of the image capturing, who issued the imaging order, is inputted to the item "staff ID". The patient ID of the patient P as the imaging target is inputted to the item "patient ID". The staff ID consists of symbols and numbers, for identifying an individual medical staff member such as a doctor and a radiation technologist. The patient ID consists of symbols and numbers, for identifying an individual patient.

The body part to be imaged, the imaging posture, and the imaging direction, designated by the doctor who issued the imaging order, are inputted to the item "body part to be imaged/imaging posture/imaging direction". The body part to be imaged includes cephalic part, cervical spine, chest part, abdominal part, hand, finger, elbow, and knee of a human body. The imaging posture is the posture of the patient P, such as an upright imaging posture, a supine imaging posture, and a sitting imaging posture. The imaging direction is an orientation of the patient P toward the radiation, such as a front direction, aside direction, and a rear direction. In an example shown in FIG. 2, the chest part is designated as the body part to be imaged, the upright imaging posture is designated as the imaging posture, and the front direction is designated as the imaging direction. Note that, in addition to the above items, the date and time on which the RIS receives the imaging order, the purpose of the image capturing such as follow-up after surgery and response evaluation of a curative drug, a message from the doctor belonging to the diagnosis and treatment department to the radiation technologist, and the like may be added as the items.

In some cases, one imaging order is issued for one patient, and in other cases, a plurality of the imaging orders are issued for one patient at the same time. In the case where a plurality of the imaging orders are issued for one patient at the same time, an identification code for identifying the one patient is assigned to the order ID of each of a plurality of the imaging orders.

A menu/condition table 25 is stored in the console 18. The imaging menu including the body part to be imaged, the imaging posture, and the imaging direction as one set, and the imaging condition corresponding to the imaging menu are associated with each other and registered in the menu/ condition table 25. The console 18 represents the contents of the menu/condition table 25 to the medical staff member such that the medical staff member can set the imaging menu. Incidentally, the imaging menu including the body part to be imaged and the imaging direction as one set, with the imaging posture being excluded from the imaging menu, and the imaging menu adapted to special imaging such as tomosynthesis imaging and long time-scale imaging may be provided.

The medical staff member confirms the contents of the imaging order using the console 18, and selects and sets the imaging menu including the body part to be imaged, the imaging posture, and the imaging direction designated by the imaging order. Then, the medical staff member manually sets the imaging condition which is the same as the imaging condition corresponding to the set imaging menu, or the imaging condition obtained by finely adjusting the imaging condition corresponding to the set imaging menu in accordance with a body type or the like of the patient P, to the radiation source controller 16.

After setting the imaging condition, the medical staff performs the positioning of each of the radiation source 15, the radiographic image detector 17, and the patient P to a desired position. Thereafter, the medical staff member drives the radiation source 15, so as to irradiate radiation to the patient P. The radiation having passed through the patient P is irradiated to the radiographic image detector 17, and thus the radiographic image detector 17 detects the radiographic image 26.

Figure 3:
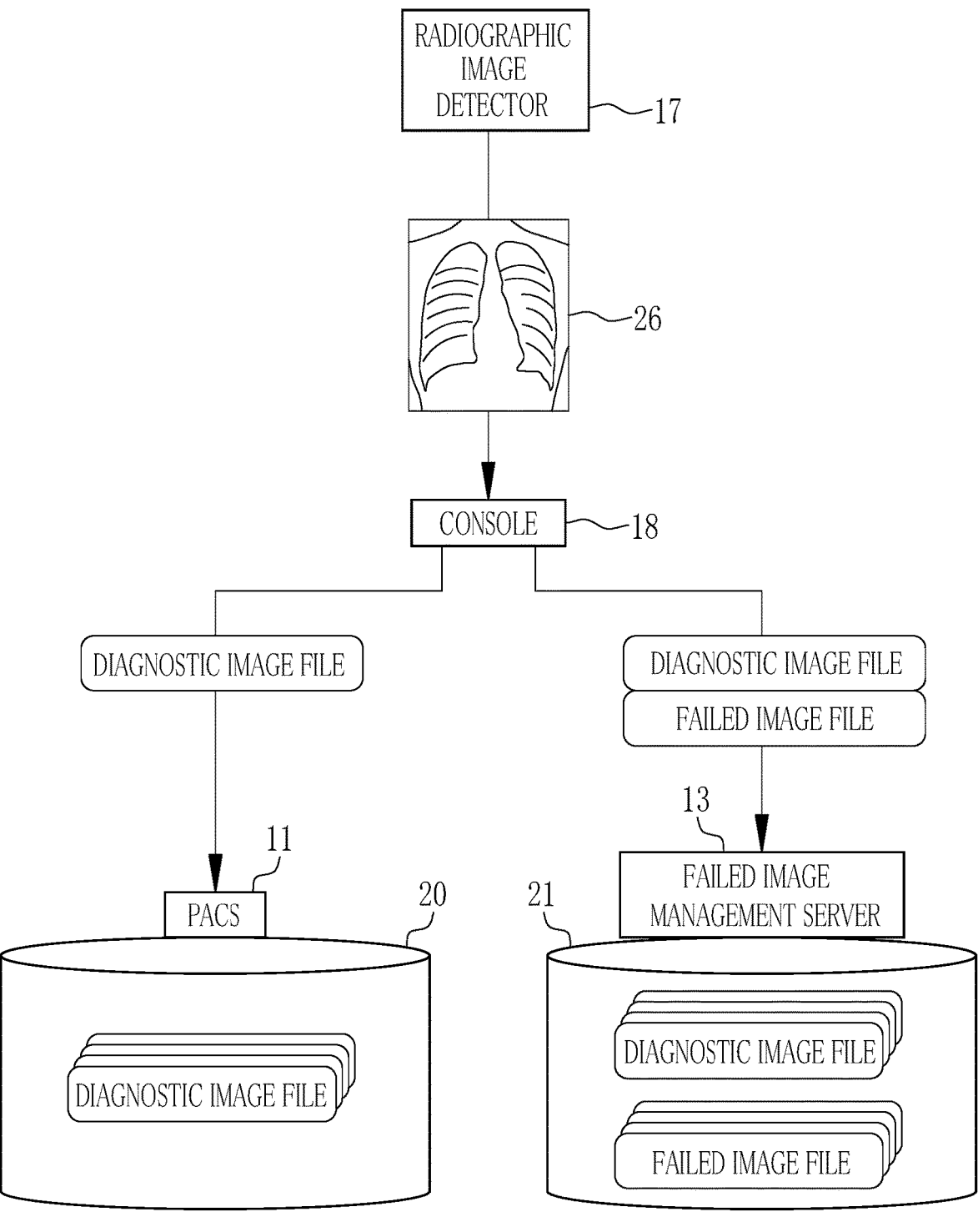
FIG. 3 is an explanatory view illustrating a flow of radiography from a step at which a radiographic image is detected to a step at which an image file is transmitted to a PACS and a failed image management server.

In FIG. 3, the radiographic image detector 17 transmits the radiographic image 26 to the console 18. The console 18 displays the radiographic image 26 to the medical staff member. The medical staff member judges whether the radiographic image 26 displayed by the console 18 is the diagnostic image or the failed image, and inputs the judgment result to the console 18. A point of time when the medical staff member judges the radiographic image 26 as the diagnostic image corresponds to a sign of the completion of the image capturing for one imaging order.

The console 18 creates an image file in which the radiographic image 26 is associated with the imaging menu set at the time of capturing the radiographic image 26 and other accompanying information. As described above, there are two types of image files, namely, there are the diagnostic image file based the diagnostic image and the failed image file based the failed image. The console 18 transmits the diagnostic image file to the PACS 11, and transmits the diagnostic image file and the failed image file to the failed image management server 13. Note that, the timing of transmitting each of the image files by the console 18 may be just after each of the image files is created. As the failed image file is not necessary for diagnosis, the failed image file after being created may be stocked once and transmitted at a predetermined timing. For example, when the day's work is completed and the console 18 is shut down, the failed image files may be transmitted at a time.

In FIG. 4, the image file is in a file format compatible with DICOM (Digital Imaging and Communication in Medicine) standard, for example. The image file includes an accompanying information storage 27 in which accompanying information is stored and an image storage 28 in which the radiographic image 26 is stored.

In the accompanying information storage 27, there are stored items "file ID", "date and time of imaging", "patient ID", "patient name", "gender", "date of birth", "age", "body height (unit: cm)", "body weight (unit: kg)", "inpatient/ outpatient classification (abbreviated as "IP/OP CLASSIFI-CATION" in the drawings)", "order ID", "imaging menu", "tube voltage (unit: kV)", "tube current (unit: mA)", "irradiation time (unit: ms)", "staff ID", "imaging room", and "imaging failure flag".

The file ID consists of symbols and numbers for identifying each image file, and is automatically assigned by the console 18 at the time of creating an image file. The date and time of imaging is literally the date and time when the image capturing is performed, and automatically assigned by the radiographic image detector 17 at the time of detecting the radiographic image 26.

The patient ID and the like of the patient P as the imaging target are respectively inputted to the items "patient ID", "patient name", "gender", "date of birth", "age", "body height", "body weight", and "inpatient/outpatient classification". The information regarding the patient P can be obtained from HIS (Hospital Information System, not shown in the drawing), for example. Incidentally, in addition to the above items, an item "body type index" such as BMI (Body Mass Index) calculated from the body height and the body weight may be added.

The order ID of the imaging order of the imaging target is inputted to the item "order ID". Until the medical staff member judges the radiographic image 26 as the diagnostic image and the sign of the completion of the image capturing is issued, the same order ID is inputted to the item "order ID". Namely, in the case where the image capturing fails and the failed image is captured, at least one of the failed image files in each of which the same order ID is inputted and one diagnostic image file are created. The number of the failed image files in each of which the same order ID is inputted represents the number of times of occurrence of imaging failure corresponding to the order ID.

The imaging menu set by the medical staff member is set to the item "imaging menu". The tube voltage, tube current, and irradiation time set to the radiation source controller 16 by the medical staff member are respectively inputted to the items "tube voltage", "tube current", and "irradiation time". The staff ID of the medical staff member who performed the image capturing (radiographer) is inputted to the item "staff ID". The imaging room in which the image capturing was performed is inputted to the item "imaging room".

An imaging failure flag is used to distinguish the image file between the diagnostic image file and the failed image file. In the case of the diagnostic image file, "0" is inputted to the item "imaging failure flag", and in the case of the failed image file, "1" is inputted to the item "imaging failure flag".

Since "1" is inputted to the item "imaging failure flag" in FIG. 4, the image file shown in FIG. 4 is the failed image file. The radiographic image 26 stored in the image storage 28 is the failed image. As shown by the botted lines, positional displacement due to a positioning error of the patient P, image blur due to body motion of the patient P, excessive concentration or insufficient concentration due to the setting error in the imaging condition, and the like appear.

Figure 5:
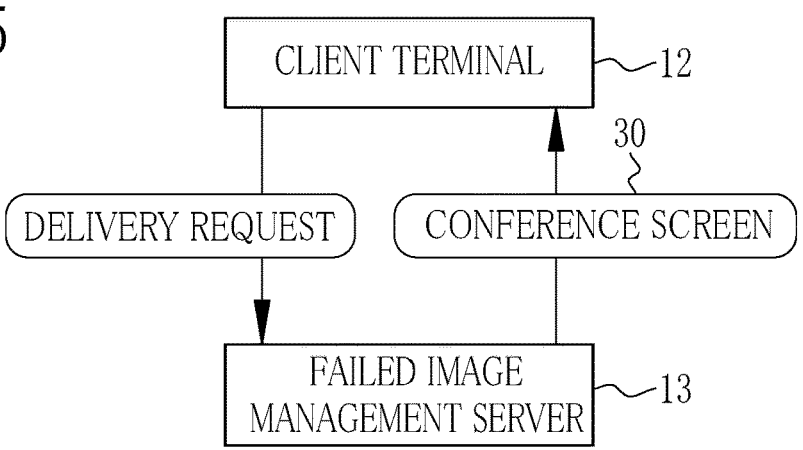
FIG. 5 illustrates various types of information transmitted/received between a client terminal and the failed image management server.

In FIG. 5, the client terminal 12 outputs the delivery request to the failed image management server 13. The failed image management server 13 receives the delivery request from the client terminal 12. The failed image management server 13 automatically extracts a target menu as the imaging menu to be considered at the conference, and a consideration image 26C (see FIG. 27) to be viewed by the medical staff members at the conference, in response to the delivery request. The failed image management server 13 generates a conference screen 30 (corresponding to display screen, also see FIG. 25 to FIG. 27) for displaying the target menu and the consideration image 26C, and outputs the conference screen 30 to the client terminal 12 as a requestor of the delivery request.

The failed image management server 13 outputs the conference screen 30 in the XML data format for web delivery, which is described by a markup language such as XML (Extensible Markup Language), for example. The client terminal 12 reproduces and displays the conference screen 30 on the web browser based on the XML data. Incidentally, instead of the XML, a data description language such as JSON (JavaScript (registered trademark) Object Notation) may be used.

Figure 6:
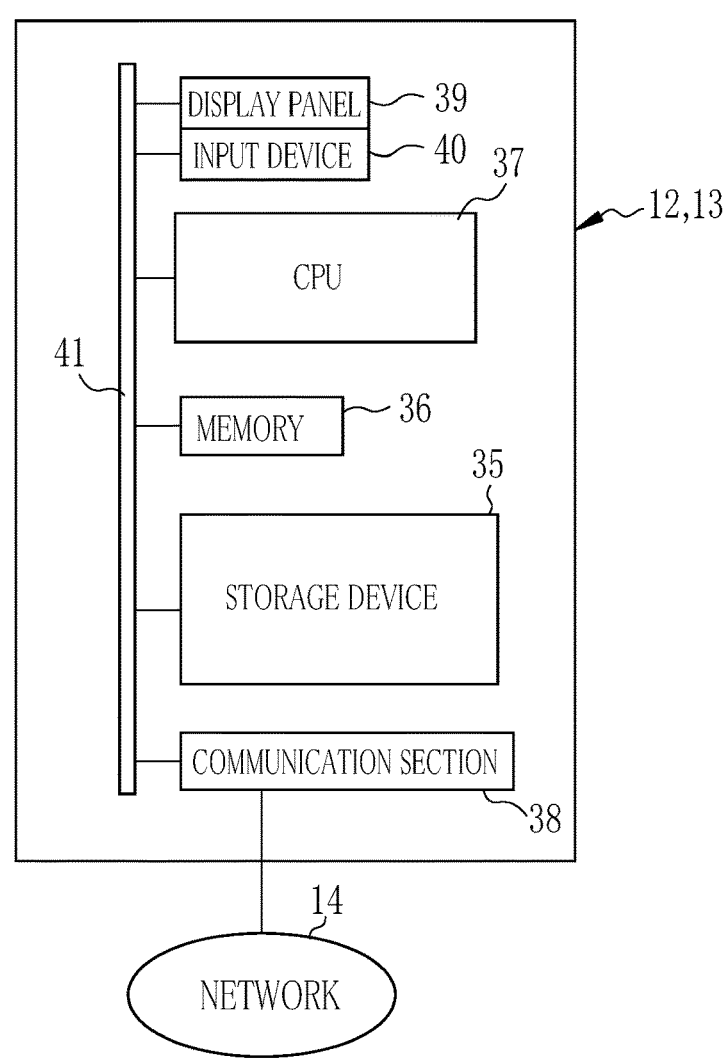
FIG. 6 is a block diagram illustrating a computer constituting the client terminal and the failed image management server.

In FIG. 6, the computer constituting the client terminal 12 and the computer constituting the failed image management server 13 have the same basic structure. Each of the computers includes a storage device 35, a memory 36, a CPU (Central Processing Unit) 37, a communication section 38, a display panel 39, and an input device 40, which are connected to one another through a data bus 41.

The storage device 35 is incorporated in the computer constituting the client terminal 12 or the like. Alternatively, the storage device 35 is a hard disk drive connected through a cable or a network, or a disk array composed of two or more connected hard disk drives. The storage device 35 stores a control program such as an operating system, various types of application programs, and display data of various types of operation screens associated with the programs.

The memory 36 is a working memory, which is used by the CPU 37 to execute processing. The CPU 37 loads the programs, which are stored in the storage device 35, into the memory 36, and executes the processing in accordance with the programs. Thereby, the CPU 37 centrally controls each section of the computer.

The communication section 38 is a network interface that controls transmissions of various types of information through the network 14. The display panel 39 displays various types of operation screens in accordance with the operation of the input device 40 such as a mouse and a keyboard. The operation screen is provided with an operation function using a GUI (Graphical User Interface). A computer, which constitutes the client terminal 12 or the like, receives the input of an operation command from the input device 40 through the operation screen.

Incidentally, in the descriptions below, a suffix "A" is attached to a numeral that denotes each component of the computer that constitutes the client terminal 12, and a suffix "B" is attached to a numeral that denotes each component of the computer that constitutes the failed image management server 13, for distinction.

Figure 7:
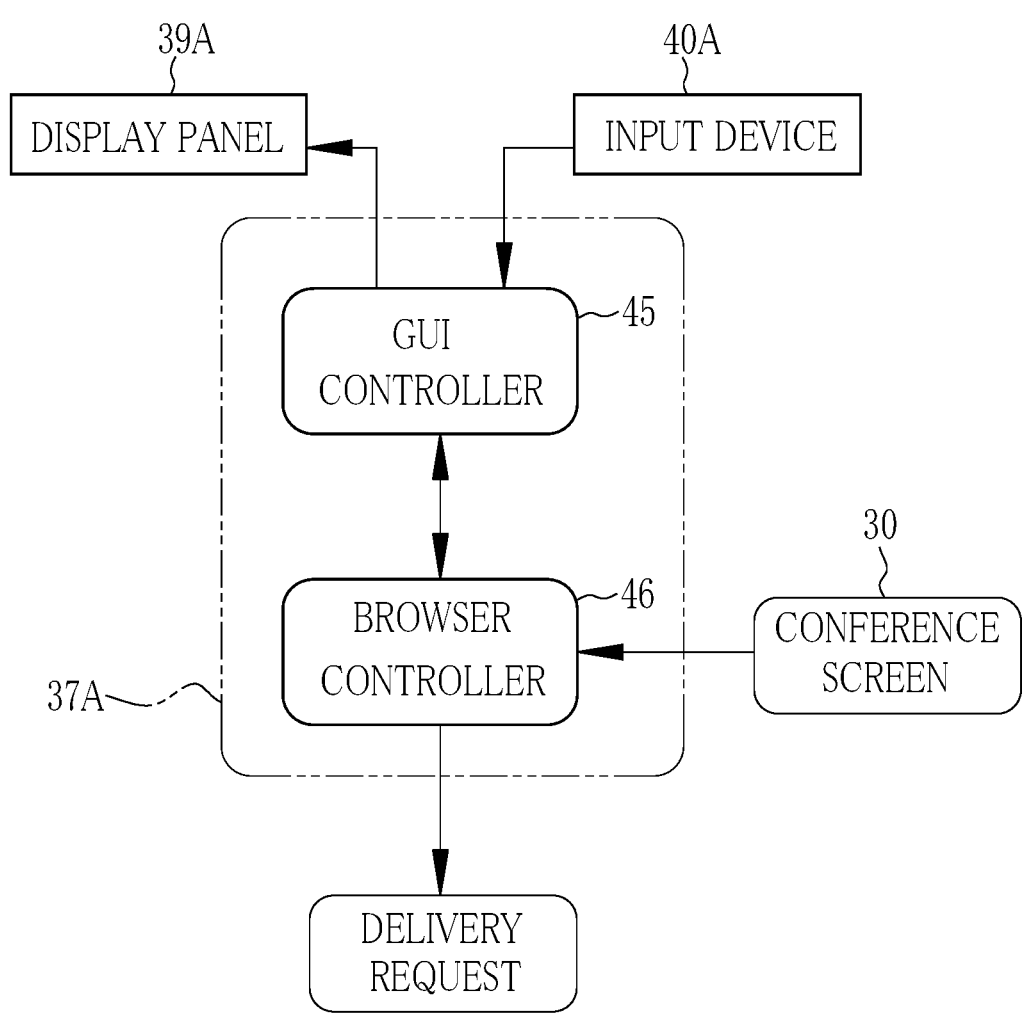
FIG. 7 is a block diagram illustrating a function of a CPU of the client terminal.

In FIG. 7, upon the startup of the web browser, a CPU 37A of the client terminal 12 works together with the memory 36, and thereby functions as a GUI controller 45 and a browser controller 46.

The GUI controller 45 displays various types of operation screens on the display panel 39A, and receives an operation command inputted using the input device 40A through various types of operation screens. The operation command is a command for delivering the conference screen 30 or the like. The GUI controller 45 outputs the received operation command to the browser controller 46.

The browser controller 46 controls the operation of the web browser. The browser controller 46 issues the delivery request to the failed image management server 13. Further, the browser controller 46 receives the XML data of the conference screen 30 from the failed image management server 13. The browser controller 46 reproduces the conference screen 30 to be displayed on the web browser based on the XML data, and outputs the conference screen 30 to the GUI controller 45. The GUI controller 45 displays the conference screen 30 on the display panel 39A.

Figure 8:
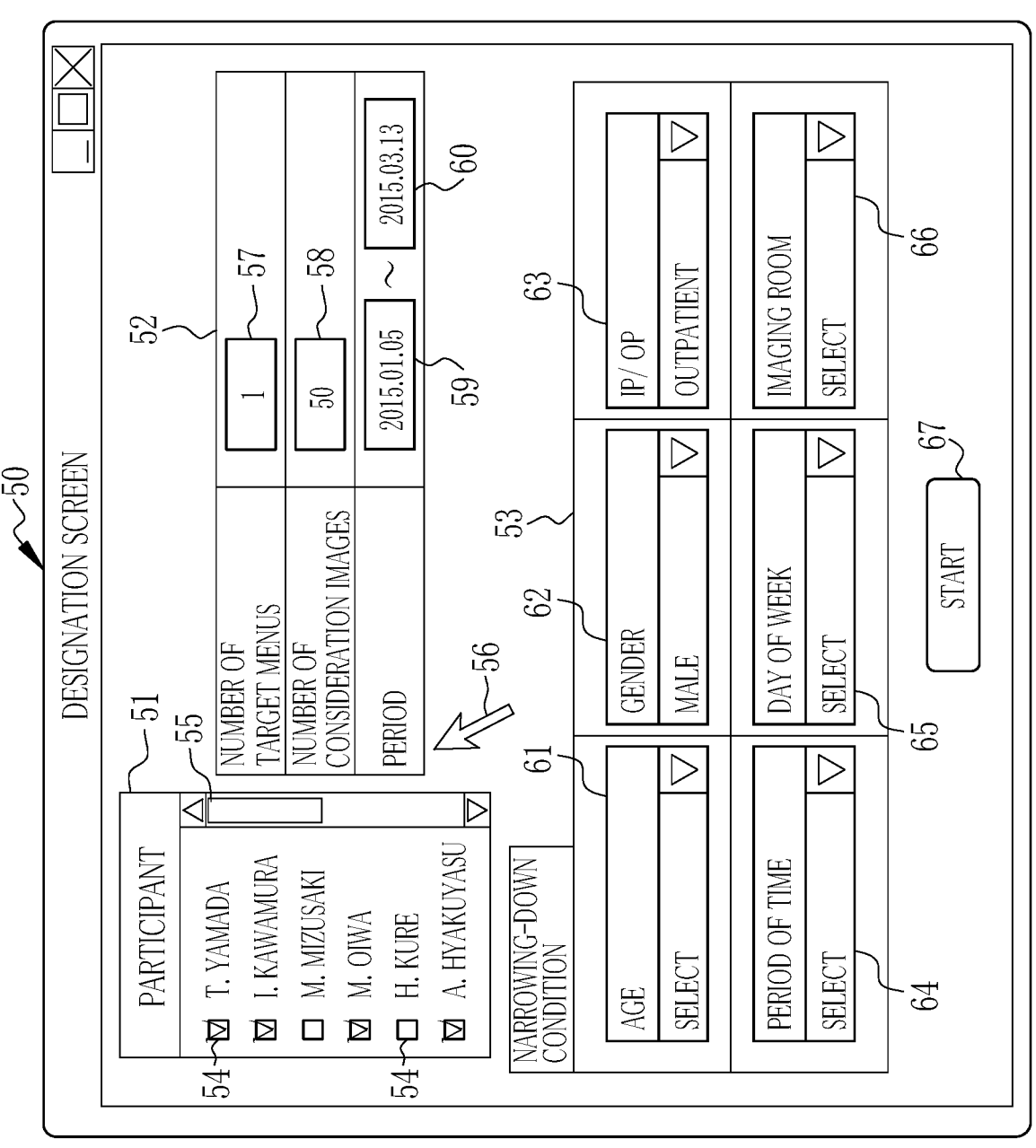
FIG. 8 illustrates a designation screen.

At the conference, the medical staff member accesses a site established by the failed image management server 13 on the web browser. Upon completion of the access to the site, a designation screen 50 as shown in FIG. 8 is displayed on the display panel 39A. The designation screen 50 is a screen for inputting a command for delivering the conference screen 30.

In FIG. 8, a designation screen 50 includes a participant selection region 51, an input region 52 for inputting the number of target menus, the number of consideration images, and a target period (hereinafter simply referred to as input region 52), and a narrowing-down condition selection region 53. The participant selection region 51 is a region for selecting medical staff members (participants) who attend the conference. The full name of each medical staff member is displayed in a participant selection region 51. Check boxes 54 for selecting the medical staff members as the participants, and a scroll bar 55 for displaying hidden full names of medical staff members and hidden check boxes are provided in the participant selection region 51. The check box 54 is selectable using a cursor 56, and a check mark is displayed in the check box 54 selected using the cursor 56.

The participants are displayed in the participant selection region 51 by acquiring the information regarding the staff ID from the item "staff ID" in each of the diagnostic image file and the failed image file stored in the imaging failure case example DB 21 and converting the acquired staff ID to the full name. Incidentally, a function for selecting all the medical staff members as the participants collectively and a function for selecting the participants for each group containing some of the medical staff members may be provided to the participant selection region 51.

The input region 52 is a region for inputting the number of target menus (abbreviated as NUM.T.M. in the drawings), the number of consideration images 26C, and the period. The period includes a calculation target period and an extraction target period. The calculation target period is a period in which the radiographic image 26 having the first index value to be calculated by a first calculator 72 (see FIG. 10) was captured. The extraction target period is a period in which the failed image to be extracted as the consideration image 26C by a second extractor 74 (see FIG. 10) was captured.

The item input region 52 is provided with an input box 57 for inputting the number of target menus, an input box 58 for inputting the number of consideration images 26C, and input boxes 59 and 60 for inputting the period. The numerical value indicating the number of target menus is inputted to the input box 57. The numerical value indicating the number of consideration images 26C is inputted to the input box 58. The starting date of the period is inputted to the input box 59, and the ending date of the period is inputted to the input box 60. Here, the calculation target period and the extraction target period are designated together using the input boxes 59 and 60. However, the calculation target period and the extraction target period may be designated separately by providing an input box dedicated for the calculation target period and an input box dedicated for the extraction target period.

The narrowing-down condition selection region 53 is a region for selecting the narrowing-down condition. The narrowing-down condition includes the age and gender of the patient, inpatient/outpatient classification, a period of time of the image capturing, a day of week of the image capturing, and the imaging room. The narrowing-down condition selection region 53 is provided with pull-down menus 61, 62, 63, 64, 65, and 66 each for selecting the narrowing-down condition. Incidentally, the narrowing-down condition may include the ranges of body height and body weight of the patient, and the range of the imaging condition such as the tube voltage.

At least one of the check boxes 54 in the participant selection region 51 is required to be selected. In contrast, the input of the number of target menus to the input box 57, the input of the number of consideration images 26C to the input box 58, and the input of the period to the input boxes 59 and 60 in the item input region 52 may be arbitrarily performed. As well, the selection of the pull-down menus 61 to 66 each for selecting the narrowing-down condition in the narrowing-down condition selection region 53 may be arbitrarily performed.

A start button 67 is disposed under the narrowing-down condition selection region 53. In response to selection of the start button 67 after the selection of at least one of the check boxes 54, the command for delivering the conference screen 30 is received by the GUI controller 45, and outputted to the browser controller 46.

In FIG. 8, as the participants, four participants, "Tadashi YAMADA", "Ichiro KAWAMURA", "Misaki OIWA", "Ayaka HYAKUYASU" are selected. (Each person's name is abbreviated as an initial in terms of space in the drawings but it is fully displayed without abbreviations in practice.) "1" is inputted to the input box 57, "50" is inputted to the input box 58, "2015.01.05" is inputted to the input box 59, and "2015.03.13" is inputted to the input box 60, respectively. Further, in FIG. 8, as the narrowing-down condition, gender "male" (abbreviated "M" in the drawings), inpatient/outpatient classification "outpatient" are respectively selected, by way of example.

The browser controller 46 generates designation information shown in FIG. 9 in response to the command for delivering the conference screen 30 from the GUI controller 45. The designation information includes items of the staff ID of the participant, the number of target menus, the number of consideration images, the period, and the narrowing-down condition. The information corresponding to the selected state and the inputted state in each of the regions 51 to 53 in the designation screen 50 is inputted to the items. The browser controller 46 issues the request for delivering the conference screen 30 containing the designation information.

FIG. 9 illustrates the designation information in which information corresponding to the selected state and the inputted state in the designation screen 50 shown in FIG. 8 is contained. Incidentally, the staff ID "R0001" inputted to the item of the staff ID corresponds to "Tadashi YAMADA", the staff ID "R0002" inputted to the item of the staff ID corresponds to "Ichiro KAWAMURA", the staff ID "R0005" inputted to the item of the staff ID corresponds to "Misaki OIWA", and the staff ID "R0008" inputted to the item of the staff ID corresponds to "Ayaka HYAKUYASU" as the participants.

Figure 10:
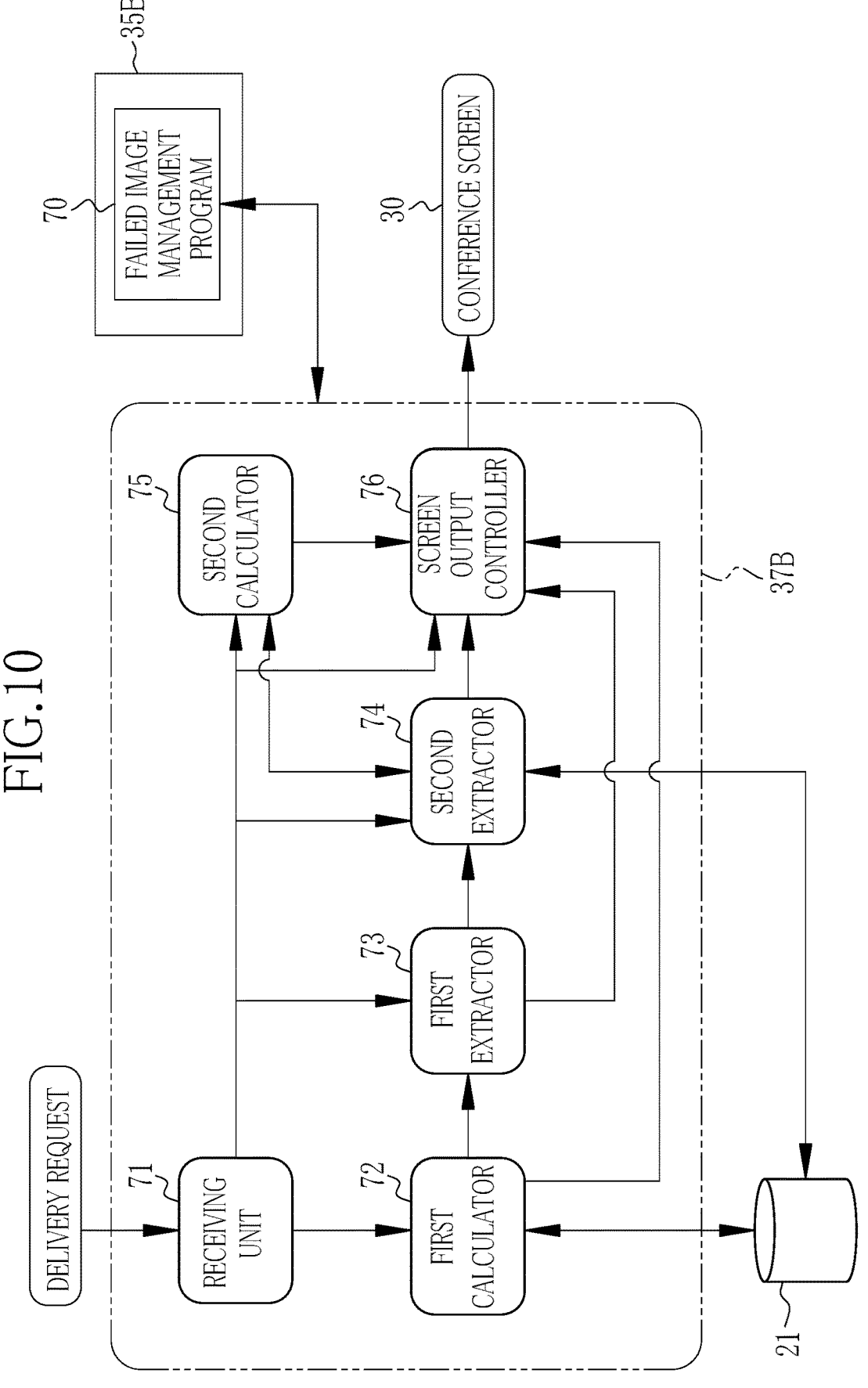
FIG. 10 is a block diagram illustrating a function of the CPU of the failed image management server.

As shown in FIG. 10, a failed image management program 70 is stored in a storage device 35B of the failed image management server 13. The failed image management program 70 is an application program for making the computer constituting the failed image management server 13 function as the failed image management apparatus. The failed image management program 70 corresponds to an operation program.

Upon the startup of the failed image management program. 70, the CPU 37B of the failed image management server 13 works together with the memory 36, such that the CPU 37B and the memory 36 function as a receiving unit 71, the first calculator 72, a first extractor 73, the second extractor 74, a second calculator 75, and a screen output controller 76.

The receiving unit 71 receives the delivery request from the client terminal 12. The receiving unit 71 outputs the information regarding the staff ID of the participant and the information regarding the period as the designation information contained in the delivery request to the first calculator 72, and outputs the information regarding the period as the designation information contained in the delivery request to the first extractor 73. Further, the receiving unit 71 outputs the information regarding the number of consideration images and the information regarding the extraction target period to the second extractor 74, and outputs the information regarding the staff ID of the participant and the information regarding the narrowing-down condition to the second calculator 75. Furthermore, the receiving unit 71 outputs the information regarding the staff ID of the participant to the screen output controller 76.

The first calculator 72 calculates the first index value quantitatively indicating the imaging failure state for each of the imaging menus based on the imaging menus inputted in the diagnostic image file and the failed image file stored in the imaging failure case example DB 21. The first extractor 73 automatically extracts the target menu based on the first index value.

The second extractor 74 extracts the failed image file, in which the target menu extracted by the first extractor 73 is inputted, from a plurality of the failed image files stored in the imaging failure case example DB 21. The second calculator 75 calculates a second index value quantitatively indicating a degree of priority of the consideration image 26C in the case where the consideration image 26C is viewed by the participants.

The screen output controller 76 generates the conference screen 30 based on the target menu extracted by the first extractor 73, the failed image file extracted by the second extractor 74, and the like. The screen output controller 76 outputs the XML data of the generated conference screen 30 to the client terminal 12 as the requestor of the delivery request.

Figure 11:
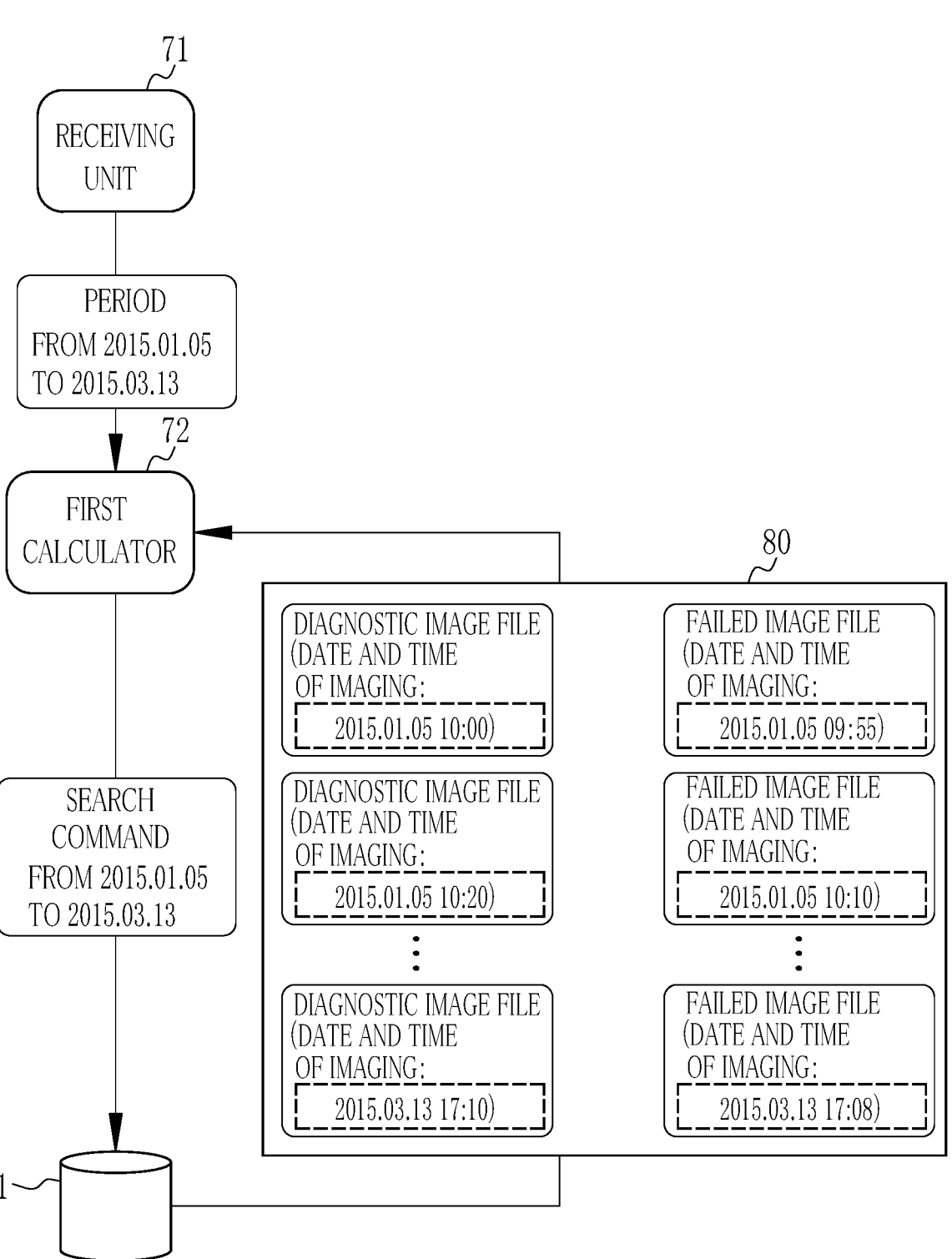
FIG. 11 illustrates that a first calculator acquires a diagnostic image file and a failed image file.

In FIG. 11, the first calculator 72 receives the information regarding the period from the receiving unit 71. The first calculator 72 outputs a search command designating the same period as the received period to the imaging failure case example DB 21. In response to the search command from the first calculator 72, the imaging failure case example DB 21 searches the diagnostic image file and the failed image file in each of which the date and time of imaging corresponding to the designated period is inputted, and outputs a search result 80 to the first calculator 72.

Note that, in the case where the period is not inputted in the designation screen 50 and there is no information regarding the period in the designation information, all the diagnostic image files and the failed image files in the imaging failure case example DB 21 are outputted as the search result 80 from the imaging failure case example DB 21 to the first calculator 72.

In FIG. 11, as the period, "from 2015.01.05 to 2015.03.13" is illustrated by way of example in the similar manner as FIGS. 8 and 9. Therefore, the search result 80 consists of the diagnostic image files and the failed image files in each of which the date and time of imaging corresponding to the period "from 2015.01.05 to 2015.03.13" is inputted.

Figure 12:
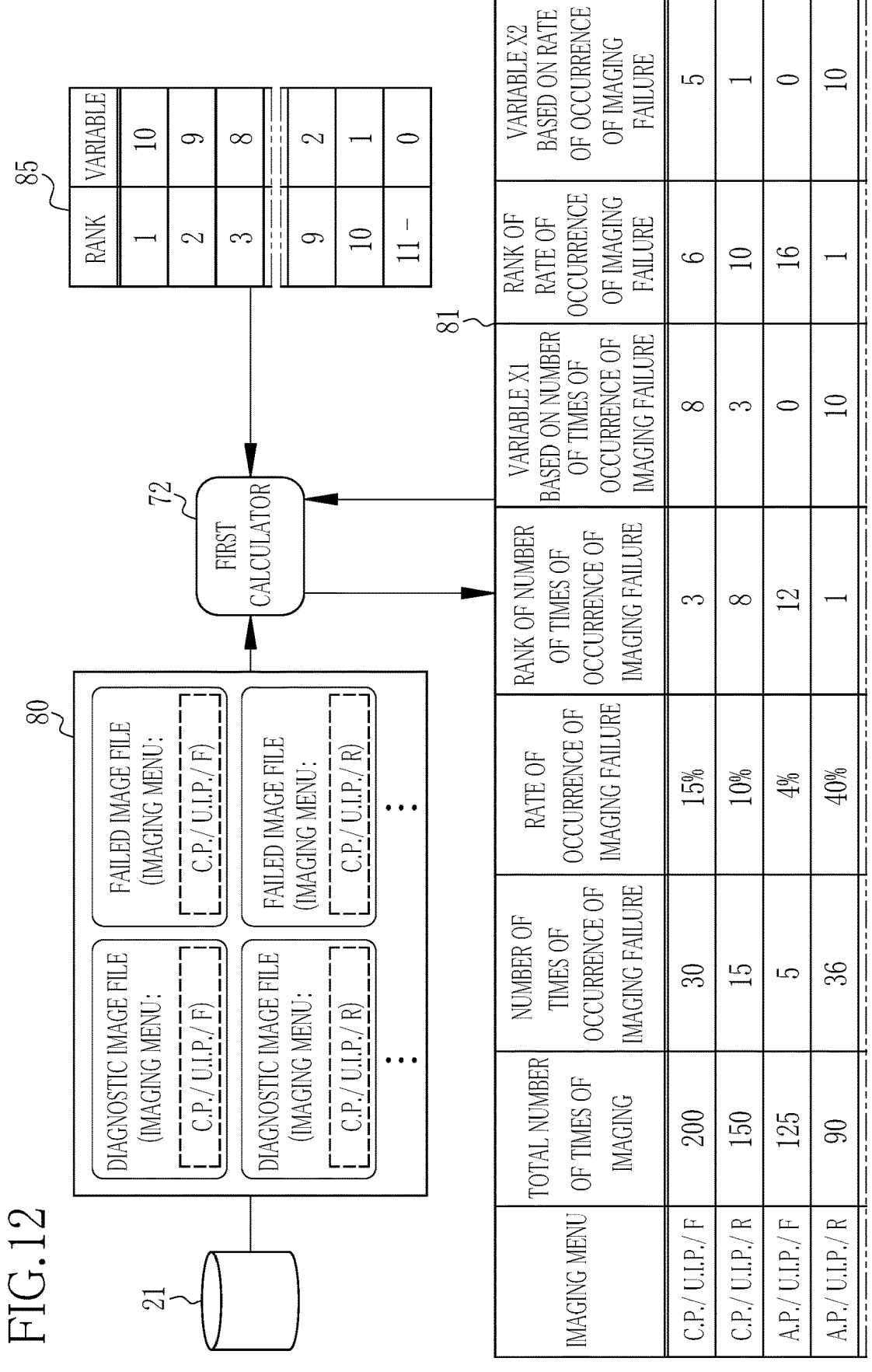
FIG. 12 illustrates that the first calculator derives variables based on the number of times of occurrence of imaging failure for each imaging menu and variables based on the rate of occurrence of imaging failure for each imaging menu.

In FIG. 12, the first calculator 72 generates intermediate process data 81 based on the search result 80. Specifically, at first, the first calculator 72 focuses attention on the imaging menus of the diagnostic image file and the failed image file in the search result 80, and counts the total number of times of imaging by summing up the number of diagnostic image files and the number of failed image files for each imaging menu.

Next, based on the number of failed image files in the search result 80, the number of times of occurrence of imaging failure is counted for each imaging menu, and further the number of times of occurrence of imaging failure is divided by the total number of times of imaging, so as to calculate the rate of occurrence of imaging failure that is the rate of the number of times of occurrence of imaging failure relative to the total number of times of imaging for each imaging menu. For example, in the case of the imaging menu "chest part/upright imaging posture/front" (abbreviated as "C.P./U.I.P./F" in the drawings), the total number of times of imaging is 200, the number of times of occurrence of imaging failure is 30, and thus the rate of occurrence of imaging failure expressed by $(30/200) \times 100$ equals to 15%.

After the counting of the number of times of occurrence of imaging failure and the calculation of the rate of occurrence of imaging failure, the first calculator 72 ranks each imaging menu according to the number of times of occurrence of imaging failure in descending order and the rate of occurrence of imaging failure in descending order. Then, by referring to a table 85 according to rank and variable, a variable X1 based on the number of times of occurrence of imaging failure in accordance with the rank thereof, and a variable X2 based on the rate of occurrence of imaging failure in accordance with the rank thereof are derived for each imaging menu. The variable X1 is a variable based on the number of times of occurrence of imaging failure for each imaging menu, and the variable X2 is a variable based on the rate of occurrence of imaging failure for each imaging menu.

The table 85 according to rank and variable is a data table in which variables corresponding to the rank are registered, and stored in the storage device 35B, for example. Here, a variable "10" is registered for the first rank, a variable "9" is registered for the second rank, . . . , a variable "2" is registered for the ninth rank, and a variable "1" is registered for the tenth rank. Namely, the variable is decreased by 1 from "10" registered for the first rank. A variable "0" is registered for the 11th or lower rank.

In the case of the imaging menu "chest part/upright imaging posture/front", for example, the number of times of occurrence of imaging failure is ranked at third place, and therefore "8" is derived as the variable X1, and the rate of occurrence of imaging failure is ranked at sixth place, and therefore "5" is derived as the variable X2. The variables X1 and X2 are registered in the intermediate process data 81. In the case of the imaging menu "abdominal part/upright imaging posture/front" (abbreviated as "A. P./U. I. P./F" in the drawings), the number of times of occurrence of imaging failure is ranked at 12th place and the rate of occurrence of imaging failure is ranked at 16th place, namely, both of them are ranked at lower than 11th place. Therefore, "0" is derived as each of the variables X1 and X2, and registered in the intermediate process data 81.

Figure 13:
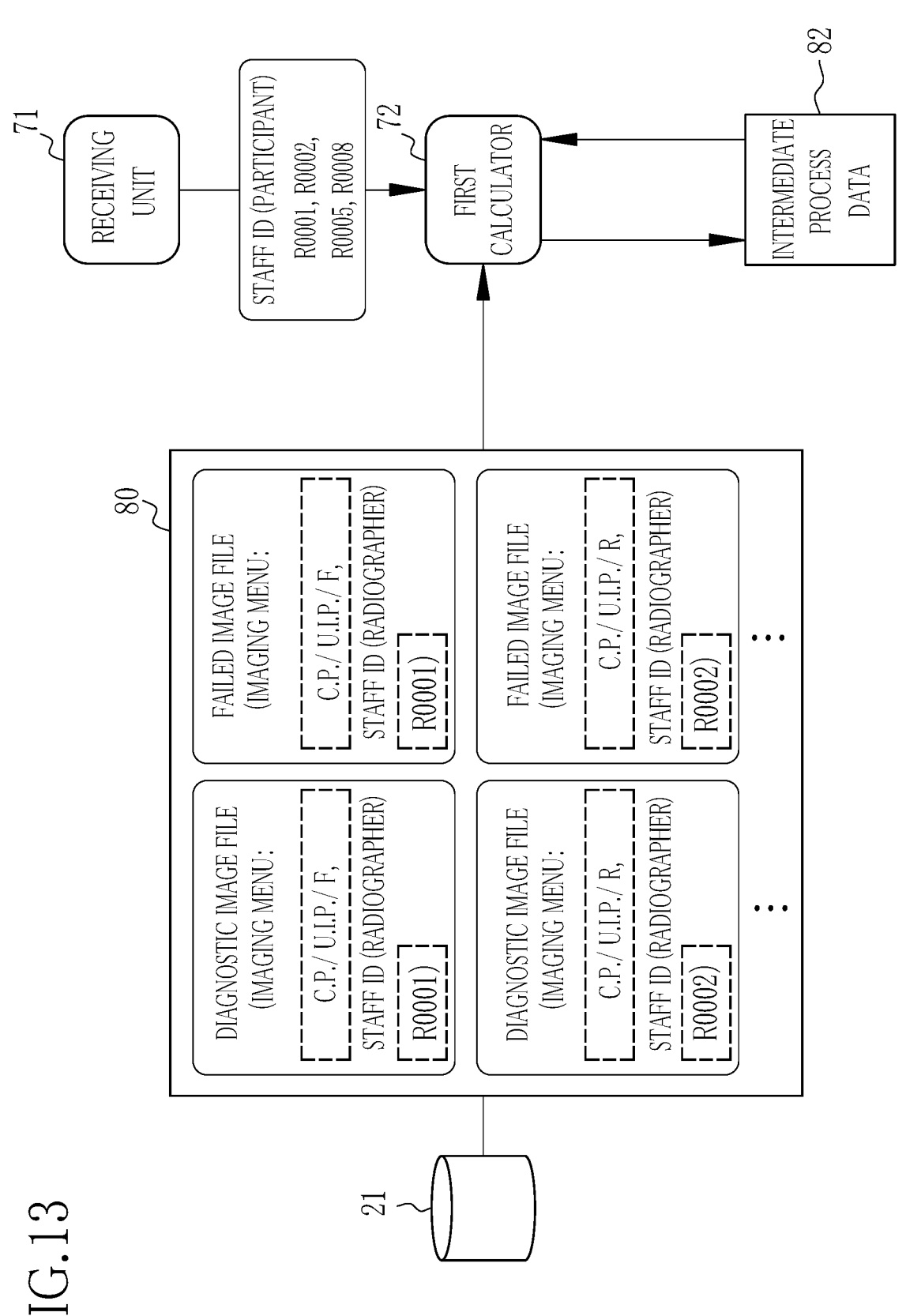
FIG. 13 illustrates that the first calculator derives variables based on the number of times of occurrence of imaging failure for each imaging menu for each participant and variables based on the rate of occurrence of imaging failure for each imaging menu for each participant.

In FIG. 13, the first calculator 72 receives the information regarding the staff IDs of the participants from the receiving unit 71. The first calculator 72 generates intermediate process data 82 based on the information regarding the staff IDs and the search result 80. The first calculator 72 focuses attention on the imaging menus and the staff IDs in the diagnostic image file and the failed image file in the search result 80, and subjects the diagnostic image file and the failed image file, in which the staff IDs of the participants are inputted, to the same process as in the case of the intermediate process data 81, so as to generate the intermediate process data 82.

As shown in FIG. 14, the intermediate process data 82 is obtained by gathering the intermediate process data 81 of each of the participants. Here, as the staff IDs of the participants, "R0001", "R0002", "R0005", and "R0008" are illustrated by way of example in the similar manner as FIGS. 8 and 9, and variables X3, X5, X7, and X9 based on the number of times of occurrence of imaging failure and variables X4, X6, X8, and X10 based on the rate of occurrence of imaging failure are derived for the respective staff IDs. The variables X3, X5, X7, and X9 are variables based on the number of times of occurrence of imaging failure for each imaging menu for each participant, and the variables X4, X6, X8, and X10 are variables based on the rate of occurrence of imaging failure for each imaging menu for each participant. Note that, regarding the staff ID "R0005" and "R0008", due to the limitation of drawing space, the number of times of occurrence of imaging failure, the rate of occurrence of imaging failure, and the like are not shown in the drawing.

Figure 15:
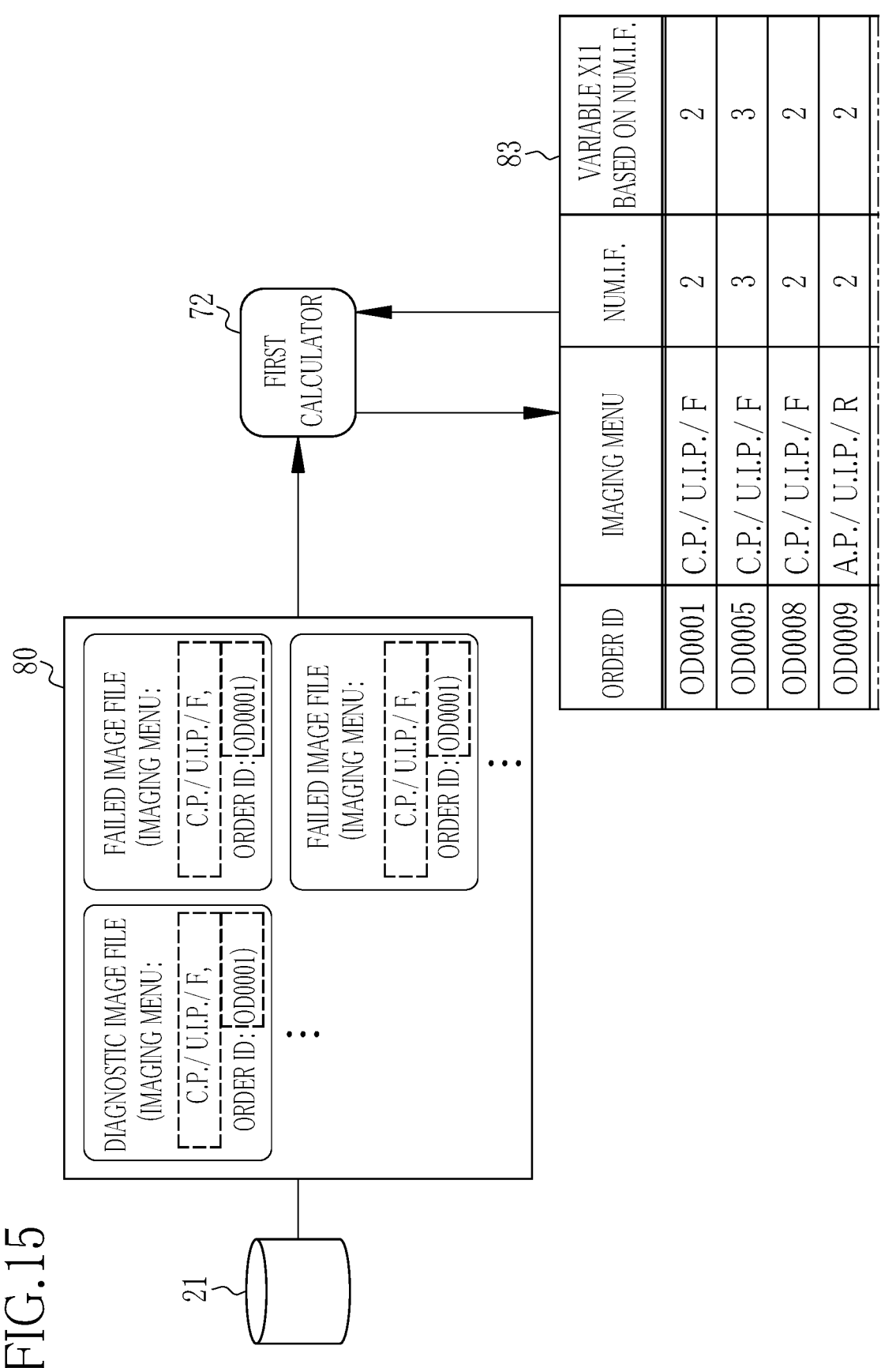
FIG. 15 illustrates that the first calculator derives variables based on the number of times of occurrence of imaging failure for each imaging menu in image capturing corresponding to the same imaging order.

Further, as shown in FIG. 15, the first calculator 72 focuses attention on the imaging menu and the order ID in the failed image file in the search result 80, and generates intermediate process data 83. Specifically, the first calculator 72 extracts the order ID and the imaging menu of two or more failed image files in each which the same order ID is inputted among the failed image files in the search result 80. Then, the first calculator 72 registers the number of failed image files as the number of times of occurrence of imaging failure. The first calculator 72 derives a variable X11 based on the number of times of occurrence of imaging failure. Here, the first calculator 72 derives a numerical value, which is equal to the number of times of occurrence of imaging failure, as the variable X11. The variable X11 is a variable based on the number of times of occurrence of imaging failure for each imaging menu in the image capturing corresponding to the same imaging order.

In FIG. 15, there are two failed image files in each of which the order ID "OD0001" and the imaging menu "chest part/upright imaging posture/front" are inputted in the search result 80, and therefore the order ID "OD0001", the imaging menu "chest part/5 upright imaging posture/front", the number of times of occurrence of imaging failure "2", and the variable X11 "2" are registered in the intermediate process data 83.

Figure 16:
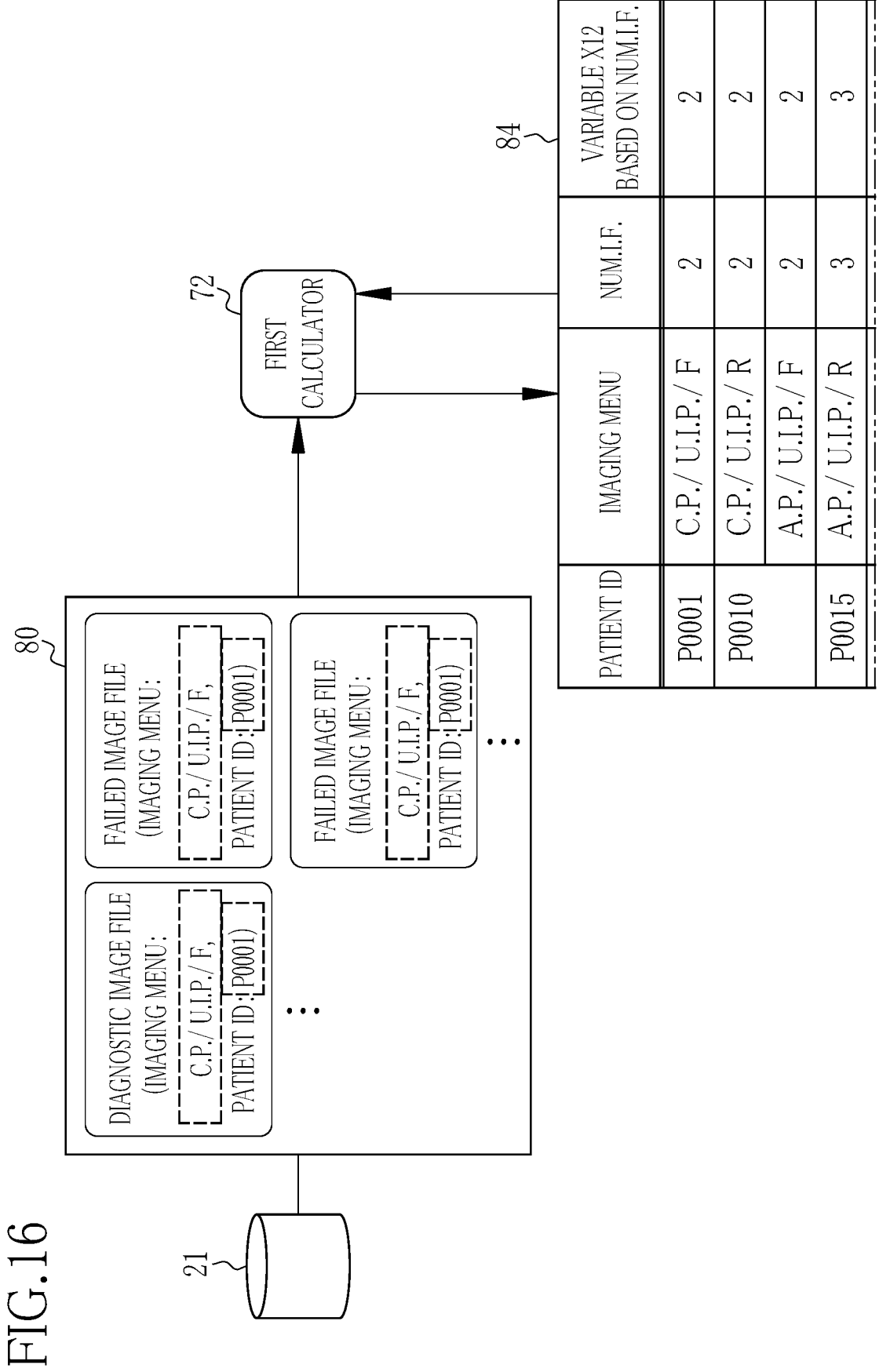
FIG. 16 illustrates that the first calculator derives variables based on the number of times of occurrence of imaging failure for each imaging menu in image capturing corresponding to the same patient.

Further, as shown in FIG. 16, the first calculator 72 focuses attention on the imaging menu and the patient ID in the failed image file in the search result 80, and generates intermediate process data 84. Specifically, the first calculator 72 extracts the patient ID and the imaging menu in two or more failed image files in each of which the same patient ID is inputted among the failed image files in the search result 80. Then, the first calculator 72 registers the number of failed image files as the number of times of occurrence of imaging failure. The first calculator 72 derives a variable X12 based on the number of times of occurrence of imaging failure. Here, as the variable X12, as in the case of the variable X11, a numerical value which is the same as the number of times of occurrence of imaging failure is derived. The variable X12 is a variable based on the number of times of occurrence of imaging failure for each imaging menu in the image capturing corresponding to the same patient.

In FIG. 16, there are two failed image files in each of which the patient ID "P0001" and the imaging menu "chest part/upright imaging posture/front" are inputted in the search result 80, and therefore the patient ID "P0001", the imaging menu "chest part/upright imaging posture/front", the number of times of occurrence of imaging failure "2", and the variable X12 "2" are registered in the intermediate process data 84. Incidentally, in the case where there are two or more failed image files, in each of which the same patient ID is inputted, for a plurality of the imaging menus in the search result 80, the number of times of occurrence of imaging failure and the variable X12 for each imaging menu are registered, as shown in the item of patient ID "P0010" in the intermediate process data 84.

Figure 17:
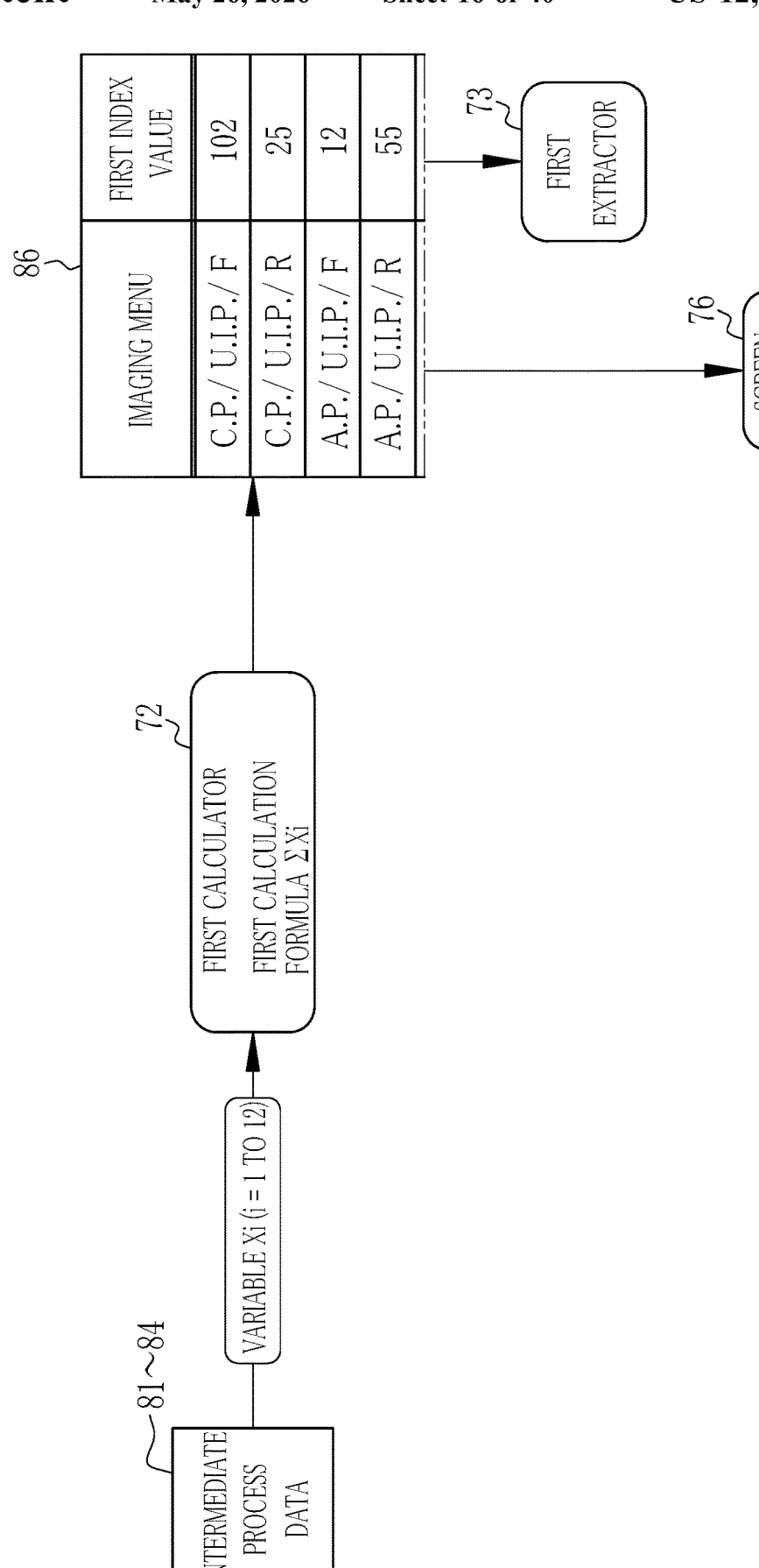
FIG. 17 is an explanatory view illustrating a function of the first calculator for calculating a first index value.

In FIG. 17, the first calculator 72 reads out each variable Xi (i=1 to 12) from each of the intermediate process data 81 to 84. The first calculator 72 calculates the first index value for each imaging menu using a first calculation formula $\Sigma Xi$ for obtaining summation of the variables Xi. The first calculator 72 outputs a calculation result 86 of the first index value to the first extractor 73 and the screen output controller 76.

The first index value may be calculated by adding or multiplying an adequate weighting coefficient to each variable Xi. For example, 10 is added to each of the variable X1 based on the number of times of occurrence of imaging failure for each imaging menu and the variable X2 based on the rate of occurrence of imaging failure for each imaging menu. Alternatively, each of the variable X11 based on the number of times of occurrence of imaging failure for each imaging menu in the image capturing corresponding to the same imaging order and the variable X12 based on the number of times of occurrence of imaging failure for each imaging menu in the image capturing corresponding to the same patient is multiplied by 2. In this case, the weighting coefficient may be configured to be settable on the client terminal 12.

Note that, since there are four patients here, there are four variables X3, X5, X7, and X9 based on the number of times of occurrence of imaging failure for each imaging menu for each participant, and there are four variables X4, X6, X8, and X10 based on the rate of occurrence of imaging failure for each imaging menu for each participant. However, the change in the number of participants varies the number of the variables. Therefore, the suffix "i" is not limited to 1 to 12 described above. Further, although the suffix "i" of the variable based on the number of times of occurrence of imaging failure for each imaging menu in the image capturing corresponding to the same imaging order is set to 11, and the suffix "i" of the variable based on the number of times of occurrence of imaging failure for each imaging menu in the image capturing corresponding to the same patient is set to 12, for the convenience of explanation, the suffix "i" varies depending on the number of the participants.

Figure 18:
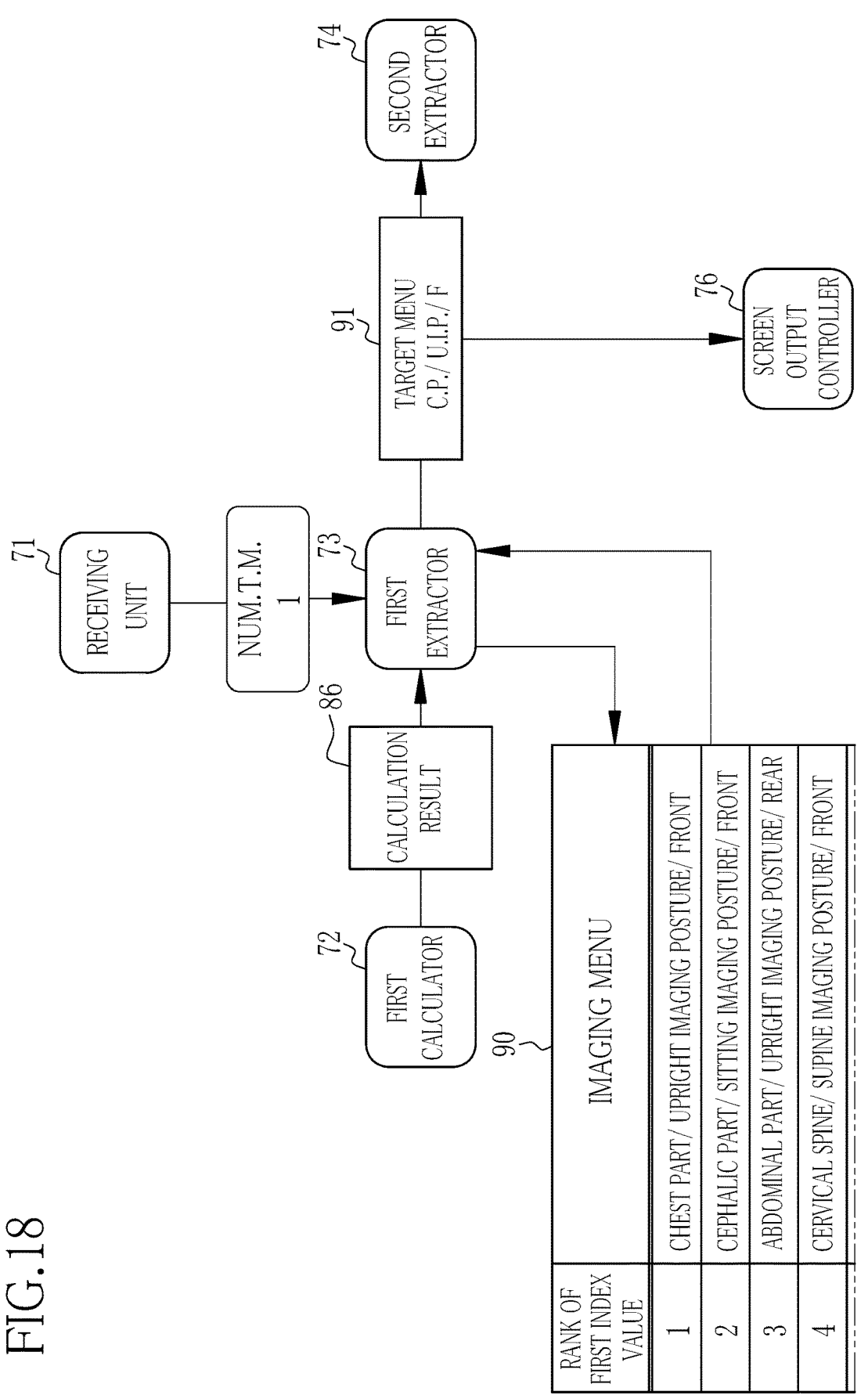
FIG. 18 is an explanatory view illustrating a function of the first extractor for extracting a target menu.

In FIG. 18, the first extractor 73 receives the information regarding the number of target menus from the receiving unit 71 and the calculation result 86 of the first index value from the first calculator 72. The first extractor 73 extracts the designated number of target menus based on the calculation result 86.

More specifically, the first extractor 73 generates intermediate process data 90 in which the imaging menus are sorted in descending order of the first index value of the calculation result 86. Then, the first extractor 73 extracts the imaging menu as the target menu in order of rank of the first index value from first place in the intermediate process data 90, and stops the extraction at the point of time when the number of extracted target menus reaches the designated number. The first extractor 73 outputs the target menus extracted as described above as an extraction result 91 to the second extractor 74 and the screen output controller 76.

Note that, in the case where the number of the target menus is not inputted in the designation screen 50 and there is no information regarding the number of target menus in the designation information, three imaging menus ranked at first to third places in the intermediate process data 90 are extracted as the target menus, for example.

In FIG. 18, the number of the target menus is set to "1" and the imaging menu ranked at first place in the intermediate process data 90 is "chest part/upright imaging posture/front", and therefore the imaging menu "chest part/upright imaging posture/front" ranked at first place is extracted as the target menu.

Figure 19:
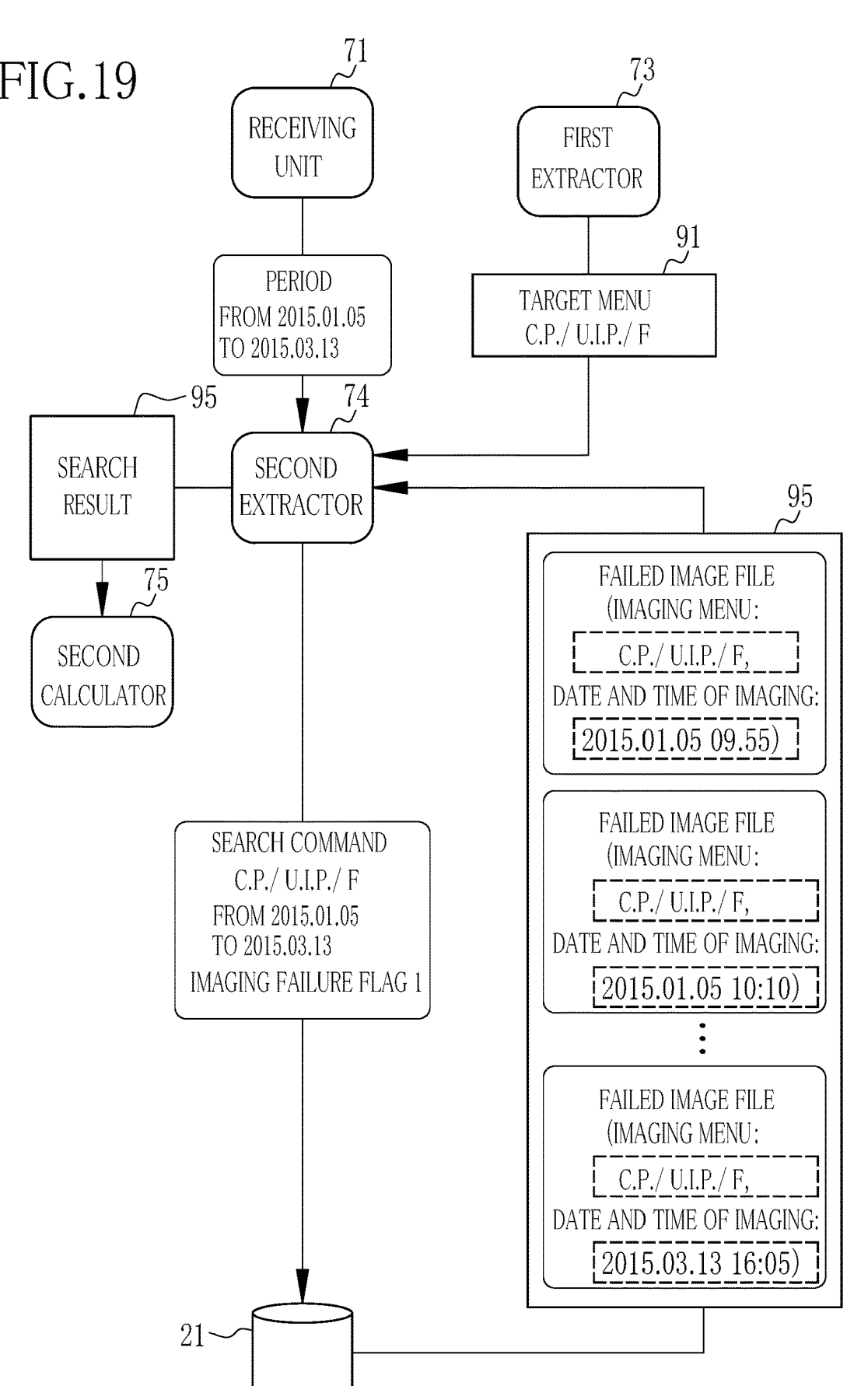
FIG. 19 illustrates that a second extractor acquires a failed image as a consideration image.

In FIG. 19, the second extractor 74 receives the information regarding the period from the receiving unit 71 and an extraction result 91 of the target menu from the first extractor 73. The second extractor 74 outputs the period which is the same as the received period, the imaging menu which is the same as the received target menu, and the search command which designates an imaging failure flag "1" (failed image file) to the imaging failure case example DB 21. The imaging failure case example DB 21 searches the failed image file, in which the date and time of imaging corresponding to the period and the imaging menu that is the same as the target menu are inputted, in response to the search command from the second extractor 74, and outputs a search result 95 to the second extractor 74. The second extractor 74 outputs the search result 95 to the second calculator 75.

Note that, in the case where the period is not inputted in the designation screen 50 and there is no information regarding the period in the designation information, all the failed image files, in each of which the imaging menu that is the same as the target menu in the imaging failure case example DB 21 is inputted, are outputted as the search result 95 from the imaging failure case example DB 21 to the second extractor 74.

In FIG. 19, as the period, "from 2015.01.05 to 2015.03.13" is illustrated by way of example in the similar manner as FIG. 9 and the like. Further, as the target menu, "chest part/upright imaging posture/front" is illustrated by way of example in the similar manner as FIG. 18. Therefore, the search result 95 consists of the failed image files, in each of which the date and time of imaging corresponding to the period "from 2015.01.05 to 2015.03.13" and the imaging menu "chest part/upright imaging posture/front" are inputted.

Figure 20:
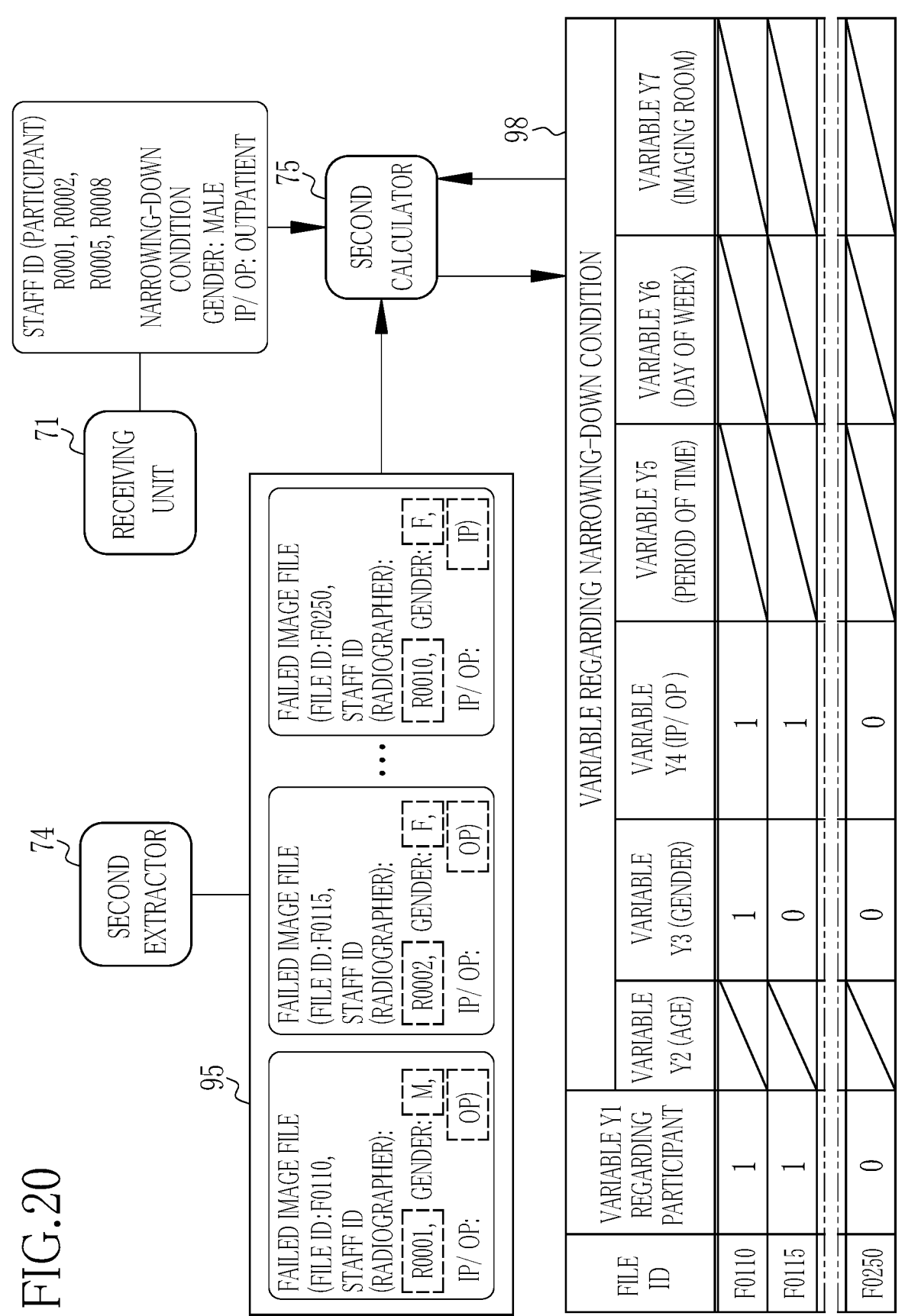
FIG. 20 illustrates that a second calculator derives variables based on whether or not the failed image as the consideration image is associated with a participant and variables regarding a narrowing-down condition.

In FIG. 20, the second calculator 75 receives the information regarding the staff IDs of the participants and the information regarding the narrowing-down condition from the receiving unit 71. Further, the second calculator 75 receives the search result 95 from the second extractor 74.

The second calculator 75 generates intermediate process data 98 based on the search result 95. Specifically, at first, the second calculator 75 focuses attention on the staff ID in the failed image file of the search result 95, and derives a variable Y1 regarding the participant, and registers the variable Y1 for each file ID in the failed image file of the search result 95. The variable Y1 is a variable based on whether or not the failed image as the consideration image 26C is associated with the participant.

Regarding the failed image file in which a staff ID that is the same as the staff ID of the participant is inputted, namely, the failed image file based on the failed image captured by the participant, "1" is derived as the variable Y1. In contrast, regarding the failed image file in which a staff ID that is different from the staff ID of the participant is inputted, namely, the failed image file based on the failed image captured by a person other than the participant, "0" is derived as the variable Y1.

In FIG. 20, as the staff IDs of the participants, the staff IDs "R0001", "R0002", "R0005", and "R0008" are illustrated by way of example in the similar manner as FIG. 9 and the like. Further, since the staff IDs of the participants "R0001" and "R0002" are inputted in the failed image files having the file IDs "F0110" and "F0115", respectively, the variable Y1 "1" is registered in the item of the file ID of each of the failed image files of the intermediate process data 98.

In contrast, in the failed image file having the file ID "F0250", a staff ID "R0010" that is different from the staff ID of the participant is inputted, and therefore a variable Y1 "0" is registered in the item of the file ID "F0250" of the intermediate process data 98.

Next, the second calculator 75 focuses attention on the item designated by the narrowing-down condition in the accompanying information of the failed image file of the search result 95, and derives variables Y2 to Y7 regarding the narrowing-down condition and registers the variables Y2 to Y7 for each file ID. The variable Y2 corresponds to the age, the variable Y3 corresponds to the gender, the variable Y4 corresponds to the inpatient/outpatient classification, the variable Y5 corresponds to the period of time, the variable Y6 corresponds to the day of week, and the variable Y7 corresponds to the imaging room, as the narrowing-down condition.

Regarding the failed image file in which the accompanying information corresponding to the narrowing-down condition is inputted, "1" is derived as the variables Y2 to Y7. In contrast, regarding the failed image file in which the accompanying information that does not correspond to the narrowing-down condition is inputted, "0" is derived as the variables Y2 to Y7.

Note that, the second calculator 75 derives only the variable corresponding to the narrowing-down condition from the receiving unit 71 among the variables Y2 to Y7. Other variables are not derived as shown by diagonal lines in the drawing. Further, in the case where the narrowing-down condition is not selected in the designation screen 50 and there is no information regarding the narrowing-down condition in the designation information, the second calculator 75 does not derive the variables Y2 to Y7, and derives only the variable Y1.

In FIG. 20, as the narrowing-down condition, the gender "male" and the inpatient/outpatient classification "outpatient" are illustrated by way of example in the similar manner as FIG. 9. Since the gender "male" and the inpatient/outpatient classification "outpatient", which correspond to the narrowing-down condition from the receiving unit 71, are inputted in the failed image file having the file ID "F0110", the variable Y3 "1" and the variable Y4 "1" are registered in the item of the file ID "F0110" of the intermediate process data 98.

In contrast, since the gender "female" (abbreviated "F" in the drawings) and the inpatient/outpatient classification "inpatient", which do not correspond to the narrowing-down condition from the receiving unit 71, are inputted in the failed image file having the file ID "F0250", "0" is registered as the variables Y3 and Y4 in the item of file ID "F0250" of the intermediate process data 98.

Figure 21:
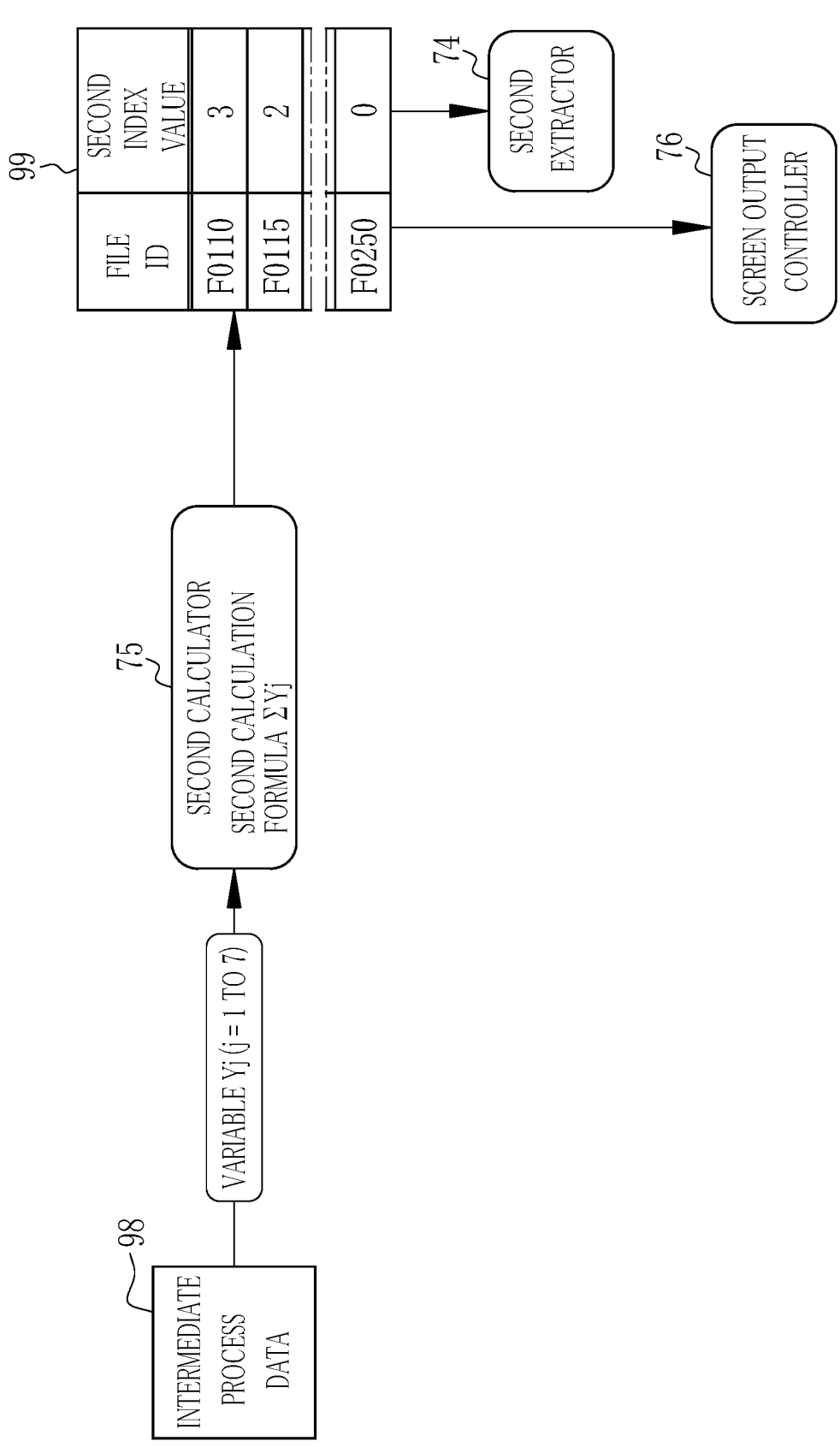
FIG. 21 is an explanatory view illustrating a function of the second calculator for calculating a second index value.

In FIG. 21, the second calculator 75 reads out each variable Yj (j=1 to 7) from the intermediate process data 98. The second calculator 75 calculates a second index value for each failed image file using a second calculation formula ΣYj for obtaining summation of the variables Yj. The second calculator 75 outputs a calculation result 99 of the second index value to the second extractor 74 and the screen output controller 76. Incidentally, as in the case of the first index value, the second index value may be calculated by adding or multiplying an adequate weighting coefficient to each variable Yj. Further, the weighting coefficient may be configured to be settable on the client terminal 12.

Figure 22:
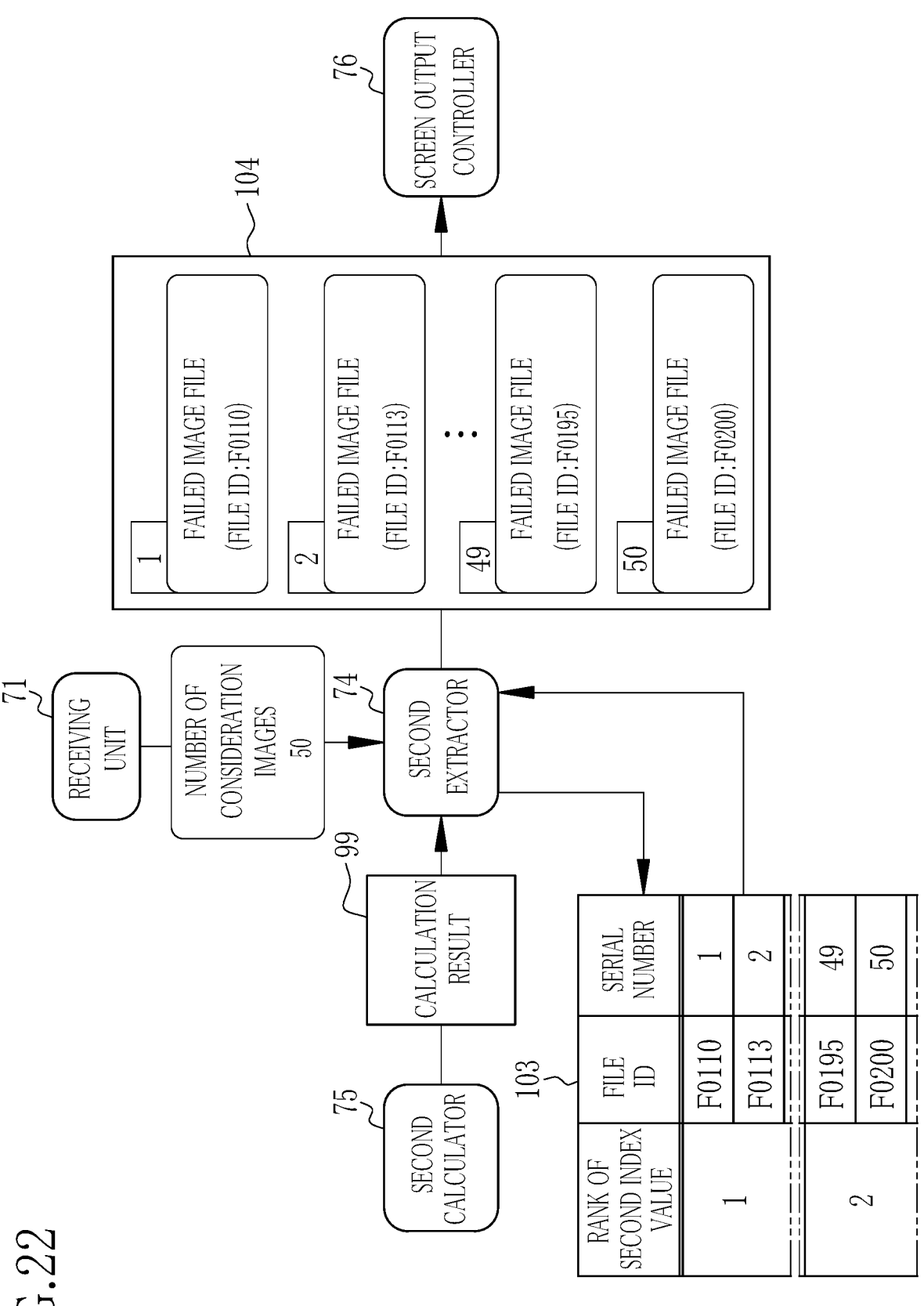
FIG. 22 is an explanatory view illustrating a function of the second extractor for extracting the failed image as the consideration image.

In FIG. 22, the second extractor 74 receives the information regarding the number of the consideration images from the receiving unit 71 and a calculation result 99 of the second index value from the second calculator 75. The second extractor 74 extracts the designated number of failed image files (failed images as the consideration images 26C) based on the calculation result 99.

More specifically, the second extractor 74 generates intermediate process data 103 in which the file IDs of the failed image files of the search result 95 are sorted in descending order of the second index value of the calculation result 99. The second extractor 74 registers the file IDs of the failed image files each having the same second index value in the same rank, and assigns a serial number to each of the file IDs in ascending order of the number of the file ID. Then, the second extractor 74 extracts the failed image file in ascending order of the serial number from the failed image file having the file ID assigned with the serial number "1" in the intermediate process data 103, and stops the extraction at the point of time when the number of extracted failed image files reaches the designated number. The second extractor 74 outputs the failed image files extracted as described above as an extraction result 104 to the screen output controller 76.

Note that, in the case where the number of consideration images is not inputted in the designation screen 50 and there is no information regarding the number of the consideration images in the designation information, ten failed image files having the file IDs assigned with the serial numbers "1" to "10" are extracted. Further, in the case where the number of failed image files of the search result 95 does not reach the designated number, all the failed image files of the search result 95 are extracted regardless of the second index value.

In FIG. 22, the number of consideration images is set to "50", the file ID "F0110" is registered with the serial number "1", the file ID "F0113" is registered with the serial number "2", . . . , the file ID "F0195" is registered with the serial number "49", and the file ID "F0200" is registered with the serial number "50" in the intermediate process data 103, and therefore the failed image files having the file IDs "F0110", "F0113", . . . , "F0195", and "F0200" are extracted.

Figure 23:
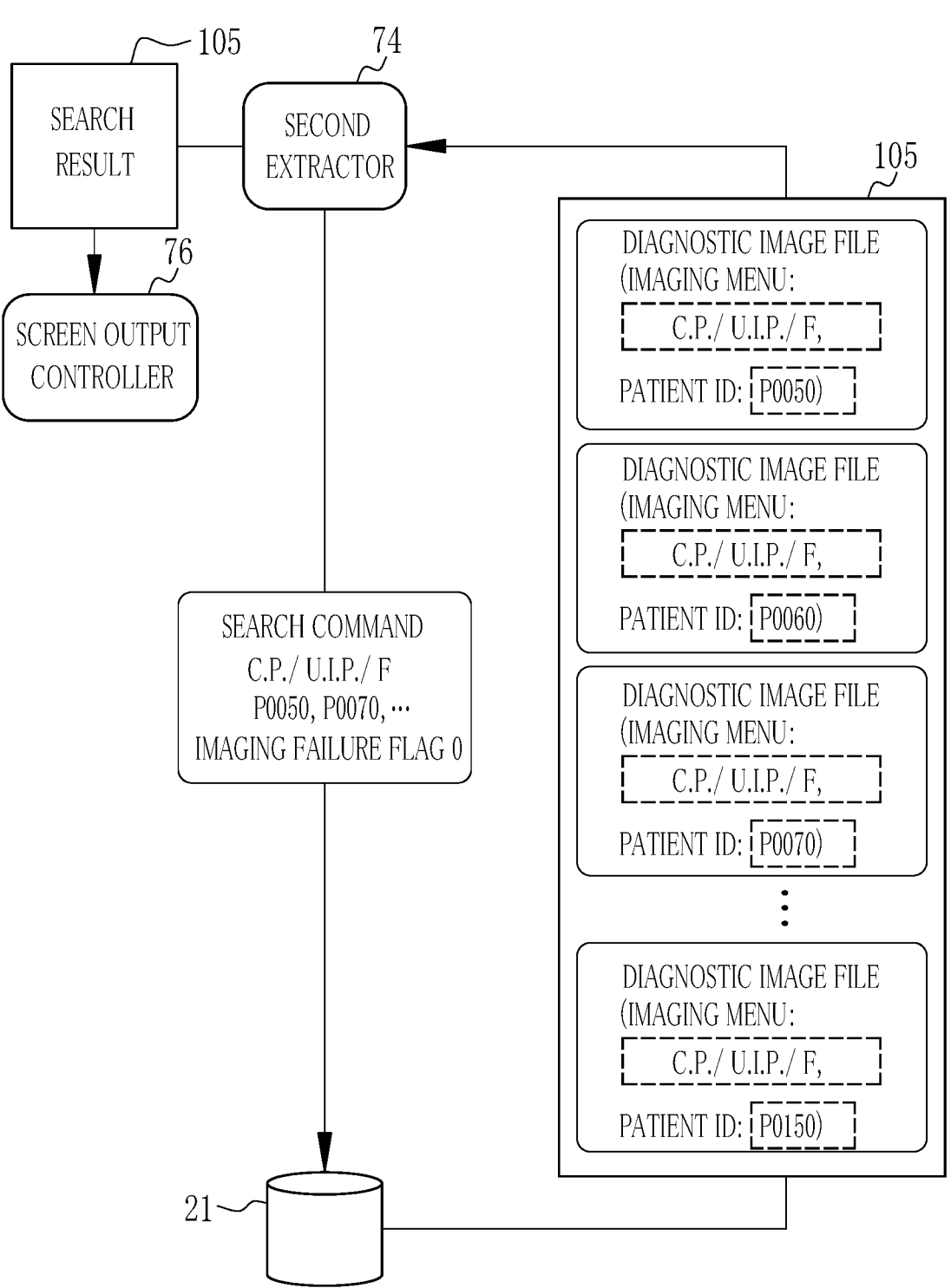
FIG. 23 illustrates that the second extractor acquires a diagnostic image as a reference image.
Figure 27:
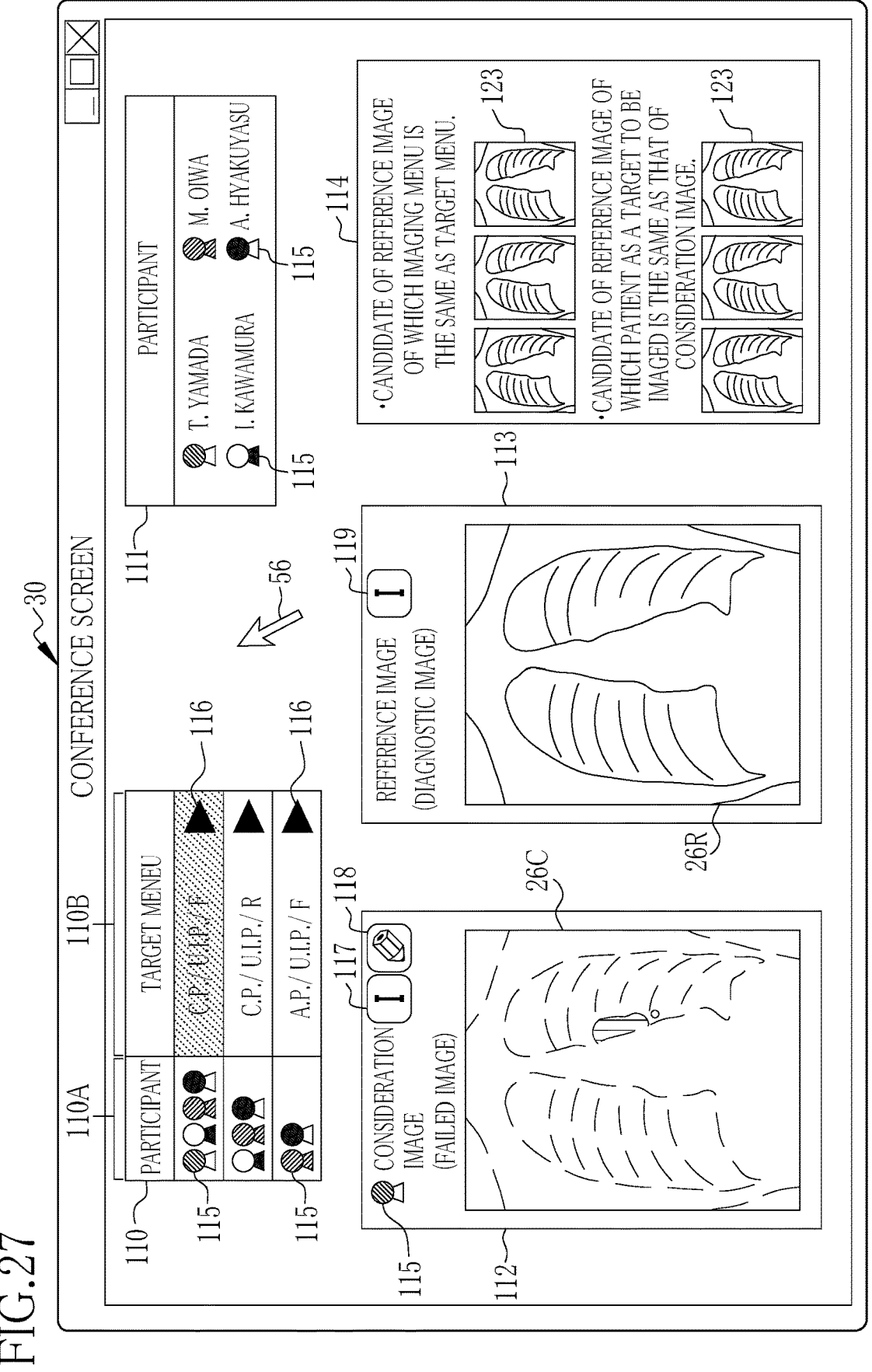
FIG. 27 illustrates the conference screen on which the consideration image and the reference image are displayed.

In FIG. 23, after the extraction of the failed image files, the second extractor 74 searches the diagnostic images as reference images 26R (see FIG. 27). Specifically, the second extractor 74 outputs a search command designating an imaging menu which is the same as the target menu, a patient ID which is the same as that of the failed image file of the extraction result 104, and an imaging failure flag "0" (diagnostic image file) to the imaging failure case example DB 21. In response to the search command from the second extractor 74, the imaging failure case example DB 21 searches a diagnostic image file, in which an imaging menu that is the same as the target menu containing the diagnostic image file having the same patient ID as that of the failed image file of the extraction result 104 is inputted, and outputs the search result 105 to the second extractor 74. The second extractor 74 outputs the search result 105 to the screen output controller 76. Instead of the patient ID, the order ID may be designated by the search command.

In FIG. 23, as the target menu, the target menu "chest part/upright imaging posture/front" is illustrated byway of example in the similar manner as FIG. 18 and the like. Therefore, the search result 105 consists of the diagnostic image files in each of which the imaging menu "chest part/upright imaging posture/front" is inputted. Further, as the patient ID of the failed image file of the extraction result 104, "P0050" and "P0070" are illustrated by way of example. Therefore, the diagnostic image files having the patient IDs "P0050" and "P0070", and the diagnostic image file having another patient ID such as "P0060" and "P0150" are mixed in the search result 105.

Figure 24:
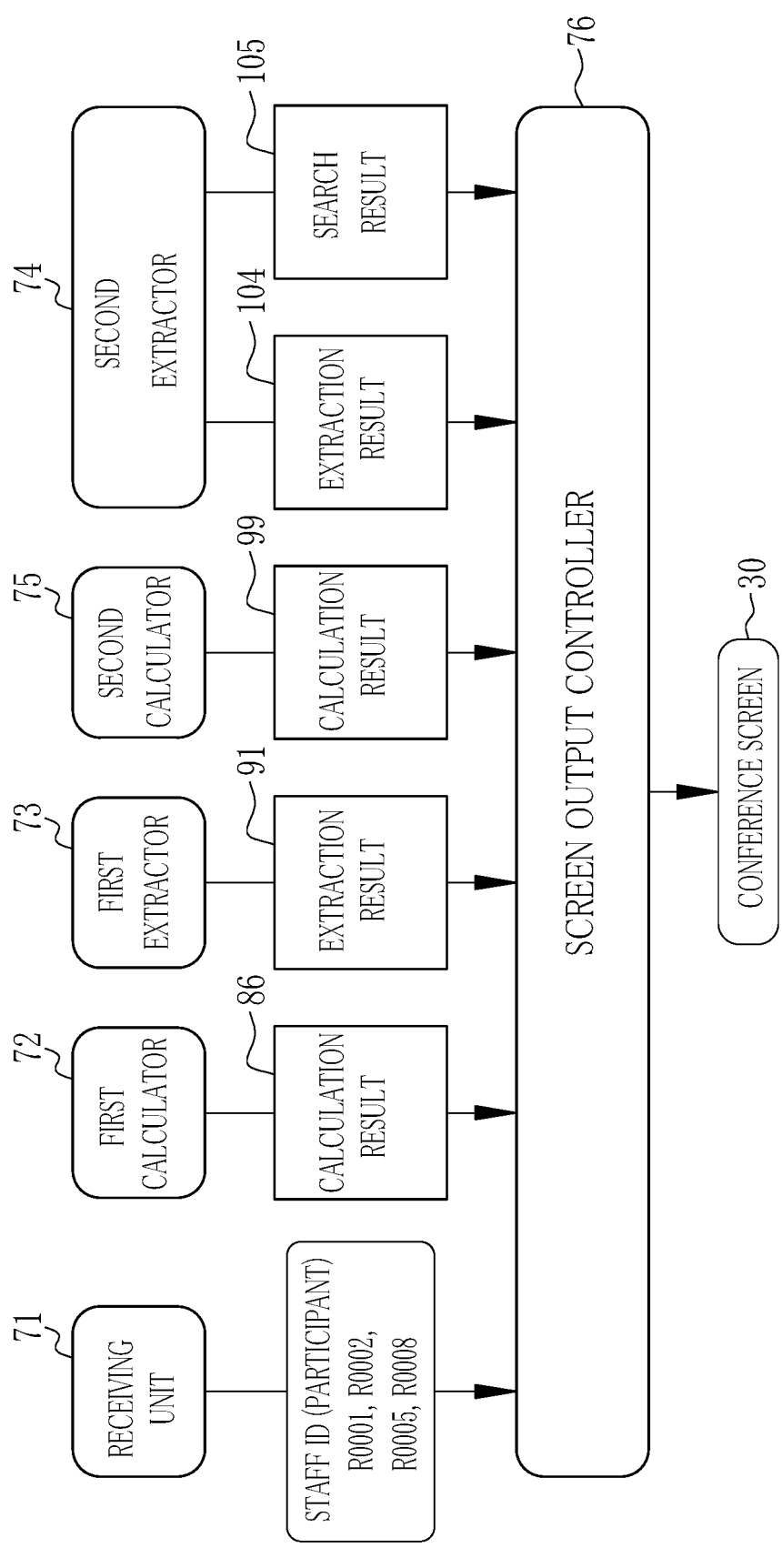
FIG. 24 is an explanatory view illustrating a screen output control function of a screen output controller.

In FIG. 24, the screen output controller 76 receives the information regarding the staff IDs of the participants from the receiving unit 71, the calculation result 86 of the first index value from the first calculator 72, and the extraction result 91 of the target menu from the first extractor 73. Further, the screen output controller 76 receives the calculation result 99 of the second index value from the second calculator 75, the extraction result 104 of the failed image file and the search result 105 of the diagnostic image file from the second extractor 74. The screen output controller 76 generates the conference screen 30 based on the information regarding the staff IDs of the participants, the calculation results 86 and 99, the extraction results 91 and 104, and the search result 105.

More specifically, the screen output controller 76 displays the information regarding the participants based on the information regarding the staff IDs of the participants on the conference screen 30. Further, the screen output controller 76 displays the target menu based on the extraction result 91 on the conference screen 30.

Further, the screen output controller 76 displays the consideration image 26C based on the extraction result 104 and the reference image 26R based on the search result 105 on the conference screen 30. The consideration image 26C is the radiographic image 26 (failed image) stored in the image storage 28 of the failed image file of the extraction result 104. The reference image 26R is the radiographic image 26 (diagnostic image) stored in the image storage 28 of the diagnostic image file of the search result 105.

In the case where there are a plurality of the target menus extracted by the first extractor 73, the screen output controller 76 displays the target menus arranged in accordance with the first index values of the calculation result 86 on the conference screen 30. Further, in the case where there are a plurality of the failed image files extracted by the second extractor 74, namely, in the case where there are a plurality of the consideration images 26C, the screen output controller 76 displays the consideration images 26C arranged in accordance with the second index values of the calculation result 99 on the conference screen 30.

Figure 25:
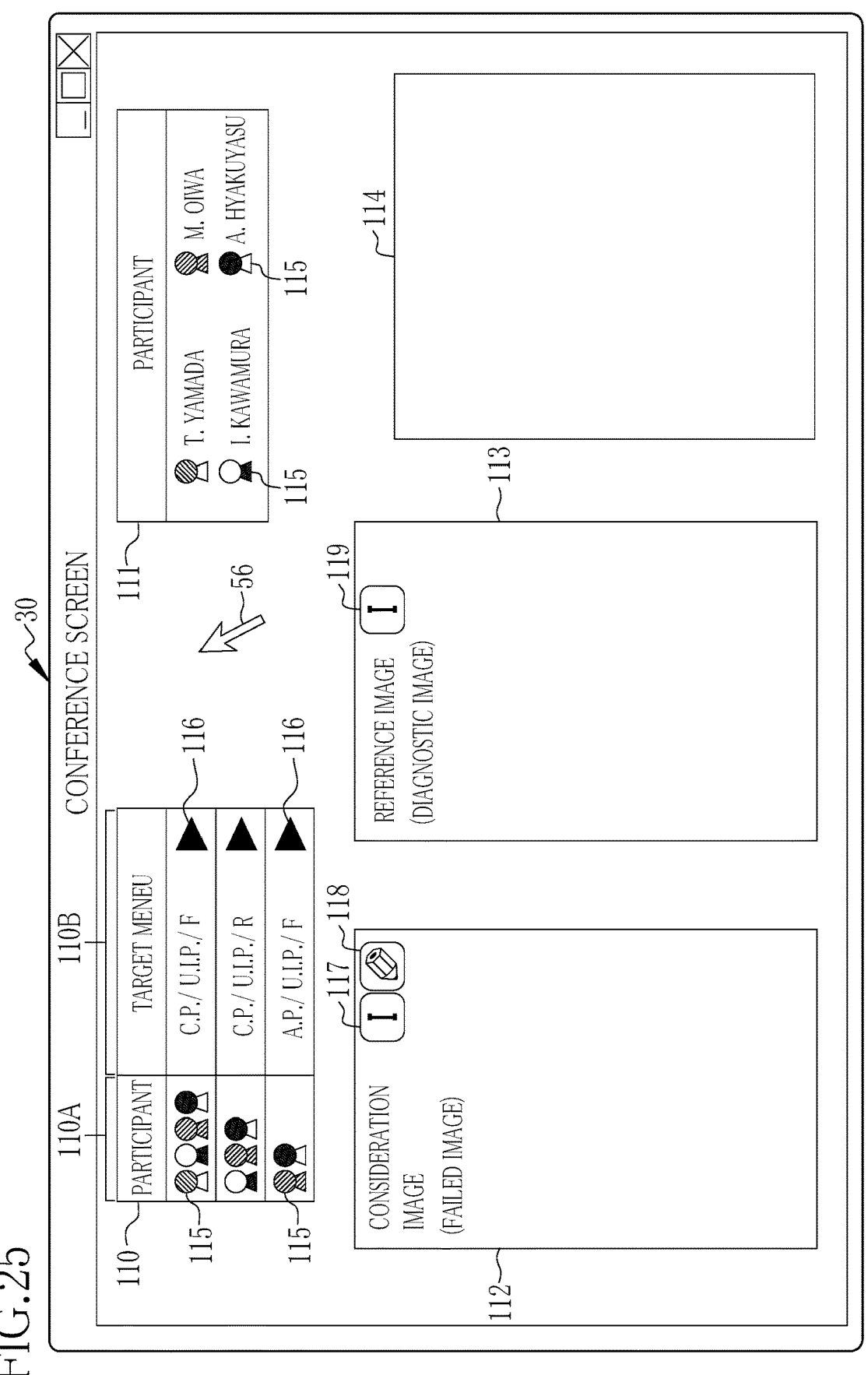
FIG. 25 illustrates a conference screen in an initial display state.

In FIG. 25 illustrating the conference screen 30 in an initial display state, the conference screen 30 includes a target menu display region 110, a participant display region 111, a consideration image display region 112, a reference image display region 113, and a reference image candidate display region 114.

The display state of the target menu display region 110 is in accordance with the information regarding the staff IDs of the participants, the calculation result 86 of the first index value, and the extraction result 91 of the target menu. The target menu display region 110 consists of a display field 110A for icons 115 representing individual participants and a display field 110B for the target menus. The icon 115 in the display field 110A represents that there is the consideration image 26C captured by the participant represented by the icon 115 among the consideration images 26C extracted in accordance with the target menu in the display field 110B.

The target menus are arranged from the top in descending order of the first index value in the display field 110B. Expand buttons 116 are provided next to the target menus on one-to-one basis.

The display state of the participant display region 111 is in accordance with the information regarding the staff IDs of the participants. The icons 115 and the full names of the participants are displayed in the participant display region 111. The icons 115 displayed in the participant display region 111 are the same as those displayed in the display field 110A of the target menu display region 110. The icons 115 are different from one another in the color and the pattern as shown by the hatching so as to distinguish the individual participants.

In FIG. 25, three target menus "chest part/upright imaging posture/front", "chest part/upright imaging posture/rear" (abbreviated as "C.P./U.I.P./R" in the drawings), and "abdominal part/upright imaging posture/front" are displayed in the display field 110B, by way of example. In this case, the target menu "chest part/upright imaging posture/front" displayed at the top in the display order has the largest first index value among the three target menus. The target menu "abdominal part/upright imaging posture/front" displayed at the bottom in the display order has the smallest first index value among the three target menus.

Further, in FIG. 25, four participants, "Tadashi YAMADA", "Ichiro KAWAMURA", "Misaki OIWA", and "Ayaka HYAKUYASU" are displayed by way of example in the similar manner as FIG. 8. In the display field 110A corresponding to the target menu "chest part/upright imaging posture/front" in the display field 110B, for example, the icons 115 of all the four participants are displayed. Thus, it is represented that there are the consideration images 26C captured by the four participants among the consideration images 26C extracted regarding the target menu "chest part/upright imaging posture/front".

The display state of the consideration image display region 112 is in accordance with the information regarding the staff IDs of the participants and the extraction result 104 of the failed image file. Further, the display state of each of the reference image display region 113 and the reference image candidate display region 114 is in accordance with the search result 105 of the diagnostic image file. Incidentally, the display regions 112 to 114 are blank in the initial display state as shown in FIG. 25.

An information button 117 for displaying the accompanying information in association with the consideration image 26C, and a note button 118 in which notes such as a reason of the imaging failure and what the participant says are written are disposed in the upper portion of the consideration image display region 112. An information button 119 for displaying the accompanying information in association with the consideration image 26R is disposed in the upper portion of the reference image display region 113 as in the case of the information button 117.

Figure 26:
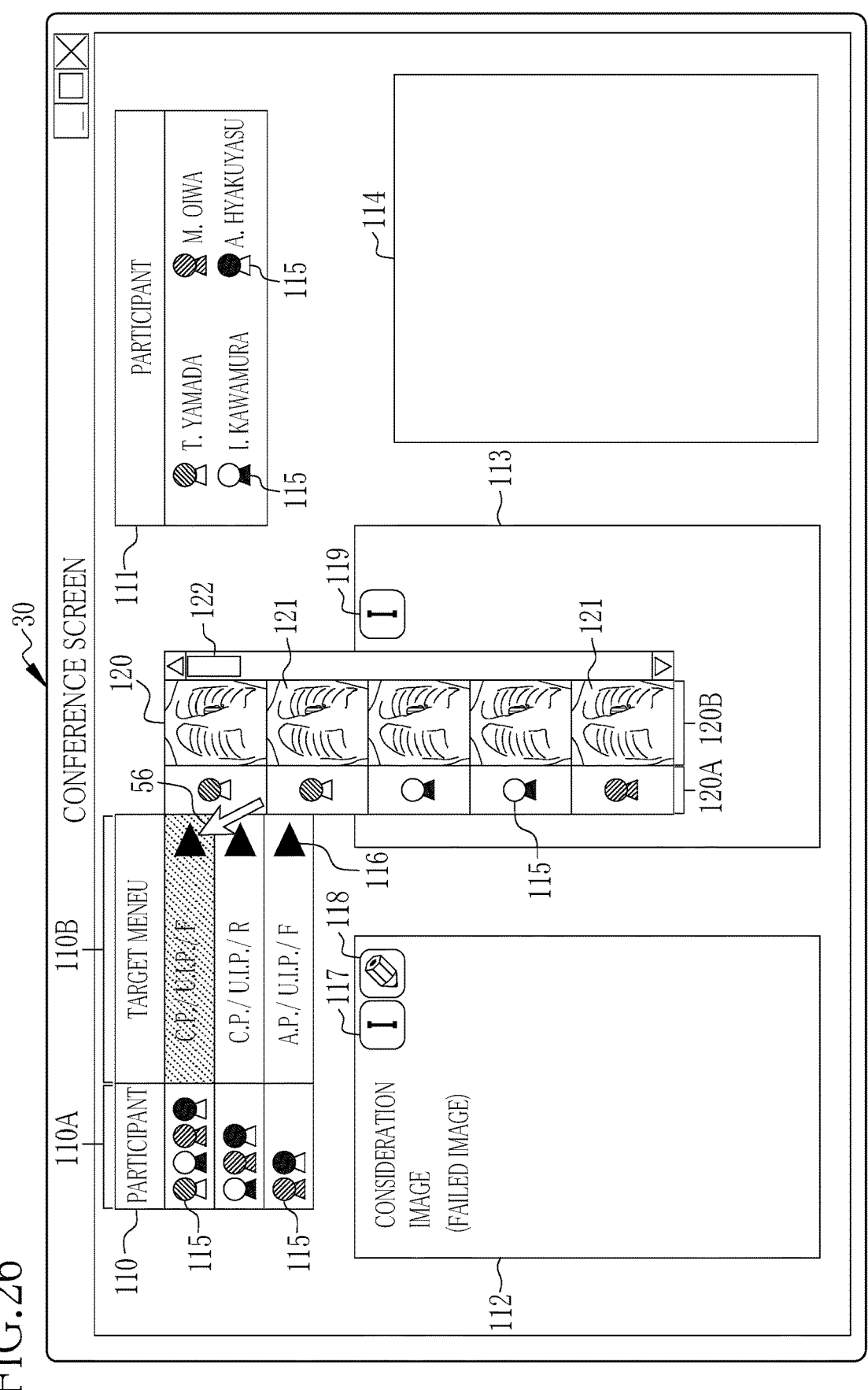
FIG. 26 illustrates the conference screen on which a consideration image selection region is displayed.

In FIG. 26, in the case where the expand button 116 of the desired target menu in the display field 110B is selected using the cursor 56, a consideration image selection region 120 appears next to the target menu display region 110. The target menu of which expand button 116 is selected changes in the color and the pattern as shown by the hatching so as to be distinguished from the other target menus. Here, an example, in which the target menu "chest part/upright imaging posture/front" displayed at the top is selected, is illustrated.

The display state of the consideration image selection region 120 is in accordance with the information regarding the staff IDs of the participants, the calculation result 99 of the second index value, and the extraction result 104 of the failed image file. The consideration image selection region 120 consists of a display field 120A for the icons 115 and a display field 120B for thumbnails 121 of the consideration images 26C. Further, a scroll bar 122 used for displaying hidden icons 115 and thumbnails 121 is disposed in the consideration image selection region 120.

The icon 115 in the display field 120A represents that the consideration image 26C displayed by the thumbnail 121 in the display field 120B was captured by the participant corresponding to the icon 15. Further, the thumbnails 121 are arranged in descending order of the second index value in the display field 120B.

In FIG. 27, in the case where a desired thumbnail 121 in the display field 120B is selected using the cursor 56, the consideration image selection region 120 disappears. Then, the consideration image 26C of which thumbnail 121 is selected using the cursor 56, and the icon 115 which is the same as that in the display field 120A and corresponds to the consideration image 26C are displayed in the consideration image display region 112. Incidentally, among the icons 115 in the participant display region 111, the icon 115 which is the same as that displayed in the consideration image display region 112 may be highlighted by being blinked, for example.

The reference image 26R is displayed in the reference image display region 113, and thumbnail 123 of the candidate of the reference image 26R is displayed in the reference image candidate display region 114, respectively. The thumbnails 123 in the reference image candidate display region 114 are displayed as the candidates of the reference images 26R arranged in the upper portion of the reference image candidate display region 114 and the candidates of the reference images 26R arranged in the lower portion of the reference image candidate display region 114, among the reference images 26R in association with the imaging menu which is the same as the target menu of which expand button 116 is selected. The candidates of the reference images 26R arranged in the upper portion of the reference image candidate display region 114 are associated with a patient different from the imaging target of the consideration image 26C displayed in the consideration image display region 112. The candidates of the reference images 26R arranged in the lower portion of the reference image candidate display region 114 are associated with a patient that is the same as the imaging target of the consideration image 26C displayed in the consideration image display region 112. The reference image 26R to be displayed in the reference image display region 113 can be switched by selecting the thumbnail 123 using the cursor 56. Incidentally, instead of the candidates of the reference images 26R associated with a patient different from the imaging target of the consideration image 26C displayed in the consideration image display region 112, the reference images 26R each of which imaging order is the same as that of the consideration image 26C displayed in the consideration image display region 112 (i.e., the diagnostic images obtained by performing the image capturing again after the consideration image 26C as the failed image was captured) may be displayed in the upper portion of the reference image candidate display region 114.

Figure 28:
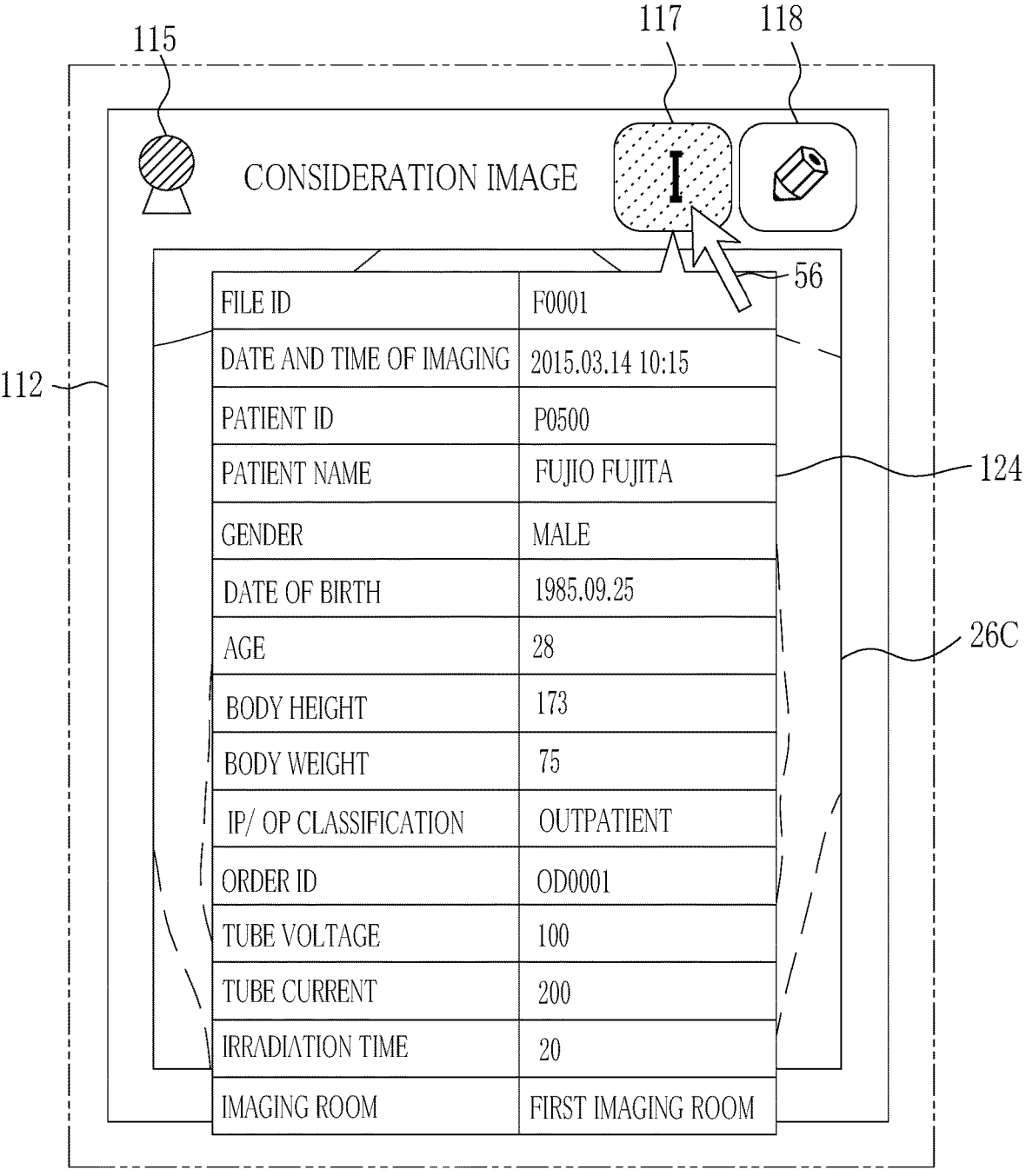
FIG. 28 illustrates an accompanying information display region.

As shown in FIG. 28, in the case where the information button 117 is selected using the cursor 56, an accompanying information display region 124 appears in the consideration image display region 112. Accompanying information associated with the consideration image 26C (e.g., the file ID, date and time of imaging, patient ID, order ID, tube voltage, tube current, irradiation time, and the like) is displayed in the accompanying information display region 124. Although not shown in the drawing, in the case where the information button 119 is selected using the cursor 56, an accompanying information display region for displaying accompanying information associated with the reference image 26R appears in the reference image display region 113. In the case where the note button 118 is selected using the cursor 56, a text input box appears on the conference screen 30, and thereby it become possible to input a note through the text input box. The inputted note is associated with the consideration image 26C, and registered in the imaging failure case example DB 21.

Figure 29:
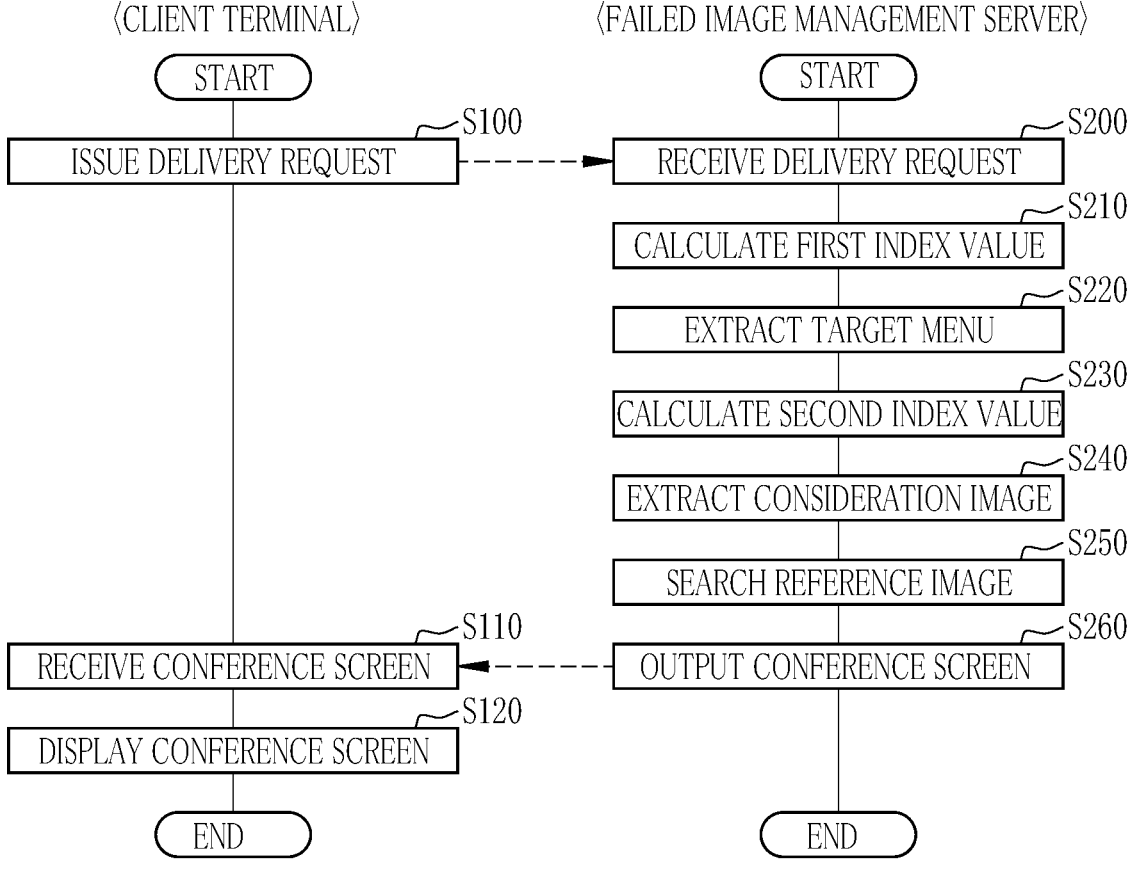
FIG. 29 is a flow chart illustrating a flow of processing performed by a CPU of the client terminal and a CPU of the failed image management server.

An operation of the above configuration is explained hereinbelow by referring to the flowchart in FIG. 29. At first, as a preparation for the conference, each of the medical staff members operates the client terminal 12, and inputs a command for delivering the conference screen 30 through the designation screen 50. In response to the command for delivering the conference screen 30, the browser controller 46 generates designation information. Then, as shown in step S100, the delivery request for the conference screen 30 containing the designation information is issued from the browser controller 46 to the failed image management server 13.

On the designation screen 50, it is possible to designate the number of the target menus to be extracted, the number of the consideration images 26C to be extracted, a calculation target period in which the first index value is calculated, and an extraction target period in which the consideration image 26C is extracted. Since it becomes possible to designate the number of the target menus, the number of the consideration images, the calculation target period, and the extraction target period as described above, the consideration with the focus on main points can be performed within a limited consideration time.

In the failed image management server 13, a delivery request is received by the receiving unit 71 (step S200). The information regarding the staff IDs of the participants and the information regarding the period in the designation information contained in the delivery request are transmitted to the first calculator 72. The information regarding the number of target menus is outputted to the first extractor 73. The information regarding the number of consideration images 26C and the information regarding the period are outputted to the second extractor 74. The information regarding the staff IDs of the participants and the information regarding the narrowing-down condition are outputted to the second calculator 75. The information regarding the staff IDs of the participants is outputted to the screen output controller 76.

The first index value is calculated by the first calculator 72 (step S210). The calculation result 86 of the first index value is outputted to the first extractor 73 and the screen output controller 76.

The first index value is calculated using the first calculation formula $\Sigma Xi$ having the variable X1 based on the number of times of occurrence of imaging failure for each imaging menu and the variable X2 based on the rate of occurrence of imaging failure for each imaging menu. Therefore, the first index value is based on both of the number of times of occurrence of imaging failure for each imaging menu and the rate of occurrence of imaging failure for each imaging menu. Consequently, the first index value makes it possible to know exactly the imaging failure state for each imaging menu.

The first calculation formula $\Sigma Xi$ has not only the variables X1 and X2 but also the variables X3, X5, X7, and X9 based on the number of times of occurrence of imaging failure for each imaging menu for each participant and the variables X4, X6, X8, and X10 based on the rate of occurrence of imaging failure for each imaging menu for each participant. Therefore, the first index value is also based on the imaging failure state for each imaging menu for each participant.

Further, the first calculation formula $\Sigma Xi$ also has the variable X11 based on the number of times of occurrence of imaging failure for each imaging menu in the image capturing corresponding to the same imaging order, and the variable X12 based on the number of times of occurrence of imaging failure for each imaging menu in the image capturing corresponding to the same patient. Therefore, the first index value is also based on the imaging failure state in the image capturing corresponding to the same imaging order and the imaging failure state in the image capturing corresponding to the same patient.

In the first extractor 73, based on the calculation result 86 of the first index value, the designated number of the target menus are extracted (step S220). Specifically, the first extractor 73 extracts the imaging menu as the target menu in order of rank of the first index value from first place, and stops the extraction at the point of time when the number of extracted target menus reaches the designated number. The first extractor 73 outputs the extraction result 91 of the target menus extracted as described above to the second extractor 74 and the screen output controller 76.

In this embodiment, the first index value is summation of the variables Xi as expressed by the first calculation formula $\Sigma Xi$. Therefore, the first index value is increased as the number of times of occurrence of imaging failure is increased at the same time as the rate of occurrence of imaging failure is increased and as the variables Xi become larger, namely, as the frequency of imaging failure is increased. Concurrently, the rank of the first index value becomes higher. Consequently, the imaging menu having the first index value of which rank is relatively high is an imaging menu of which frequency of imaging failure is relatively high.

In this embodiment, since the imaging menu having the first index value of which rank is relatively high is automatically extracted as the target menu by the first extractor 73, the imaging menu of which frequency of imaging failure is relatively low is extracted and designated. Therefore, there is no fear that useless consideration is performed and results in waste of precious time of the medical staff members, and it becomes possible for the medical staff members to perform the consideration for reliably achieving decrease in the frequency of imaging failure.

Further, since the target menu is automatically extracted, it is unnecessary for the medical staff members to know exactly the imaging failure state for each imaging menu in order to extract and designate the imaging menu of which frequency of imaging failure is relatively high. Consequently, it is possible to decrease a burden on each of the medical staff members, such that the medical staff members can sufficiently consider improvement on the image capturing.

At the conference, it is preferable that not the radiographic image 26 captured by a person other than the participants but the radiographic image 26 captured by one of the participants is viewed as the consideration image 26C, because the radiographic image 26 captured by one of the participants is more familiar to the participants and the consideration proceeds.

In this embodiment, the imaging failure state of each imaging menu of each participant is taken consideration into the first index value due to the variables X3 to X10 as described above. Therefore, as the number of times of occurrence of imaging failure of the participant is increased at the same time as the rate of occurrence of imaging failure of the participant is increased, the imaging menu has the first index value of which rank is higher, and thus the imaging menu tends to be frequently extracted as the target menu by the first extractor 73. Consequently, the probability of the radiographic image 26 captured by one of the participants being viewed as the consideration image 26C is increased.

In the case where the image capturing corresponding to the same imaging order or the image capturing corresponding to the same patient fails many times, the necessity of considering improvement on the image capturing is high, in order to prevent repeated failures and prevent increase in the frequency of imaging failure.

In this embodiment, the imaging failure state in the image capturing corresponding to the same imaging order and the imaging failure state in the image capturing corresponding to the same patient are taken consideration into the first index value due to the variables X11 and X12 as described above. Therefore, in the case where the image capturing corresponding to the same imaging order or the image capturing corresponding to the same patient fails many times, the imaging menu has the first index value of which rank is higher, and thus the imaging menu tends to be frequently extracted as the target menu by the first extractor 73. Consequently, the probability of the radiographic image 26 obtained in the failed image capturing corresponding to the same imaging order or the same the patient being viewed as the consideration image 26C is increased.

The second extractor 74 acquires the search result 95 of the failed image file, in which the imaging menu that is the same as the target menu is inputted, from the imaging failure case example DB 21. The search result 95 is outputted to the second calculator 75.

The second calculator 75 calculates the second index value regarding the failed image file of the search result 95 (step S230). The calculation result 99 of the second index value is outputted to the second extractor 74 and the screen output controller 76.

The second extractor 74 extracts the designated number of the failed image files (consideration images 26C) based on the calculation result 99 of the second index value (step S240). Specifically, the second extractor 74 extracts the failed image file in order of rank of the second index value from first place, and stops the extraction at the point of time when the number of failed image files reaches the designated number. The extraction result 104 of the failed image file thus extracted is outputted to the screen output controller 76.

The second index value is calculated using the second calculation formula $\Sigma Yj$ having the variable Y1 based on whether or not the failed image file of the search result 95 is associated with the participant. Therefore, in the failed image file in which the staff ID that is the same as that of the participant is inputted, the second index value becomes larger, and the rank of the second index value becomes higher. Thus, the failed image file in which the staff ID that is the same as that of the participant is inputted can be preferentially extracted.

Further, the second calculation formula $\Sigma Yj$ has the variables Y2 to Y7 corresponding to the narrowing-down condition, in addition to the variable Y1, and therefore the failed image file in which accompanying information corresponding to the narrowing-down condition is inputted has the larger second index value, and the rank of the second index value becomes higher. Thus, the failed image file in which the accompanying information corresponding to the narrowing-down condition is inputted can be preferentially extracted.

The search result 105 of the diagnostic image file, in which the imaging menu that is the same as the target menu containing the diagnostic image file having the patient ID that is the same as that of the failed image file of the extraction result 104 is inputted, is acquired as the reference image 26R by the second extractor 74 from the imaging failure case example DB 21 (step S250). The search result 105 is outputted to the screen output controller 76.

The screen output controller 76 generates the conference screen 30 based on the information regarding the staff IDs of the participants, the calculation result 86 of the first index value, the extraction result 91 of the target menu, the calculation result 99 of the second index value, the extraction result 104 of the failed image file, and the search result 105 of the diagnostic image file. The XML data of the conference screen 30 is outputted from the screen output controller 76 to the client terminal 12 as the requestor of the delivery request (step S260).

In the client terminal 12, the XML data of the conference screen 30 is received by the browser controller 46 (step S110). Based on the XML data, the browser controller 46 reproduces the conference screen 30 to be displayed on the web browser, and the GUI controller 45 displays the conference screen 30 on the display panel 39A (step S120).

On the conference screen 30, the target menu is displayed in the target menu display region 110, and the consideration image 26C is displayed in the consideration image display region 112. The participants of the conference view the conference screen 30 and consider improvement on the image capturing.

In the target menu display region 110, the target menus are arranged in descending order of the first index value. Further, in the consideration image selection region 120, the thumbnails 121 of the consideration images 26C are arranged in descending order of the second index value. In the case where there are two or more target menus or consideration images 26C, it is possible to easily find and select the target menu or the consideration image 26C which is highly beneficial in sufficiently decreasing the frequency of imaging failure.

The icon 115 representing the individual participant is displayed in the display field 110A of the target menu display region 110. The icon 115 is useful in noticing the existence of the consideration image 26C captured by the participant represented by the icon 115 among the consideration images 26C extracted regarding the target menu in the display field 110B, and the icon 115 can be referred to in selecting the target menu.

Further, the icon 115 is also displayed in the display field 120A of the consideration image selection region 12. The icon 115 is useful in knowing that the consideration image 26C displayed using the thumbnail 121 in the display field 120B was captured by the participant represented by the icon 115, and the icon 115 can be referred to in selecting the consideration image 26C.

Note that, instead of or in addition to displaying the icon 115, the target menu corresponding to the consideration image 26C captured by the participant, or the thumbnail 121 of the consideration image 26C captured by the participant may be displayed distinctively from others.

Not only the consideration image 26C but also the reference image 26R is displayed on the conference screen 30. Further, by selecting the information buttons 117 and 119 with use of the cursor 56, the accompanying information in association with the consideration image 26C and the accompanying information in association with the reference image 26R can be displayed, respectively. Therefore, it is possible to compare the consideration image 26C with the reference image 26R and compare the accompanying information in association with the consideration image 26C and the accompanying information in association with the reference image 26R. For example, after confirmation of the imaging condition in each of the accompanying information in association with the consideration image 26C and the accompanying information in association with the reference image 26R, it is possible to give a tutorial on the setting of the imaging condition for the purpose of preventing failure.

Note that, a frame-feed button and a frame-reverse button for manually switching the display between the consideration image 26C and the reference image 26R may be disposed in the consideration image display region 112 and the reference image display region 113. The frame feeding may be automatically performed at regular time intervals so as to display the consideration image 26C in the consideration image display region 112. In this case, it is preferable that the consideration images 26C are displayed in descending order of the second index value.

In the first embodiment described above, as illustrated by the thumbnails 121 in the display field 120B of the consideration image selection region 120, the consideration images 26C are displayed in accordance with the second index value. However, the arrangement for displaying the consideration images 26C is not limited thereto. The consideration images 26C may be displayed with the display size and the display position in accordance with the second index value.

Figure 30:
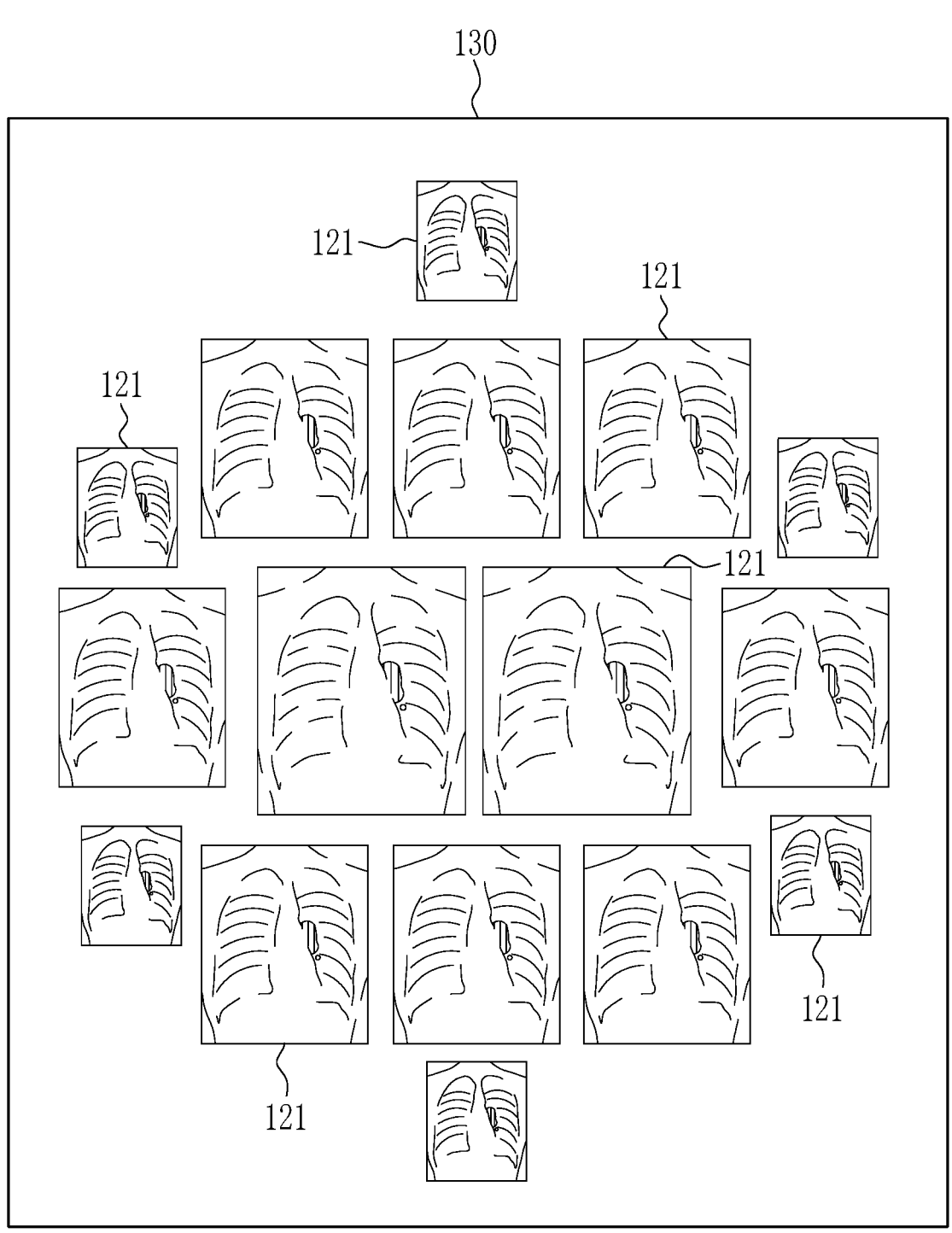
FIG. 30 illustrates another display example of the consideration image selection region.

Specifically, as in the case of a consideration image selection region 130 shown in FIG. 30, each of the thumbnails 121 of the consideration images 26C is displayed with the display size and the display position in accordance with the second index value. Namely, as the rank of the second index value of the consideration image 26C represented by the thumbnail 121 is higher, the display size of the thumbnail 121 becomes larger, and as the rank of the second index value of the consideration image 26C represented by the thumbnail 121 is higher, the display position of the thumbnail 121 becomes nearer to the center of the consideration image selection region 130. As described above, in the case where each of the consideration images 26C is displayed with the display size and the display position in accordance with the second index value, the consideration image 26C having the second index value ranked at relatively high place is selected more frequently due in part to a visual effect. Incidentally, as in the case of the consideration image selection region 120, the icon 115 may be displayed at the upper portion of the thumbnail 121 or the like.

In the first embodiment, based on the second index value calculated by the second calculator 75, the second extractor 74 determines the failed image as the consideration image 26C. However, the failed image as the consideration image

26C may not be determined based on the second index value. In this case, the second calculator 75 is not established in the CPU 37B, and the second extractor 74 extracts the failed image file of the search result 95 in reverse chronological order of date and time of imaging. Further, the second extractor 74 displays the thumbnails 121 of the consideration images 26C in reverse chronological order of date and time of imaging in the consideration image selection region 120.

Second Embodiment

In the first embodiment, the first calculation formula $\Sigma Xi$ having at least the variable X1 based on the number of times of occurrence of imaging failure for each imaging menu and the variable X2 based on the rate of occurrence of imaging failure for each imaging menu is used to calculate the first index value. However, according to a second embodiment illustrated in FIG. 31 to FIG. 38, the first index value is calculated using the first calculation formula having at least a variable based on an increasing rate of the frequency of imaging failure for each imaging menu.

Note that, in the second embodiment, the period designated in the item input region 52 of the designation screen 50 is only the extraction target period. Further, in the second embodiment, the staff ID of the participant who attends the current conference is described as the current staff ID.

Figure 31:
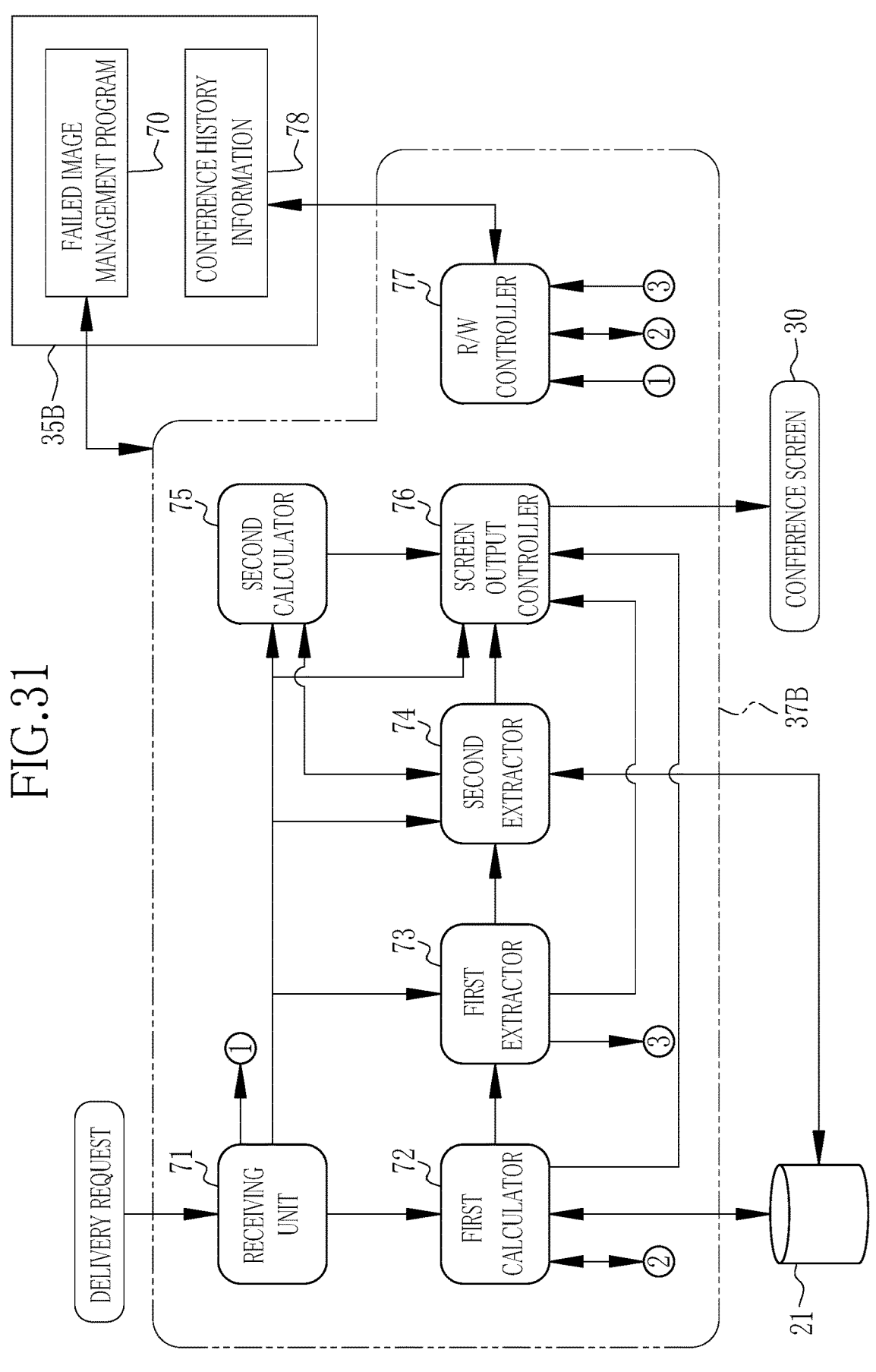
FIG. 31 is a block diagram illustrating the function of the CPU of the failed image management server according to a second embodiment.

In FIG. 31, Upon the startup of the failed image management program 70, a reading/writing (hereinafter abbreviated as R/W) controller 77 is established in the CPU 37B of the failed image management server 13, in addition to the respective components 71 to 76 of the first embodiment.

The R/W controller 77 controls writing and reading of conference history information 78 stored in the storage device 35B. The R/W controller 77 outputs the conference history information 78 to the first calculator 72.

The conference history information 78 is information representing the history of the conference held previously. Specifically, as shown in FIG. 32, the conference history information 78 consists of summary data 78A representing the summary of the previous conference and data 78B on the number of times of occurrence of imaging failure. The date of the previous conference, the staff IDs of the participants who attended the previous conference (hereinafter referred to as previous staff IDs), and the target menu extracted by the first extractor 73 at the previous conference (hereinafter referred to as previous target menu) are inputted in the summary data 78A. The data 78B on the number of times of occurrence of imaging failure represents the number of times of occurrence of imaging failure for each imaging menu in a period from the following day of the date of the last but one conference to the previous conference (hereinafter referred to as previous number of times of occurrence of imaging failure).

In FIG. 32, "2015.02.27" as the date of the previous conference, "R0001, R0004, R0007, R0008" as the previous staff ID, and "chest part/upright imaging posture/front, chest part/upright imaging posture/rear" as the previous target menu are illustrated by way of example. Additionally, as the previous number of times of occurrence of imaging failure, "15" corresponds to the imaging menu "chest part/upright imaging posture/front", and "30" corresponds to the imaging menu "chest part/upright imaging posture/rear".

Figure 33:
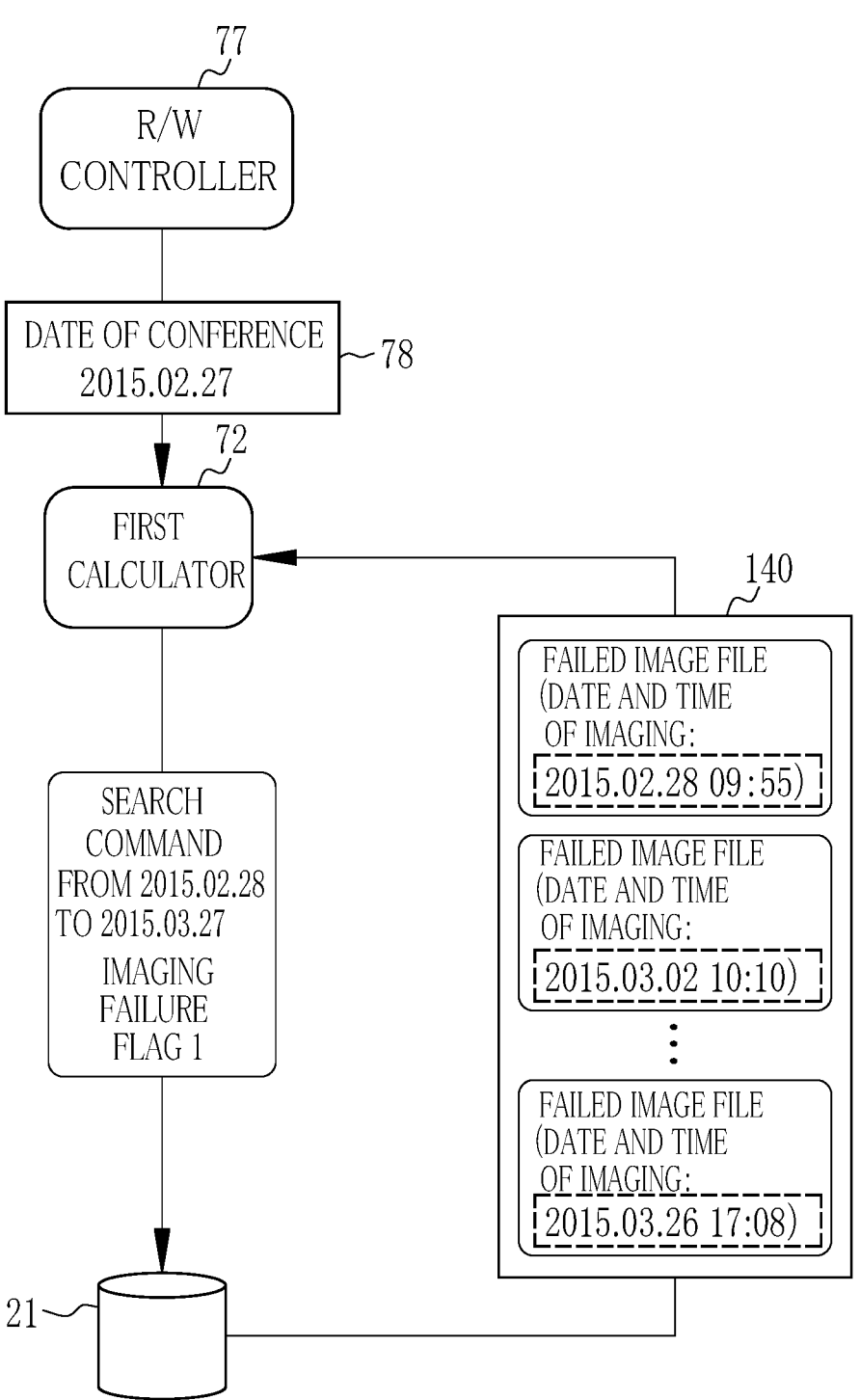
FIG. 33 illustrates that the first calculator acquires the failed image file.

In FIG. 33, the first calculator 72 outputs the search command designating the period and an imaging failure flag "1" (failed image file) to the imaging failure case example DB 21. In this case, the period designated by the search command is the period from the following day of the date of the previous conference inputted in the summary data 78A of the conference history information 78 from the R/W controller 77 to the date on which the delivery request is received by the receiving unit 71, namely, the date of the current conference (hereinafter referred to as previous-current period). The imaging failure case example DB 21 searches the failed image file, in which the date and time of imaging in the previous-current period is inputted, in response to the search command from the first calculator 72, and outputs a search result 140 to the first calculator 72.

Note that, in the case where the current conference is a conference held for the first time and the conference history information 78 is not stored in the storage device 35B, all the failed image files in the imaging failure case example DB 21 are outputted as the search result 140 from the imaging failure case example DB 21 to the first calculator 72.

In FIG. 33, the period from "2015.02.28" that is the following day of the date of the previous conference "2015.02.27" shown in FIG. 32 to "2015.03.27" that is the date of the current conference is illustrated as the previous-current period.

Therefore, the search result 140 consists of the failed image files in each of which the date and time of imaging icorresponding to the previous-current period "from 2015.02.28 to 2015.03.27" is inputted.

Figure 34:
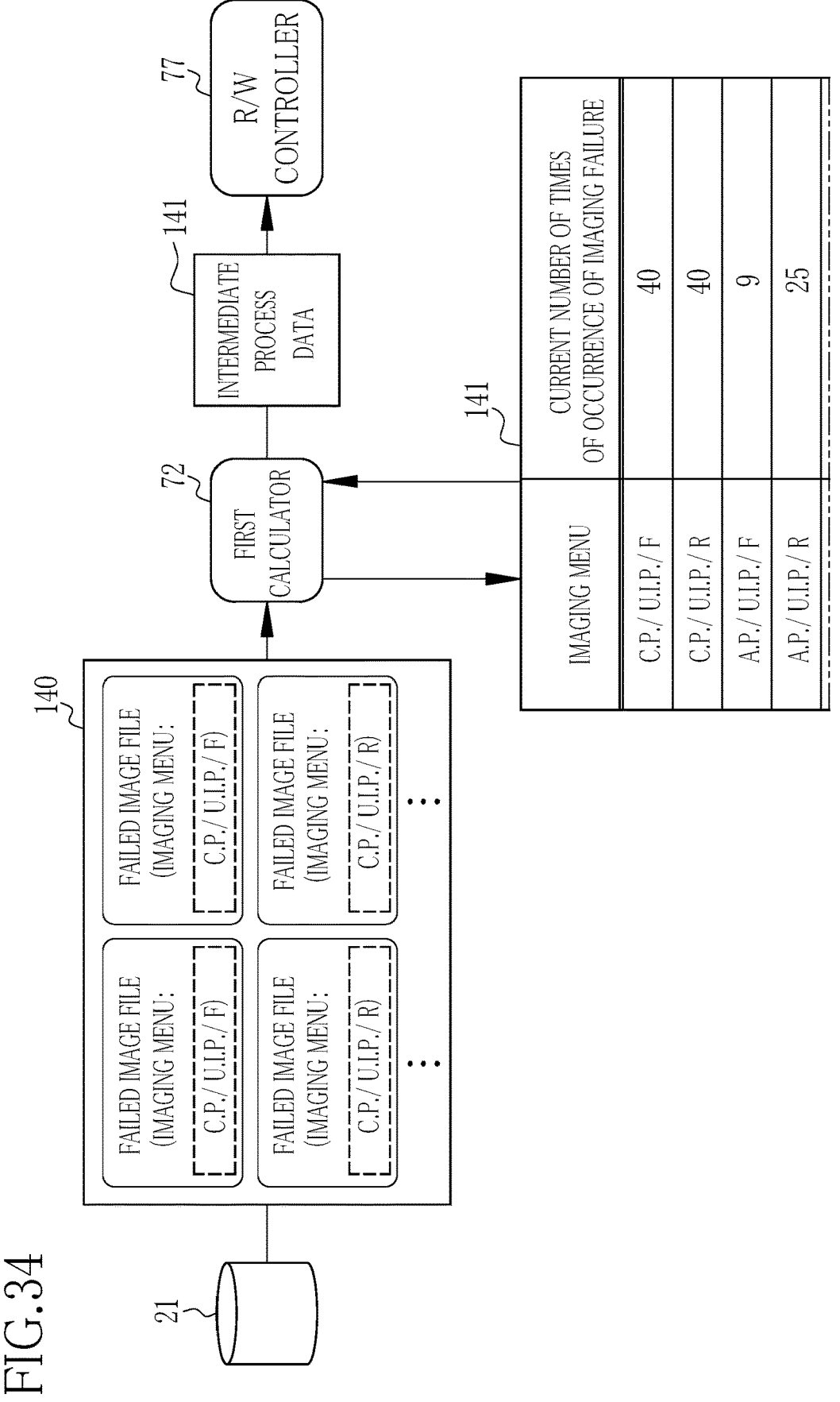
FIG. 34 illustrates that the first calculator counts the number of times of occurrence of imaging failure for each imaging menu.

In FIG. 34, the first calculator 72 generates intermediate process data 141 based on the search result 140. Specifically, the first calculator 72 focuses attention on the imaging menu of the failed image file of the search result 140, and counts the number of times of occurrence of imaging failure for each imaging menu based on the number of the failed image files for each imaging menu. For example, in the case of the imaging menu "chest part/upright imaging posture/front", "40" is counted as the number of times of occurrence of imaging failure. The number of times of occurrence of imaging failure thus counted is the number of times of occurrence of imaging failure for each imaging menu in the previous-current period (hereinafter, referred to as current number of times of occurrence of imaging failure). After counting the current number of times of occurrence of imaging failure, the first calculator 72 outputs the intermediate process data 141 to the R/W controller 77.

Figure 35:
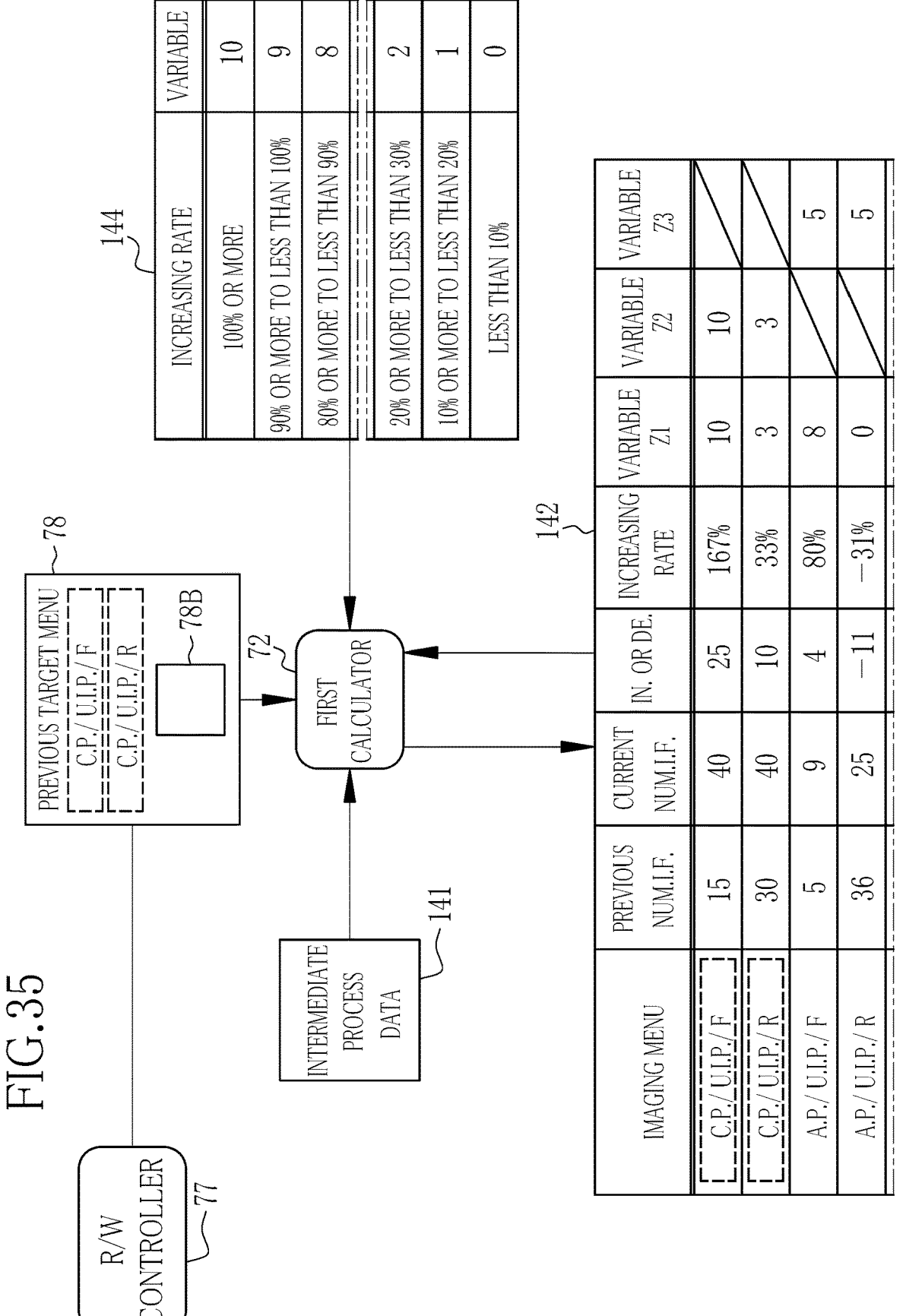
FIG. 35 illustrates that the first calculator derives variables based on an increasing rate of the number of times of occurrence of imaging failure for each imaging menu.

In FIG. 35, the first calculator 72 further generates intermediate process data 142 based on the conference history information 78 from the R/W controller 77 and the intermediate process data 141. Specifically, the first calculator 72 registers the previous number of times of occurrence of imaging failure from the data 78B on the number of times of occurrence of imaging failure of the conference history information 78, and the current number of times of occurrence of imaging failure from the intermediate process data 141, respectively in the intermediate process data 142. Then, the first calculator 72 calculates increment or decrement (abbreviated as "IN. OR DE." in the drawings) by subtracting the previous number of times of occurrence of imaging failure from the current number of times of occurrence of imaging failure, and divides the increment or decrement by the previous number of times of occurrence of imaging failure, so as to calculate an increasing rate, for each imaging menu.

In the case of the imaging menu "chest part/upright imaging posture/front", for example, the previous number of times of occurrence of imaging failure is "15", the current number of times of occurrence of imaging failure is "40", and the increment or decrement obtained by subtracting 15 from 40 equals to "25", and the increasing rate is expressed by 25/15×100≈167, namely approximately equals to "167%". In the case of the imaging menu "abdominal part/upright imaging posture/rear" (abbreviated as "A. P./U. I. P./R" in the drawings), the previous number of times of occurrence of imaging failure is "36", the current number of times of occurrence of imaging failure is "25", and the increment or decrement obtained by subtracting 36 from 25 equals to "−11", and therefore the increasing rate is expressed by −11/36×100≈−31, namely approximately equals to "−31%".

Subsequently, the first calculator 72 derives a variable Z1 based on the increasing rate of the number of times of occurrence of imaging failure for each imaging menu in accordance with a table 144 according to increasing rate and variable.

The table 144 according to increasing rate and variable is a data table in which the variable corresponding to the increasing rate is registered, and stored in the storage device 35B, for example. Here, a variable "10" for the increasing rate of 100% or more, a variable "9" for the increasing rate of 90% or more to less than 100%, . . . , a variable "2" for the increasing rate of 20% or more to less than 30%, and a variable "1" for the increasing rate of 10% or more to less than 20% are registered. Namely, the variable is decreased by one from "10" corresponding to the increasing rate of 100% for every 10%. A variable "0" is registered for the increasing rate of less than 10%.

In the case of the imaging menu "chest part/upright imaging posture/front", for example, the increasing rate is "167%", namely, in the range of 100% or more, and therefore "10" is derived as the variable Z1 and registered in the intermediate process data 142. In the case of the imaging menu "abdominal part/upright imaging posture/rear", the increasing rate is "−31%", namely in the range of less than 10%, and therefore "0" is derived as variable Z1 and registered in the intermediate process data 142.

Further, the first calculator 72 also derives a variable Z2 based on the increasing rate of the number of times of occurrence of imaging failure of the previous target menu in the summary data 78A of the conference history information 78 in accordance with the table 144 according to increasing rate and variable. The first calculator 72 derives the variable Z2 only for the imaging menu corresponding to the previous target menu among the imaging menus. Incidentally, how to derive the variable Z2 is the same as that of the variable Z1.

In FIG. 35, as the previous target menu, "chest part/ upright imaging posture/front, chest part/upright imaging posture/rear", which is the same as that in FIG. 32, is illustrated. As the variable Z2 of the imaging menu "chest part/upright imaging posture/front" corresponding to the previous target menu, "10" is derived as in the case of the variable Z1, and registered in the intermediate process data 142. Further, as the variable Z2 of the imaging menu "chest part/upright imaging posture/rear", "3" is derived as in the case of the variable Z1, and registered in the intermediate process data 142. Regarding the imaging menus "abdominal part/upright imaging posture/front" and "abdominal part/ upright imaging posture/rear", each of which does not correspond to the previous target menu, the variable Z2 is not derived as shown by diagonal lines in the drawing, and not registered.

Further, the first calculator 72 also derives a variable Z3 regarding the imaging menu which is not extracted as the previous target menu. The first calculator 72 derives the variable Z3 only for the imaging menu which does not correspond to the previous target menu among the imaging menus.

In FIG. 35, "5" is registered as the variable Z3, without exception, for the imaging menus "abdominal part/upright imaging posture/front" and "abdominal part/upright imaging posture/rear" each of which does not correspond to the previous target menu. The variable Z3 is not derived for the imaging menus "chest part/upright imaging posture/front" and "chest part/upright imaging posture/rear" each of which corresponds to the previous target menu as shown by diagonal lines in the drawing, and not registered.

Figure 36:
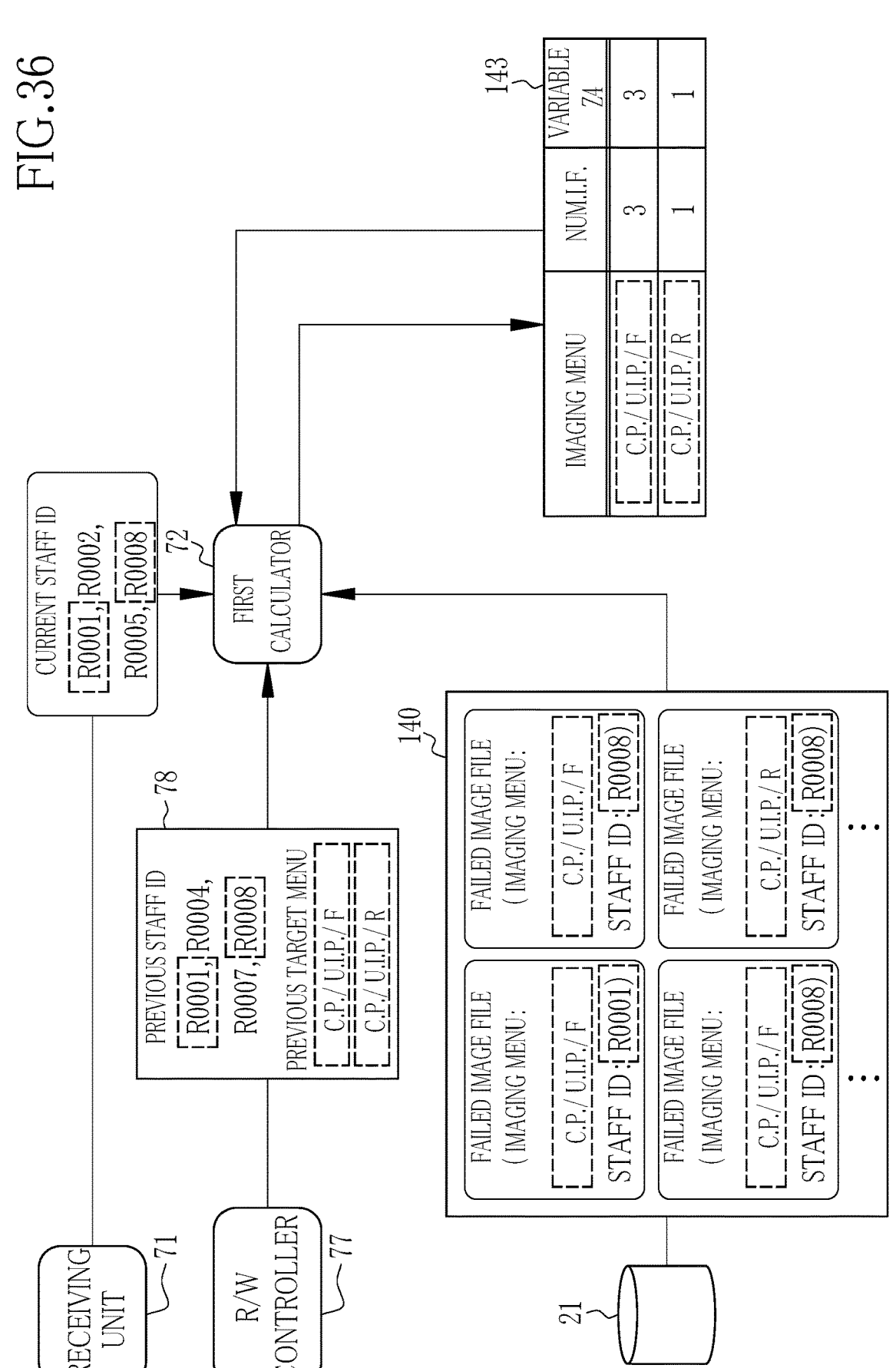
FIG. 36 illustrates that the first calculator derives variables based on whether or not a participant, who attended the previous conference and was designated to attend the current conference, failed in the imaging capturing corresponding to a target menu extracted at the previous conference.

In FIG. 36, the first calculator 72 receives the information regarding the current staff ID from the receiving unit 71. The first calculator 72 generates intermediate process data 143 based on the information regarding the current staff IDs, the information regarding the previous staff IDs and the previous target menu which is inputted in the summary data 78A of the conference history information 78 of the R/W controller 77, and the search result 140.

Specifically, the first calculator 72 focuses attention on the imaging menu of the failed image file of the search result 140 and the staff IDs, and counts the number of times of occurrence of imaging failure of the imaging menu corresponding to the previous target menu based on the imaging menu corresponding to the previous target menu and the number of failed image files in each of which the staff ID as both of the previous staff ID and the current staff ID is inputted.

The participant having the staff ID as both of the previous staff ID and the current staff ID is a participant who attended the previous conference and is designated to attend the current conference (hereinafter, referred to as consecutive participant). The number of times of occurrence of imaging failure thus counted is the number of times of occurrence of imaging failure for the imaging menu corresponding to the previous target menu made by the consecutive participant in the previous-current period.

After counting the number of times of occurrence of imaging failure, the first calculator 72 derives a variable Z4 based on whether or not the consecutive participant failed in the image capturing of the previous target menu. Here, as the variable Z4, a numerical value that is equal to the counted number of times of occurrence of imaging failure is derived. The first calculator 72 derives the variable Z4 only for the imaging menu corresponding to the previous target menu among the imaging menus.

In FIG. 36, as the current staff IDs, the staff IDs "R0001", "R0002", "R0005", and "R0008" are illustrated in the same manner as in FIG. 9. Additionally, as the previous staff IDs, the staff IDs "R0001", "R0004", "R0007", and "R0008" which are the same as those in FIG. 32 are illustrated, and as the previous target menu, the imaging menu "chest part/upright imaging posture/front, chest part/upright imaging posture/rear" which is the same as that in FIG. 32 is illustrated. The staff ID as both of the previous staff ID and the current staff ID is "R0001" and "R0008". Further, FIG. 36 illustrates the case where there are three failed image files in each of which the imaging menu "chest part/upright imaging posture/front" corresponding to the target menu and the staff ID "R0001" or "R0008" are inputted, and one failed image file in which the imaging menu "chest part/upright imaging posture/rear" corresponding to the target menu and the staff ID "R0008" are inputted, in the search result 140.

In this case, "3" is registered as the number of times of occurrence of imaging failure in the item of the imaging menu "chest part/upright imaging posture/front" in the intermediate process data 143, and "1" is registered as the number of times of occurrence of imaging failure in the item of the imaging menu "chest part/upright imaging posture/ rear" in the intermediate process data 143, respectively. Additionally, "3" is derived and registered as the variable Z4 for the imaging menu "chest part/upright imaging posture/front", and "1" is derived and registered as the variable Z4 for the imaging menu "imaging menu "chest part/upright imaging posture/rear", respectively. An item is not provided for the imaging menu which does not correspond to the previous target menu in the intermediate process data 143, and therefore the variable Z4 is not derived and not registered.

Figure 37:
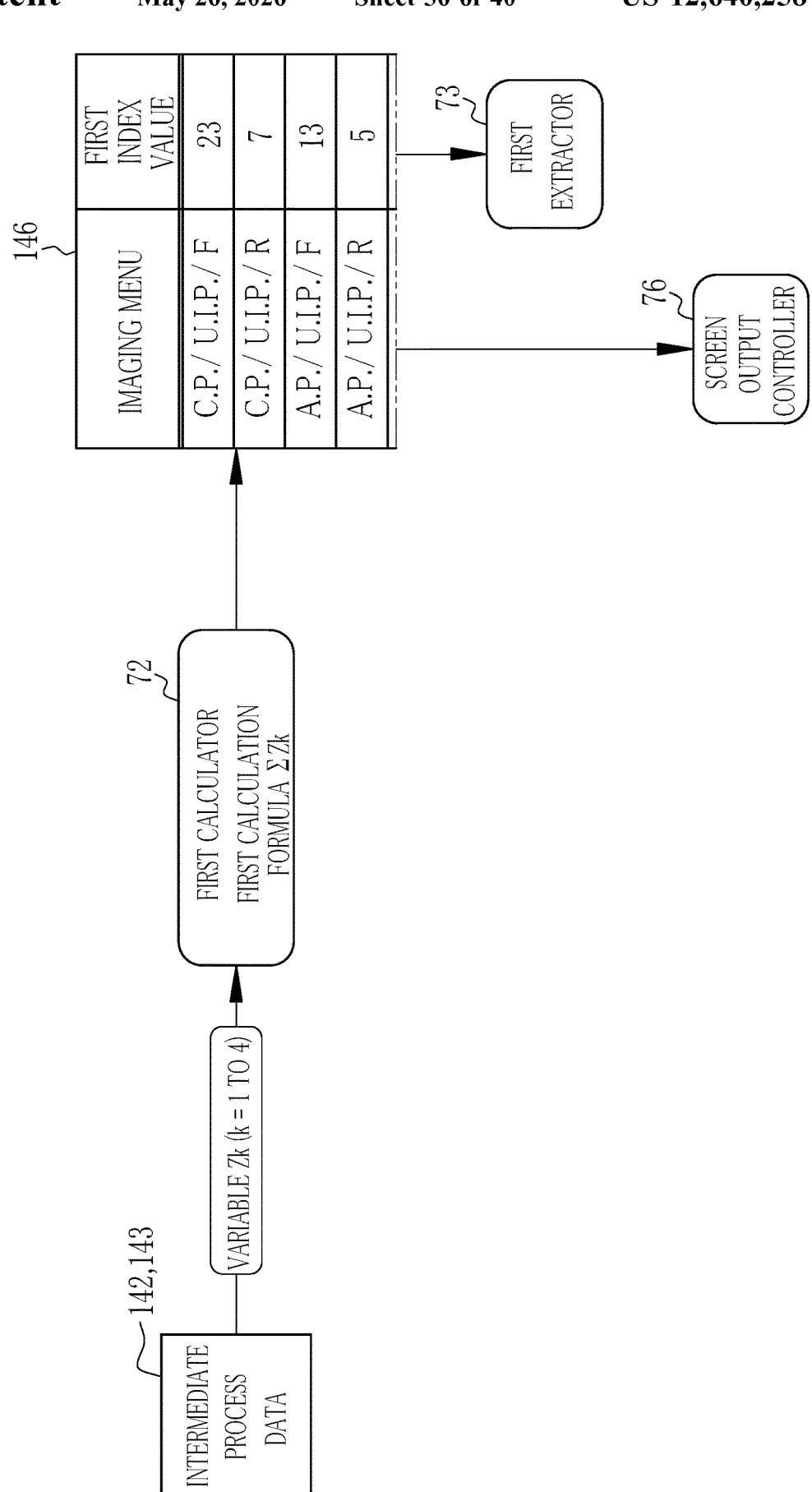
FIG. 37 is an explanatory view illustrating the function of the first calculator for calculating the first index value according to the second embodiment.

In FIG. 37, the first calculator 72 reads out each variable Zk (k=1 to 4) from each of the intermediate process data 142 and 143. The first calculator 72 calculates the first index value for each imaging menu using a first calculation formula $\Sigma Zk$ for obtaining summation of the variables Zk. The first calculator 72 outputs a calculation result 146 of the first index value to the first extractor 73 and the screen output controller 76.

The first index value may be calculated by adding or multiplying an adequate weighting coefficient to each variable Zk. For example, "10" is added to the variable Z1 based on the increasing rate of the number of times of occurrence of imaging failure for each imaging menu. Alternatively, the variable Z4 based on whether or not the consecutive participant failed in the image capturing corresponding to the previous target menu is multiplied by "2". In this case, the weighting coefficient may be configured to be settable on the client terminal 12.

The subsequent process is approximately the same as that of the above first embodiment, and therefore only the difference in the process between this embodiment and the above first embodiment is described hereinbelow.

Firstly, the first extractor 73 adds the extraction result 91 of the extracted target menu to the second extractor 74 and the screen output controller 76, and outputs it to the R/W controller 77.

Figure 38:
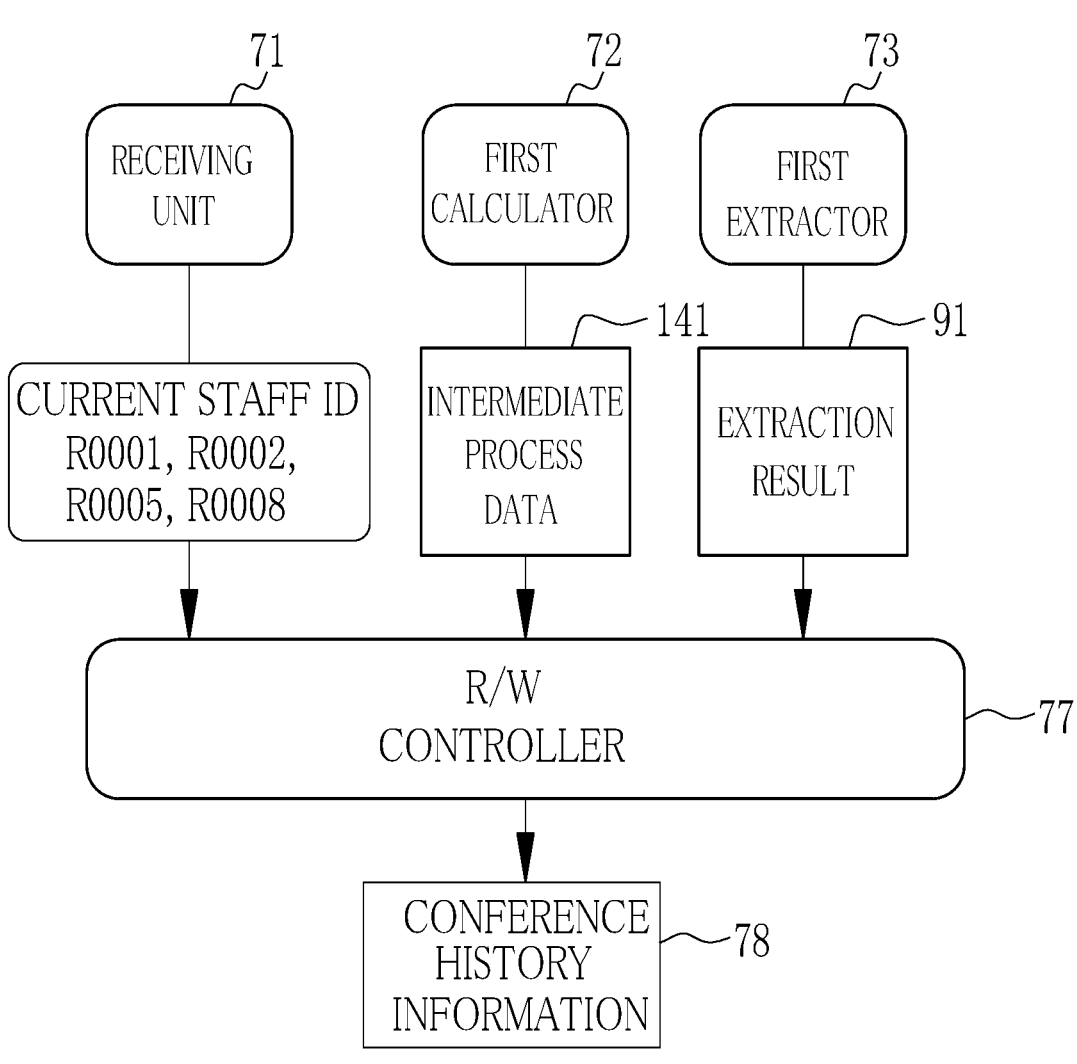
FIG. 38 illustrates that a R/W controller updates the conference history information.

Further, as shown in FIG. 38, the R/W controller 77 receives the information regarding the current staff ID from the receiving unit 71, the intermediate process data 141 of the current number of times of occurrence of imaging failure from the first calculator 72, and the extraction result 91 of the target menu from the first extractor 73. The R/W controller 77 updates the conference history information 78 based on the information regarding the current staff IDs, the intermediate process data 141, and the extraction result 91.

Specifically, the R/W controller 77 rewrites the date of the previous conference in the summary data 78A to the date on which the delivery request was received by the receiving unit 71, namely, the date of the current conference, rewrites the previous staff IDs to the current staff IDs received from the receiving unit 71, and rewrites the previous target menu to the target menu of the extraction result 91. Further, the R/W controller 77 replaces the data 78B on the number of times of occurrence of imaging failure with the intermediate process data 141.

According to this embodiment, the first index value is calculated using the first calculation formula $\Sigma Zk$ having the variable Z1 based on the increasing rate of the number of times of occurrence of imaging failure for each imaging menu. Therefore, the first index value is based on the increasing rate of the number of times of occurrence of imaging failure for each imaging menu. Consequently, the first index value makes it possible to know exactly the imaging failure state for each imaging menu.

The first calculation formula $\Sigma Zk$ has not only the variable Z1 but also the variable Z2 based on the increasing rate of the number of times of occurrence of imaging failure of the previous target menu. Therefore, the first index value is based on the imaging failure state of the previous target menu in the previous-current period.

Further, the first calculation formula $\Sigma Zk$ also has the variable Z3 regarding the imaging menu which was not extracted as the previous target menu. Therefore, the first index value is also based on the imaging menu which does not correspond to the previous target menu.

Furthermore, the first calculation formula $\Sigma Zk$ has the variable Z4 based on whether or not the consecutive participant failed in the image capturing of the previous target menu. Therefore, the first index value is also based on whether or not the consecutive participant failed in the image capturing of the imaging menu corresponding to the previous target menu in the previous-current period.

According to this embodiment, the first index value is the summation of the variables Zk as expressed by the first calculation formula $\Sigma Zk$. Therefore, as the increasing rate of the number of times of occurrence of imaging failure is higher and the variable Zk is larger, namely, as the increasing rate of the frequency of imaging failure is higher, the first index value is increased and the first index value is ranked at higher place. Consequently, the imaging menu having the first index value of which rank is relatively high is an imaging menu of which increasing rate of the frequency of imaging failure is relatively high.

According to this embodiment, since the imaging menu having the first index value of which rank is relatively high is automatically extracted as the target menu by the first extractor 73, the imaging menu of which increasing rate of the frequency of imaging failure is relatively low is extracted and designated. Therefore, there is no fear that useless consideration is performed and results in waste of precious time of the medical staff members, and it becomes possible for the medical staff members to perform the consideration for reliably suppressing the increase in the frequency of imaging failure.

Further, since the target menu is automatically extracted, it is unnecessary for the medical staff members to know exactly the imaging failure state for each imaging menu in order to extract and designate the imaging menu of which increasing rate of the frequency of imaging failure is relatively high. Consequently, it is possible to decrease a burden on each of the medical staff members, such that the medical staff members can sufficiently consider improvement on the image capturing.

In the case where the increasing rate of the number of times of occurrence of imaging failure of the previous target menu extracted at the previous conference becomes relatively lower at the current conference, it is represented that the consideration at the previous conference was useful and the imaging skill for the previous target menu has been improved. In contrast, in the case where the increasing rate of the number of times of occurrence of imaging failure of the previous target menu extracted at the previous conference becomes relatively higher at the current conference, it is represented that the consideration at the previous conference was not sufficient and the imaging skill for the previous target menu has not been improved yet.

In the case where the increasing rate of the number of times of occurrence of imaging failure of the previous target menu becomes relatively higher at the current conference, it is preferable that the previous target menu is extracted as the target menu also at the current conference and the radiographic image 26, which was obtained by the failed image capturing of the imaging menu corresponding to the previous target menu is viewed as the consideration image 26C, because the consideration can be consecutively performed from the previous conference and the improvement on the image capturing can be studied again.

In this embodiment, the first index value is based on the imaging failure state of the previous target menu in the previous-current period using the variable Z2 as described above. Therefore, the previous target menu, in which the increasing rate of the number of times of occurrence of imaging failure is relatively high, has the first index value ranked at higher place, and tends to be frequently extracted as the target menu by the first extractor 73. Consequently, the probability of the radiographic image 26 obtained by the failed image capturing of the imaging menu corresponding to the previous target menu being viewed as the consideration image 26C is increased.

In contrast, in the case where the increasing rate of the number of times of occurrence of imaging failure of the previous target menu becomes relatively lower at the current conference, it is preferable that not the previous target menu but the imaging menu which does not correspond to the previous target menu is extracted as the target menu and the radiographic image 26 obtained by the failed image capturing of the imaging menu which does not correspond to the previous target menu is viewed as the consideration image 26C at the current conference, because it is possible to prevent the increase in the frequency of imaging failure for each imaging menu equally for each imaging menu.

In this embodiment, the first index value is based on the imaging menu which does not correspond to the previous target menu using the variable Z3 as described above. Therefore, in the case where the increasing rate of the number of times of occurrence of imaging failure of the previous target menu becomes relatively lower at the current conference, the imaging menu which does not correspond to the previous target menu has the first index value ranked at higher place, and tends to be extracted frequently as the target menu by the first extractor 73. Consequently, the probability of the radiographic image 26 obtained by the failed image capturing of the imaging menu which does not correspond to the previous target menu being viewed as the consideration image 26C is increased.

Further, in the case where the consecutive participant failed in the image capturing of the imaging menu corresponding to the previous target menu in the previous-current period, it is represented that the consideration at the previous conference was not sufficient and the imaging skill of the consecutive participant has not been improved yet.

In such a case, in order to prevent a situation that the consecutive participant repeats the failure hereafter and the increasing rate of the frequency of imaging failure is increased, the necessity of considering improvement on the image capturing is high. Therefore, it is preferable that the radiographic image 26 obtained in the failed image capturing of the imaging menu corresponding to the previous target menu by the consecutive participant in the previous-current period is viewed as the consideration image 26C.

In this embodiment, the first index value is based on whether or not the consecutive participant failed in the image capturing of the imaging menu corresponding to the previous target menu in the previous-current period using the variable Z4 as described above. Therefore, the previous target menu, for which the number of times of occurrence of imaging failure made by the consecutive participant in the previous-current period is larger, has the first index value ranked at higher place, and tends to be extracted frequently as the target menu by the first extractor 73. Consequently, the probability of the radiographic image 26 obtained by the failed image capturing of the imaging menu corresponding to the previous target menu by the consecutive participant in the previous-current period being viewed as the consideration image 26C is increased.

Further, also in this embodiment, as in the case of the above first embodiment, the target menus are arranged in descending order of the first index value in the target menu display region 110. Furthermore, the thumbnails 121 of the consideration images 26C are arranged in descending order of the second index value in the consideration image selection region 120. In the case where there are two or more target menus or consideration images 26C, it is possible to easily find and select the target menu or the consideration image 26C which is highly beneficial in sufficiently suppressing the increasing rate of the frequency of imaging failure.

Third Embodiment

Note that, in the case where there are no staff IDs of the participants (referred to as current staff IDs in the second embodiment) in the failed image file of the search result 95 searched by the second extractor 74 based on the target menu, it turns out that the consideration images 26C all of which were captured by a person other than the participants are viewed. As described above, at the conference, not the radiographic image 26 captured by a person other than the participants but the radiographic image 26 captured by the participant is preferably viewed as the consideration image 26C, and therefore it is not a preferable situation that the consideration images 26C all of which were captured by a person other than the participants are viewed.

Accordingly, in this embodiment, in the case where there are no staff IDs of the participants in the failed image file of the search result 95, the second extractor 74 replaces the target menu with another one to search the failed image file again. Until the failed image file in which the staff ID of the participant is inputted is retrieved, the replacement of the target menus and the search for the failed image file are repeated.

In this case, the receiving unit 71 outputs the information regarding the staff IDs of the participants to the second extractor 74. As illustrated in step S500 of FIG. 39, the second extractor 74 receives the information regarding the staff IDs of the participants from the receiving unit 71. As with the case shown in FIG. 19, the second extractor 74 searches the failed image file, in which the imaging menu that is the same as the target menu is inputted, from the imaging failure case example DB 21 (step S510). Then, the second extractor 74 compares the staff ID sinputted in the searched failed image file with the staff IDs of the participants received from the receiving unit 71 (step S520).

As a result of the comparison, there are no failed image files, in each of which the staff IDs of the participants are inputted, among the searched failed image files (NO in step S530), the target menu used to search the failed image file in step S510 is replaced with another target menu (step S540). Thereafter, the new target menu is used to search the failed image file again in step S510.

Until the failed image file in which the staff ID of the participant is inputted is retrieved (YES in step S530), the second extractor 74 repeats the replacement of the target menus in step S540 and the search for the failed image file in step S510.

The target menu replaced by the second extractor 74 is an imaging menu having the first index value ranked at first place among the imaging menus which were not extracted as the target menu by the first extractor 73, for example. By referring to FIG. 18 as an example, in the case where there is no staff ID of the participant in the failed image file in which the imaging menu "chest part/upright imaging posture/front" having the first index value ranked at first place is inputted, the imaging menu is replaced with the imaging menu "cephalic part/sitting imaging posture/front" having the first index value ranked at second place, and the failed image file is searched again. In the case where there is no staff ID of the participant in the searched failed image file in which the imaging menu "cephalic part/sitting imaging posture/front" having the first index value ranked at second place is inputted, the imaging menu is replaced with the imaging menu "abdominal part/upright imaging posture/rear" having the first index value ranked at third place, and the failed image file is searched again.

As a result, since there is inevitably the radiographic image 26 captured by the participant as the consideration image 26C, it is possible to avoid the situation that the consideration images 26C all of which were captured by a person other than the participants are viewed. Incidentally, in this case, there is a fear that the imaging menu having the first index value ranked at relatively lower place is retrieved as the target menu as a result of the replacement of the target menus, and therefore a mark for indicating that the target menu is a replaced one may be displayed in the display field 110B of the target menu display region 110, for example, so as to draw participant's attention.

Forth Embodiment

In the case where there are two or more target menus extracted by the first extractor 73, in comparison between the target menu having the first index value ranked at relatively higher place and the target menu having the first index value ranked at relatively lower place, the frequency of imaging failure or the increasing rate of the frequency of imaging failure is higher and the imaging failure state is poor in the target menu having the first index value ranked at relatively higher place. Therefore, the consideration image 26C of the target menu having the first index value ranked at relatively higher place is preferably viewed, such that the effect of decreasing the frequency of imaging failure or suppressing the increase in the frequency of imaging failure is achieved.

Accordingly, in this embodiment, the number of the consideration images 26C to be extracted by the second extractor 74 is increased for the failed image file corresponding to the target menu having the first index value ranked at relatively higher place and worse imaging failure state.

In this case, the second extractor 74 generates intermediate process data 145 shown in FIG. 40. An allocation rate of the number of the failed image files to be extracted as the consideration images 26C (the number of the consideration images 26C to be extracted) for each of three target menus 1, 2, and 3, for example, is calculated based on the first index value and registered in the intermediate process data 145. Incidentally, the target menu 1 has the first index value of "100" ranked at first place, the target menu 2 has the first index value of "70" ranked at second place, and the target menu 3 has the first index value of "30" ranked at third place.

The allocation rate of the number of the failed image files to be extracted as the consideration image 26C is calculated by dividing the first index value of each of the target menus 1 to 3 by summation of the first index values of the target menus 1 to 3. In this case, the first index value of each of the target menus 1 to 3 is "100, "70", and "30", respectively, and the summation of the first index values of the target menus 1 to 3 is expressed by 100+70+30, namely equals to 200. Accordingly, the allocation rate for the target menu 1 is expressed by (100/200)×100, namely equals to 50%. In the similar manner, the allocation rate for the target menu 2 is 35%, and the allocation rate for the target menu 3 is 15%.

In the case where "100" is designated as the number of the consideration images 26C on the designation screen 50, as shown in FIG. 40, the number of the consideration images 26C to be extracted for the target menu 1 is expressed by 100×0.5, namely equals to "50". In the similar manner, the number of the consideration images 26C to be extracted for the target menu 2 is "35", and the number of the consideration images 26C to be extracted for the target menu 3 is "15".

The second extractor 74 extracts the failed image file of each of the target menus 1 to 3 based on the intermediate process data 145. Thus, for the target menu in which the frequency of imaging failure can be decreased, or for the target menu in which the increase in the frequency of imaging failure can be suppressed, the number of the consideration images 26C to be extracted becomes larger, and therefore it is possible to perform meaningful consideration and promote the decrease in the frequency of imaging failure or the suppression of the increase in the frequency of imaging failure.

The number of consideration image 26C to be extracted is not necessarily calculated based on the first index value. For example, in the case where the number of target menus extracted by the first extractor 73 is "9", and "45" is designated as the number of consideration images 26C on the designation screen 50, the number of the consideration images 26C to be extracted for the target menu having the first index value ranked at first place may be set to "9", the number of the consideration images 26C to be extracted for the target menu having the first index value ranked at second place may be set to "8", . . . , the number of the consideration images 26C to be extracted for the target menu having the first index value ranked at eighth place may be set to "2", and the number of the consideration images 26C to be extracted for the target menu having the first index value ranked at ninth place may be set to "1", namely, the number of the consideration images 26C to be extracted may be decreased by one as the rank of the first index value is decreased. Further, in the case where the number of the target menus is two, the allocation rate for the target menu having the first index value ranked at first place may be set to 70%, and the allocation rate for the target menu having the first index value ranked at second place may be set to 30%, namely the allocation rate may be preliminarily set in accordance with the number of the target menus.

Note that, as shown in FIG. 41, a check box 150 for designating a particularly notable participant may be disposed next to the icon 115 of each participant in the participant display region 111 of the conference screen 30. In the case where the check box 150 is selected using the cursor 56, the extraction of the target menu and consideration image 26C may be performed by the failed image management server 13 again.

In this case, in the failed image management server 13, at the time of calculating the first index value by the first calculator 72, a weighting coefficient that is more than 0 is added to the variable based on the number of times of occurrence of imaging failure and the variable based on the rate of occurrence of imaging failure of the participant of which check box 150 is selected using the cursor 56.

Alternatively, the variable based on the number of times of occurrence of imaging failure and the variable based on the rate of occurrence of imaging failure of the participant of which check box 150 is selected using the cursor 56 are multiplied by a weighting coefficient more than 1. In FIG. 41, the check box 150 corresponding to "Ayaka HYAKUYASU" having the staff ID "R0008" is selected, and therefore a weighting coefficient more than 0 is added to the variable X9 based on the number of times of occurrence of imaging failure and the variable X10 based on the rate of occurrence of imaging failure corresponding to the staff ID "R0008" shown in FIG. 14, or the variables X9 and X10 are multiplied by a weighting coefficient more than 1. Alternatively, a weighting coefficient more than 0 is added to the variable Z4 of the imaging menus "chest part/upright imaging posture/front" and "chest part/upright imaging posture/rear" shown in FIG. 36, or the variable Z4 is multiplied by a weighting coefficient more than 1.

Furthermore, when the second calculator 75 calculates the second index value, a weighting coefficient more than 0 is added to the variable Y1 regarding the participant of the failed image file, in which the staff ID of the participant of which check box 150 is selected using the cursor 56 is inputted, or the variable Y1 is multiplied by a weighting coefficient more than 1.

As described above, the target menu and the consideration image 26C are extracted again such that the contribution ratio of the variable regarding the participant of which check box 150 is selected using the cursor 56 to the first index value and the second index value is increased. Thereby, probability of the imaging menu that the participant of which check box 150 was selected using the cursor 56 failed in the image capturing, and the failed image captured by the participant of which check box 150 was selected using the cursor 56 being extracted as the target menu and the consideration image 26C is increased, respectively.

Figure 42:
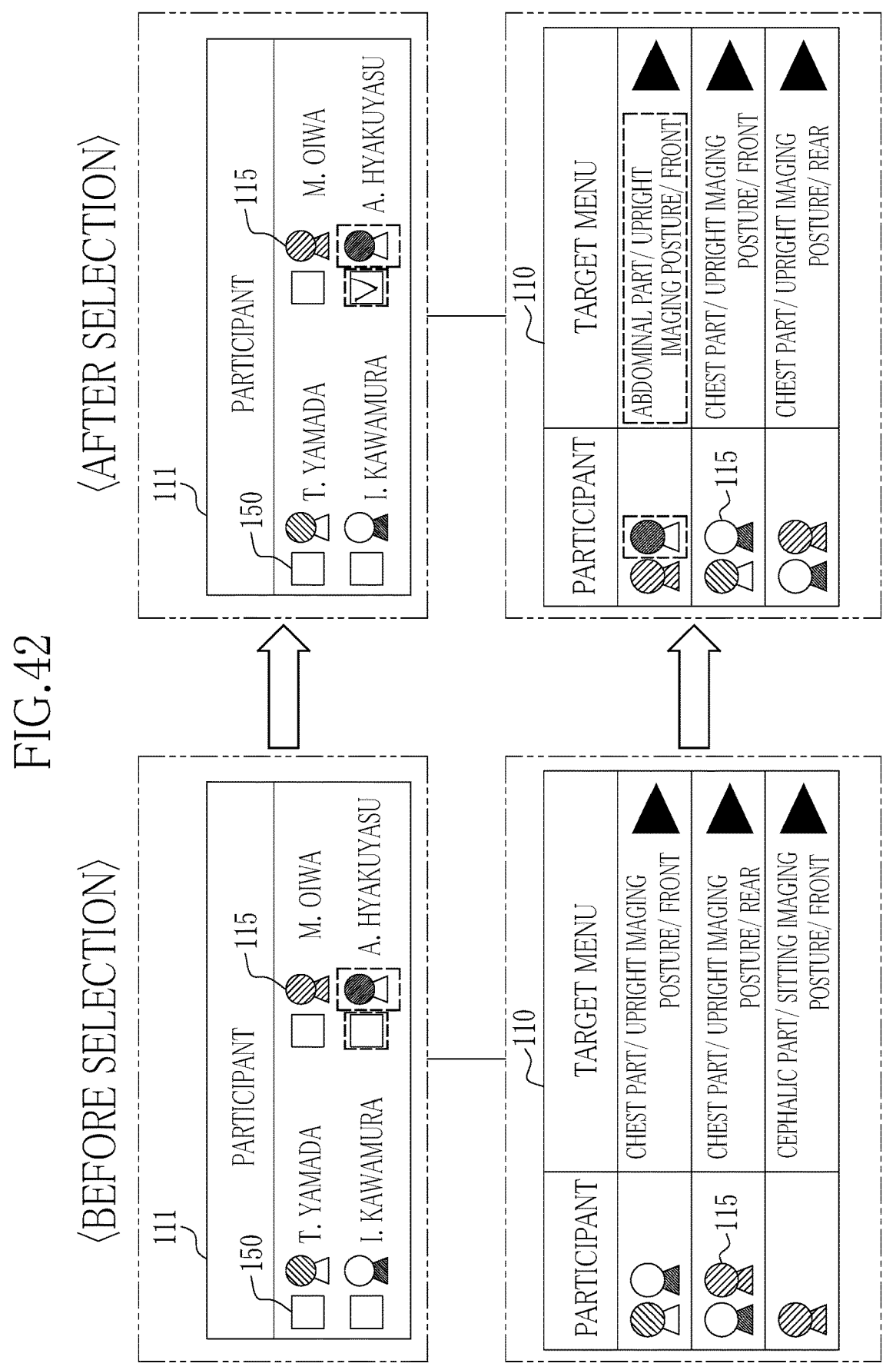
FIG. 42 illustrates an example of a display state of a target menu display region before and after selection of a check box for designating a particularly notable participant.

For example, FIG. 42 illustrates a display state of the target menu display region 110 before and after selection of the check box 150. In this case, before the check box 150 corresponding to "Ayaka HYAKUYASU" is selected, the target menu containing the consideration image 26C captured by "Ayaka HYAKUYASU" is not displayed in the target menu display region 110. In contrast, after the selection of the check box 150 corresponding to "Ayaka HYAKUYASU", the contribution ratio of the variable regarding "Ayaka HYAKUYASU" to the first index value is increased, and thereby the target menu "abdominal part/upright imaging posture/front" containing the consideration image 26C captured by "Ayaka HYAKUYASU" is displayed at the top of the target menu display region 110.

Figure 43:
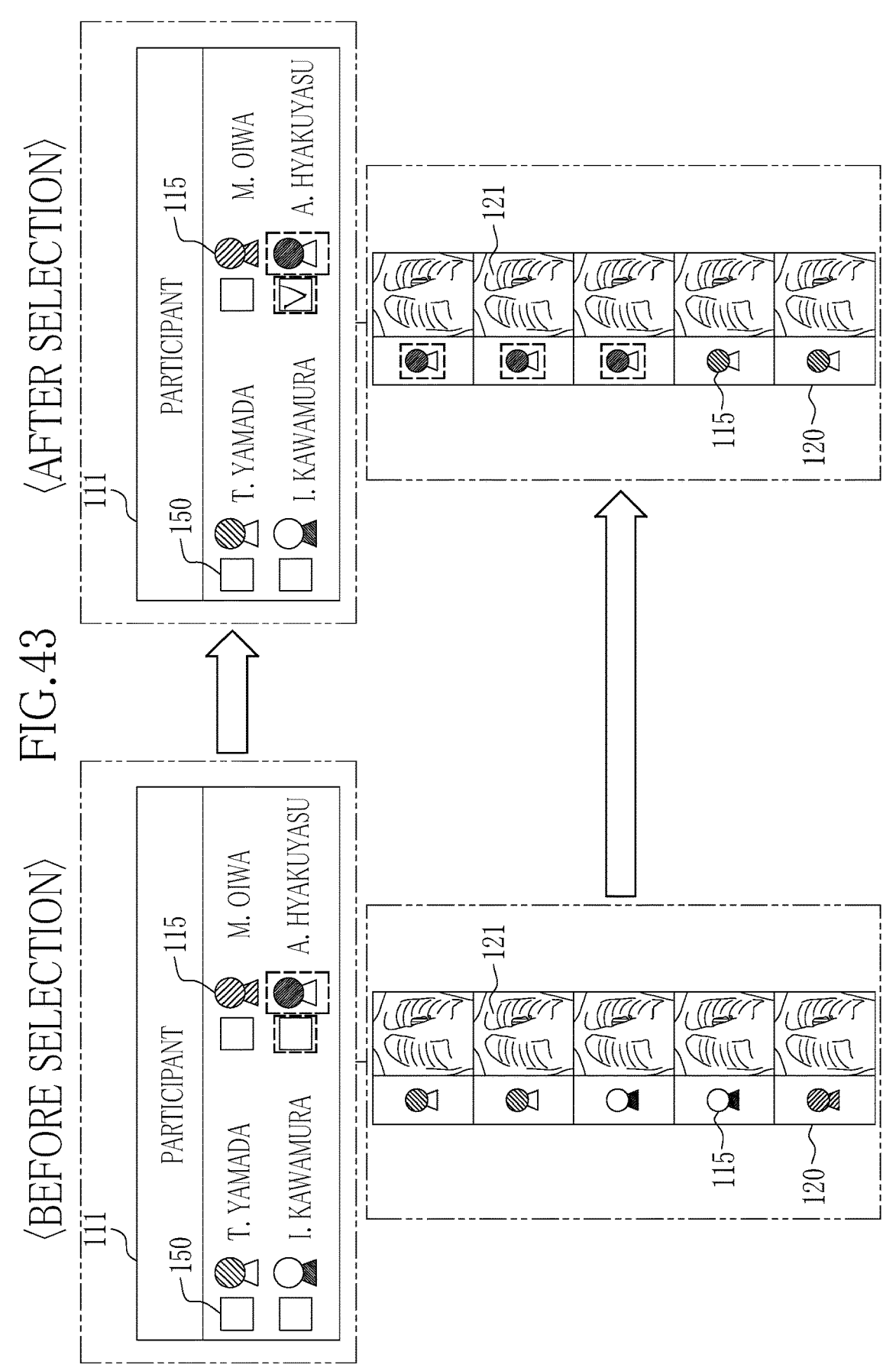
FIG. 43 illustrates an example of a display state of the consideration image selection region before and after selection of a check box for designating a particularly notable participant.

Further, for example, FIG. 43 illustrates a display state of the consideration image selection region 120 before and after the selection of the check box 150. In this case, before the check box 150 corresponding to "Ayaka HYAKUYASU" is selected, the thumbnail 121 of the consideration image 26C captured by "Ayaka HYAKUYASU" is not displayed in the consideration image selection region 120. In contrast, after the selection of the check box 150 corresponding to "Ayaka HYAKUYASU", the contribution ratio of the variable regarding "Ayaka HYAKUYASU" to the second index value is increased, and thereby a series of three thumbnails 121 of the consideration images 26C captured by "Ayaka HYAKUYASU" are displayed from the top in the consideration image selection region 120.

Note that, a function of the check box 150 for designating the particularly notable participant may be provided in the participant selection region 51 of the designation screen 50.

However, it is preferable that the check box 150 is provided in the participant display region 111 of the conference screen 30 as shown in FIG. 41, because it is possible to promptly respond to the case where the failed image corresponding to the particularly notable participant is required to be considered in the middle of the conference, thus resulting in high convenience.

In the above first embodiment, the narrowing-down condition is used only for the calculation of the second index value. However, the narrowing-down condition may be contained in the search command at the time of searching the diagnostic image file and the failed image file by the first calculator 72 as shown in FIG. 11, at the time of searching the failed image file by the second extractor 74 as shown in FIG. 19, and at the time of searching the diagnostic image file by the second extractor 74 as shown in FIG. 23.

It is sufficient that the first calculation formula has at least the variable X1 based on the number of times of occurrence of imaging failure for each imaging menu and the variable X2 based on the rate of occurrence of imaging failure for each imaging menu, or the variable Z1 based on the increasing rate of the frequency of imaging failure for each imaging menu. Further, it is sufficient that the second calculation formula has at least the variable Y1 based on whether or not the failed image as the consideration image 26C is associated with the participant.

The first calculation formula and the second calculation formula are not limited to the summation ΣXi of the variables Xi, the summation ΣYj of the variables Yj, and the summation ΣZk of the variables Zk, as described in the first and second embodiments by way of example. For example, an infinite product πXi of the variables Xi, an infinite product πYj of the variables Yj, and an infinite product πZk of the variables Zk may be used. Further, the variable Xi becomes larger as the number of times of occurrence of imaging failure is increased or as the rate of occurrence of imaging failure is increased in each of the above embodiments. However, in contrast, the variable Xi may be larger as the number of times of occurrence of imaging failure is decreased or as the rate of occurrence of imaging failure is decreased. In the similar manner, the variable Zk may be larger as the increasing rate of the frequency of imaging failure or the like is decreased.

Various modifications are possible for the hardware configuration of the computer constituting the failed image management server 13 corresponding to the failed image management apparatus of the present invention. For example, the failed image management server 13 may consist of a plurality of server computers separated as the hardware, for the purpose of improving ability of processing and reliability.

Specifically, the functions of the receiving unit 71, the first calculator 72, and the first extractor 73, and the functions of the second extractor 74, the second calculator 75, and the screen output controller 76 are dispersedly assumed by two server computers. In this case, the two server computers constitute the failed image management system. The server computer having the functions of the receiving unit 71, the first calculator 72, and the first extractor 73 outputs the calculation result 86 of the first index value and the extraction result 91 of the target menu to the server computer having the functions of the second extractor 74, the second calculator 75, and the screen output controller 76.

Further, all the functional components 71 to 76 may be established in the CPU 37A of the client terminal 12, such that the client terminal 12 operates as the failed image management apparatus. Alternatively, part of the functional components 71 to 76 may be established in the CPU 37A of the client terminal 12. In this case, the client terminal 12 and the failed image management server 13 constitute the failed image management system.

In the case where all the functional components 71 to 76 are established in the CPU 37A of the client terminal 12, the client terminal 12 issues search requests corresponding to the search command of the diagnostic image file and the failed image file shown in FIG. 11, the search command of the failed image file shown in FIG. 19, and the search command of the diagnostic image file shown in FIG. 23, to the failed image management server 13. The failed image management server 13 outputs the search results 80, 95, and 105 to the client terminal 12 in response to the search requests.

The receiving unit 71 established in the CPU 37A of the client terminal 12 receives the search results 80, 95, and 105 from the failed image management server 13, and receives the delivery command from the GUI controller 45. Further, the screen output controller 76 established in the CPU 37A of the client terminal 12 generates the conference screen 30, and outputs the generated conference screen 30 to the GUI controller 45.

Alternatively, the imaging failure case example DB 21 may be established in the PACS 11, such that the PACS 11 manages not only the diagnostic image file but also the failed image file and the PACS 11 assumes the function of the failed image management apparatus.

As described above, the hardware configuration of the computer may be appropriately changed in accordance with the required properties such as the ability of processing, safety, and reliability. Further, as a matter of course, not only the hardware but also the application programs such as the failed image management program 70 may be duplicated or dispersedly stored in a plurality of storage devices, for the purpose of securing the safety and reliability.

The means for providing the target menus and the consideration images 26c to the medical staff members is not limited to the delivery of the conference screen 30 using the web described in each of the above embodiments. For example, a DB for storing a consideration file in which the target menus and the consideration images 26C are recorded may be provided, and the access authority to the DB may be given to the medical staff members, such that each of the medical staff members reads out the consideration file from the DB. A publicly-known file transfer protocol such as FTPS (File Transfer Protocol over SSL/TLS) may be used to automatically transmit the consideration file to the client terminal 12. Instead of the file transfer protocol, e-mail may be used. Further, a paper material on which the target menus and the consideration images 26C are printed may be outputted.

According to each of the above embodiments, the medical information system 2 established in one medical facility is described by way of example, and the failed image management server 13 is used in one medical facility. However, the failed image management server 13 may be used in a plurality of medical facilities.

According to each of the above embodiments, the client terminal 12 installed in one medical facility is communicably connected to the failed image management server 13 using the network 14 such as the LAN, such that various functions in response to various requests from the client terminal 12 are provided. For the purpose of using the various functions in a plurality of medical facilities, the failed image management server 13 is communicably connected to the client terminals 12 installed in a plurality of medical facilities using WAN (Wide Area Network) such as the internet and public telecommunication network. Then, the request from each of the client terminals 12 in a plurality of medical facilities is received by the failed image management server 13 using the WAN, and various functions are provided to each of the client terminals 12. Incidentally, in the case of using the WAN, by taking the information security into consideration, it is preferable that VPN (Virtual Private Network) is established, or a communication protocol at a high security level such as HTTPS (Hypertext Transfer Protocol Secure) is used.

In this case, the failed image management server 13 may be installed in and managed by a data center managed by a company independent from the medical facility or one of the medical facilities.

Although the radiographic image captured by the radiation imaging system 10 is exemplified as the medical image in each of the above embodiments, the medical image may be an MRI image captured by an MRI imaging system or the like. Further, the radiographic image 26 and the accompanying information are not necessarily organized in a file format in the similar manner as the image file. Furthermore, it is described that one diagnostic image file corresponds to one imaging order, however a plurality of diagnostic image files may correspond to one imaging order.

Furthermore, although the failed image file and the diagnostic image file are stored in one imaging failure case example DB 21, a DB for storing the failed image file and a DB for storing the diagnostic image file may be separately provided.

According to the above first embodiment, as the situation of the consideration, the conference at which a plurality of the medical staff members gather is exemplified. However, as a matter of course, the present invention is also applicable to personal consideration by one medical staff member. In this case, the client terminal 12 is preferably a portable terminal such as a mobile phone, smartphone, tablet, PDA (Personal Digital Assistant), and laptop. Thereby, regardless of date, time, and place, consideration can be repeatedly performed, and spare time such as a time interval between image capturing operations and commuting hours can be used for the consideration.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A failed image management apparatus comprising at least one processor configured to:

calculate, for each of a plurality of medical imaging menus, a first index value based on both a number and a rate of plurality of failed images occurring for the each medical imaging menu;

calculate, for each of the failed images, a second index value based on information associated with a medical staff member and a patient corresponding to each failed image;

automatically extract and display, on the basis of the first index value, at least one of the plurality of medical imaging menus as a target menu to be reviewed;

receive a user selection of at least one of the displayed medical imaging menus;

control to display the selected medical imaging menu in a different format than other of the plurality of medical imaging menus and display a plurality of thumbnail images of first failed images corresponding to the selected medical imaging menu along with photo icons identifying medical staff respectively associated with capturing of the plurality of first failed images, the photo icons being displayed side by side with the thumbnail images, wherein the thumbnail images and corresponding photo icons are arranged in an order based on the second index value;

receive a user selection of at least one second failed image from the plurality of thumbnail images of the first failed images by the user selecting one of the plurality of thumbnail images;

control to display to remove the plurality of thumbnail images from the display and to display the at least one second failed image with the corresponding photo icon of the medical staff member who performed an image capturing corresponding to the at least one second failed image in a larger size than the thumbnail image of the plurality of first failed images upon selection of the at least one second failed image; and control the display to comparably display the at least one second failed image in the larger size side by side with at least one first diagnostic image corresponding to the selected medical imaging menu.

2. The failed image management apparatus according to claim 1, wherein the processor is further configured to:

receive a selection of at least one medical staff member and control to display the plurality of first failed images arranged in order of a second index value in association with a number of the at least one selected medical staff member who performed the image capturing corresponding to each of the plurality of first failed images.

3. The failed image management apparatus according to claim 1, wherein the plurality of medical imaging menus includes a first medical imaging menu and a second medical imaging menu whose first index value is not greater than that of the first medical imaging menu, and wherein the processor is further configured to arrange the first one of medical imaging menus and the second one of medical imaging menus in this order.

4. The failed image management apparatus according to claim 1, wherein the plurality of medical imaging menus includes a first medical imaging menu and a second medical imaging menu, wherein the processor is configured to control to display the plurality of medical imaging menus arranged the first medical imaging menu and the second medical imaging menu in this order, and wherein at least one of a number or a rate of failed images of the first group of medical images corresponding to the first medical imaging menu is greater than that of the second group corresponding to the second medical imaging menu.

5. The failed image management apparatus according to claim 1, wherein the plurality of medical imaging menus includes a first medical imaging menu whose first index value is the maximum among the plurality of arranged medical imaging menus, and wherein the processor is configured to control to display the plurality of medical imaging menus arranged the first medical imaging menu on top of the plurality of medical imaging menus.

6. The failed image management apparatus according to claim 1, wherein the plurality of medical imaging menus includes a first medical imaging menu, wherein the processor is further configured to control to display the plurality of medical imaging menus arranged the first medical imaging menu on top of the plurality of medical imaging menus, and wherein at least one of a number or a rate of failed images of the first medical imaging menu is the maximum among the plurality of medical imaging menus.

7. The failed image management apparatus according to claim 1, wherein the processor is configured to control to display the plurality of medical imaging menus with information on the medical staff member who performed the image capturing corresponding to each of the plurality of medical imaging menus.

8. The failed image management apparatus according to claim 1, wherein the processor is further configured to:

receive a selection of at least one medical staff member who performed the image; and control to display the plurality of medical imaging menus corresponding to the selected at least one medical staff member who performed the image.

9. The failed image management apparatus according to claim 1, wherein the processor is further configured to control to display the plurality of first failed images arranged with information on the medical staff member who performed the image capturing corresponding to each of the plurality of first failed images.

10. The failed image management apparatus according to claim 1, wherein the at least one first diagnostic image is corresponding to a patient of the at least one second failed image.

11. The failed image management apparatus according to claim 1, wherein the processor is further configured to:

receive a selection of at least one medical staff member; and control to display the plurality of first failed images changed image size of the plurality of arranged first failed images based on the second index value in association with a number of the at least one selected medical staff who performed the image capturing.

12. The failed image management apparatus according to claim 1, wherein the processor is further configured to control to display the at least one second failed image with the selected medical imaging menu and at least one of the plurality of medical imaging menus without the selected medical imaging menu.

13. A failed image management method comprising;

calculating, for each of a plurality of medical imaging menus, a first index value based on both a number and a rate of plurality of failed images occurring for the each medical imaging menu;

calculate for each of the failed images, a second index value based on information associated with a medical staff member and a patient corresponding to each failed image;

automatically extracting and displaying, on the basis of the first index value, at least one of the plurality of medical imaging menus as a target menu to be reviewed;

receiving a user selection of at least one of the displayed medical imaging menus;

controlling to display the selected medical imaging menu in a different format than other of the plurality of medical imaging menus and display a plurality of thumbnail images of first failed images corresponding to the selected medical imaging menu along with photo icons identifying medical staff respectively associated with capturing of the plurality of first failed images, the photo icons being displayed side by side with the thumbnail images, wherein the thumbnail images and corresponding photo icons are arranged in an order based on the second index value;

receiving a user selection of at least one second failed image from the plurality of thumbnail images of the first failed images by user selecting one of the plurality of thumbnail images;

controlling to display to remove the plurality of thumbnail images from the display and to display the at least one second failed image with the corresponding photo icon of the medical staff member who performed an image capturing corresponding to the at least one second failed image in a larger size than the thumbnail image of the plurality of first failed images upon selection of the at least one second failed image; and controlling the display to comparably display the at least one second failed image in the larger size side by side with at least one first diagnostic image corresponding to the selected medical imaging menu.

14. A non-transitory computer-readable storage medium that stores a failed image management method causing a computer to execute:

calculating for each of a plurality of medical imaging menus, a first index value based on both a number and a rate of plurality of failed images occurring for the each medical imaging menu;

calculate, for each of the failed images, a second index value based on information associated with a medical staff member and a patient corresponding to each failed image;

automatically extracting and displaying, on the basis of the first index value, at least one of the plurality of medical imaging menus as a target menu to be reviewed;

receiving a user selection of at least one of the displayed medical imaging menus;

controlling to display the selected medical imaging menu in a different format than other of the plurality of medical imaging menus and display a plurality of thumbnail images of first failed images corresponding to the selected medical imaging menu along with photo icons identifying medical staff respectively associated with capturing of the plurality of first failed images, the photo icons being displayed side by side with the thumbnail images, wherein the thumbnail images and corresponding photo icons are arranged in an order based on the second index value;

receiving a user selection of at least one second failed image from the plurality of thumbnail images of the first failed images by the user selecting one of the plurality of thumbnail images;

controlling to display to remove the plurality of thumbnail images from the display and to display the at least one second failed image with the corresponding photo icon 5 of the medical staff member who performed an image capturing corresponding to the at least one second failed image in a larger size than the thumbnail image of the plurality of first failed images upon selection of the at least one second failed image; and 10 controlling the display to comparably display the at least one second failed image in the larger size side by side with at least one first diagnostic image corresponding to the selected medical imaging menu.

\* \* \* \* \* 15